(12) United States Patent
Johnson et al.

(10) Patent No.: US 11,672,671 B2
(45) Date of Patent: Jun. 13, 2023

(54) ARTIFICIAL SPINAL PROSTHESIS AND METHOD

(71) Applicant: Facet Mobility, LLC, Westlake Village, CA (US)

(72) Inventors: J. Patrick Johnson, Los Angeles, CA (US); Christopher Zarembinski, Los Angeles, CA (US); Terrence T. Kim, Los Angeles, CA (US)

(73) Assignee: Facet Mobility, LLC, Westlake Village, CA (US)

( * ) Notice: Subject to any disclaimer, the term of this patent is extended or adjusted under 35 U.S.C. 154(b) by 0 days.

(21) Appl. No.: 17/650,952

(22) Filed: Feb. 14, 2022

(65) Prior Publication Data

US 2022/0168115 A1    Jun. 2, 2022

Related U.S. Application Data

(63) Continuation of application No. 17/449,718, filed on Oct. 1, 2021.

(60) Provisional application No. 63/087,124, filed on Oct. 2, 2020.

(51) Int. Cl.
  *A61F 2/44* (2006.01)
  *A61F 2/30* (2006.01)
  *A61F 2/46* (2006.01)

(52) U.S. Cl.
  CPC ........ *A61F 2/4405* (2013.01); *A61F 2/30767* (2013.01); *A61F 2/46* (2013.01); *A61F 2002/30655* (2013.01); *A61F 2002/30934* (2013.01)

(58) Field of Classification Search
  CPC ...... A61F 2/4405; A61F 2/30767; A61F 2/46; A61F 2002/30655; A61F 2002/30934; A61F 2/4425; A61F 2002/30578; A61F 2002/30884; A61F 2/44; A61F 2/442; A61B 17/7064
  See application file for complete search history.

(56) References Cited

U.S. PATENT DOCUMENTS

| | | | |
|---|---|---|---|
| 8,419,780 B2* | 4/2013 | Bickley | A61B 17/686 606/326 |
| 2005/0065526 A1* | 3/2005 | Drew | A61B 17/88 606/301 |
| 2005/0159746 A1* | 7/2005 | Grob | A61F 2/4405 606/279 |
| 2006/0265074 A1 | 11/2006 | Krishna et al. | |
| 2007/0179616 A1 | 8/2007 | Braddock | |
| 2010/0004657 A1* | 1/2010 | Dudasik | A61F 2/4611 606/86 A |
| 2011/0022173 A1* | 1/2011 | Melkent | A61B 17/8052 606/301 |

(Continued)

*Primary Examiner* — Brian A Dukert
(74) *Attorney, Agent, or Firm* — Knobbe, Martens, Olson & Bear, LLP

(57) ABSTRACT

Methods and systems for treating a spinal joint with a facet joint replacement. The prosthesis can include a first component having a first articulating surface and a second component having a second articulating surface. The first component is attached to a superior articulating facet and the second component is attached to an inferior articulating facet. The first articulating surface and the second articulating surface articulate with each other and allow for multiple degrees of movement of the facet joint without fusing the joint.

23 Claims, 73 Drawing Sheets

(56) References Cited

U.S. PATENT DOCUMENTS

2018/0228619 A1 8/2018 Peterman et al.
2022/0104949 A1 4/2022 Johnson et al.

* cited by examiner

Superior View of the Axis (C2)

Superior View of the Atlas (C1)

Superior View of a typical Cervical Vertebra

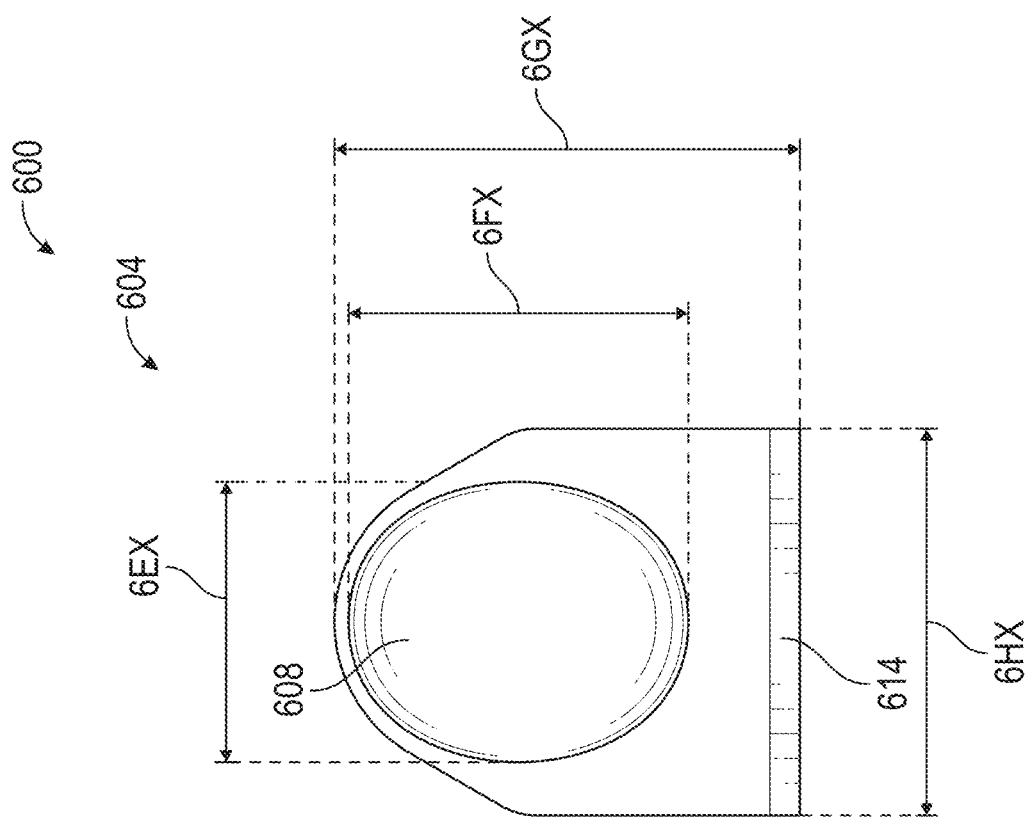
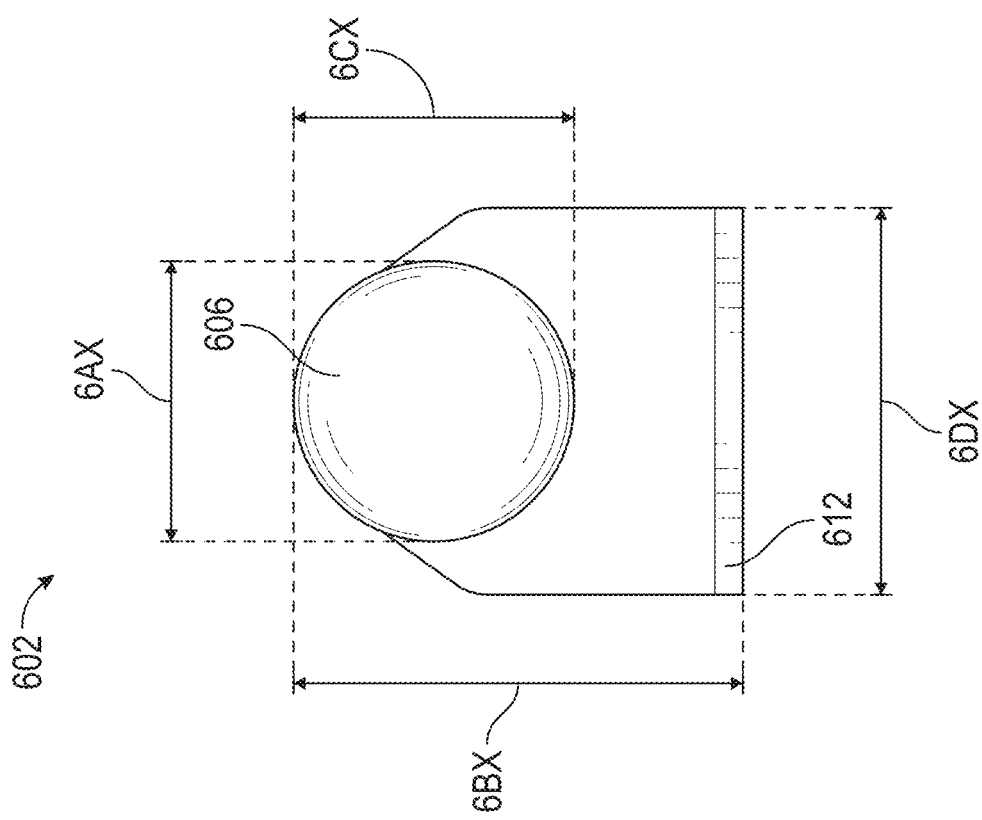
FIG. 5A

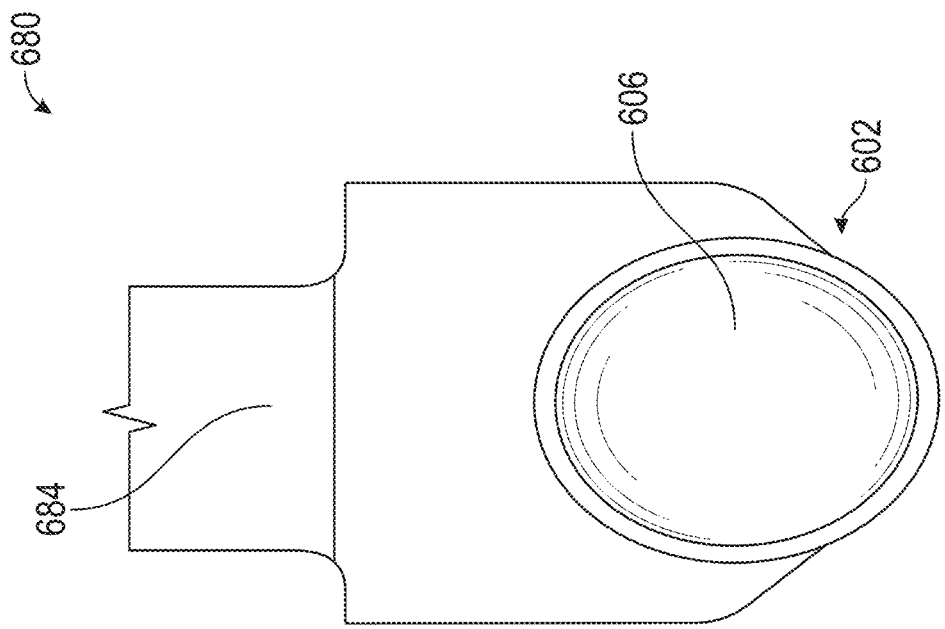
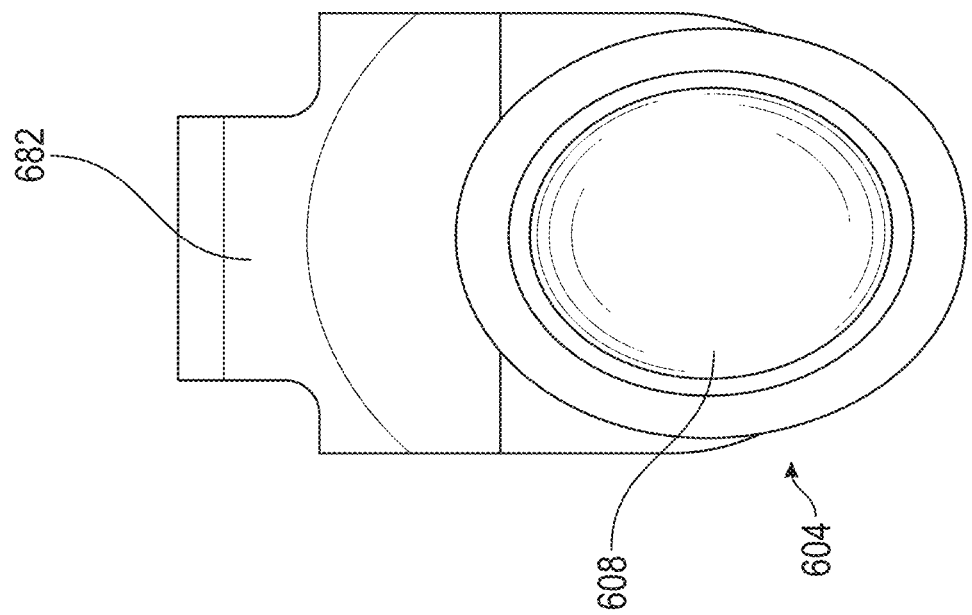
FIG. 5E

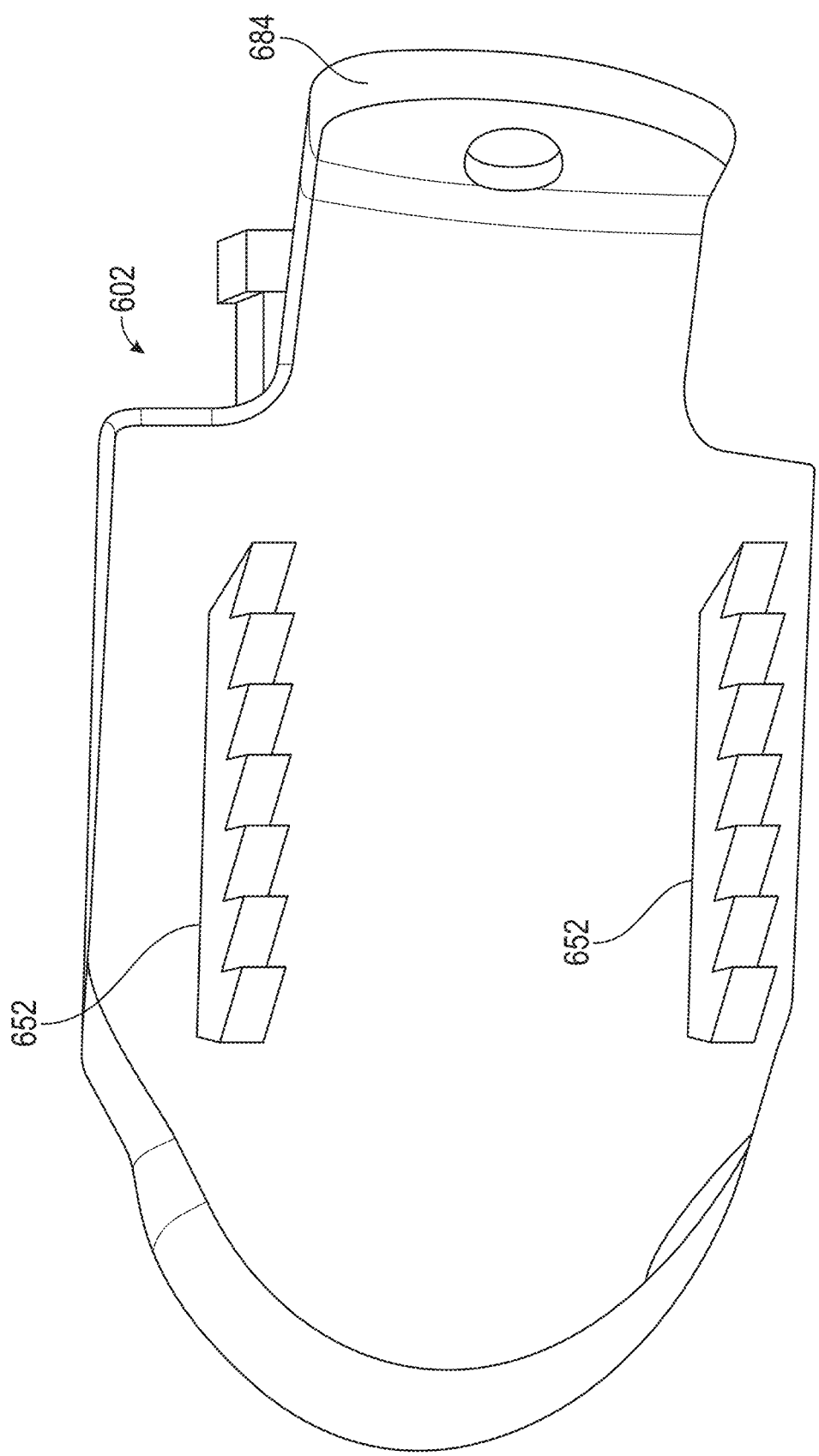

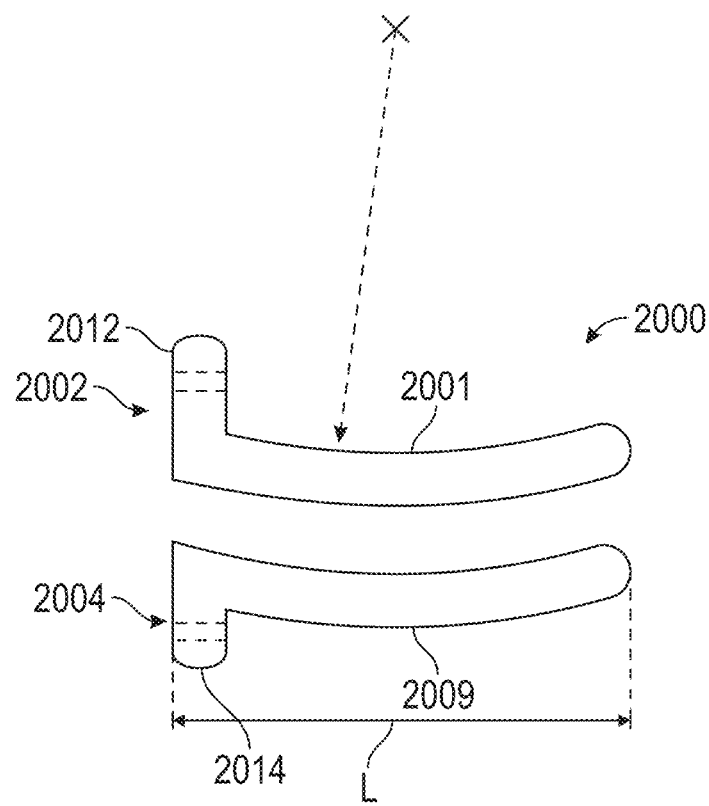
FIG. 20I
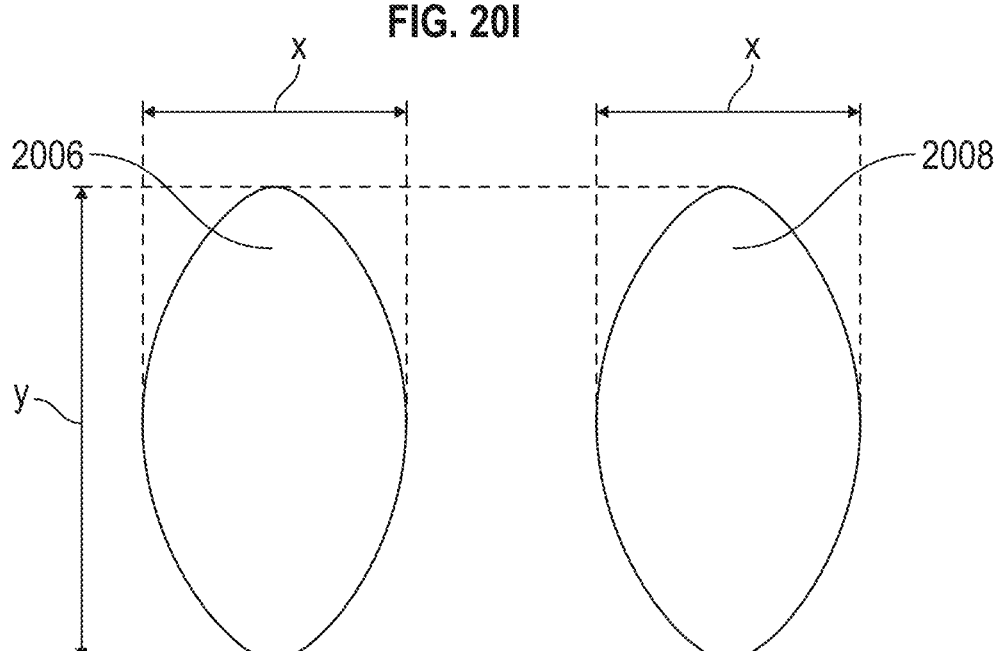
FIG. 20J                FIG. 20K
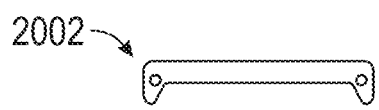      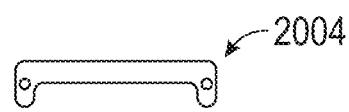
FIG. 20L                FIG. 20M

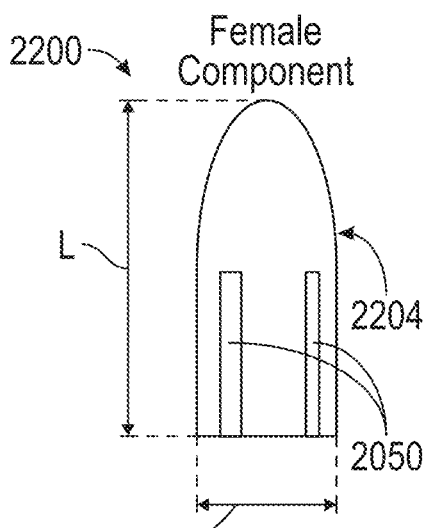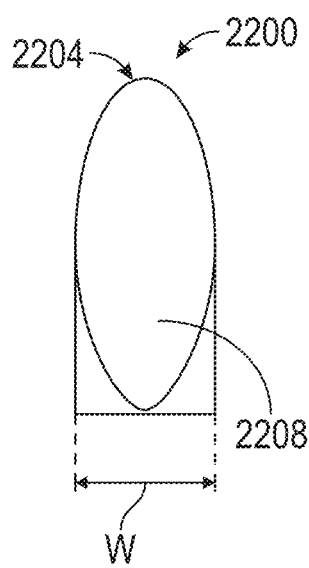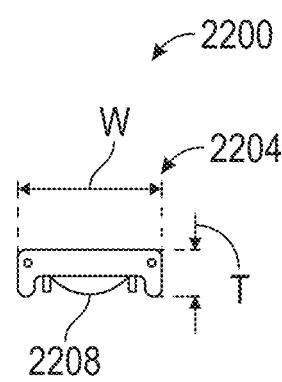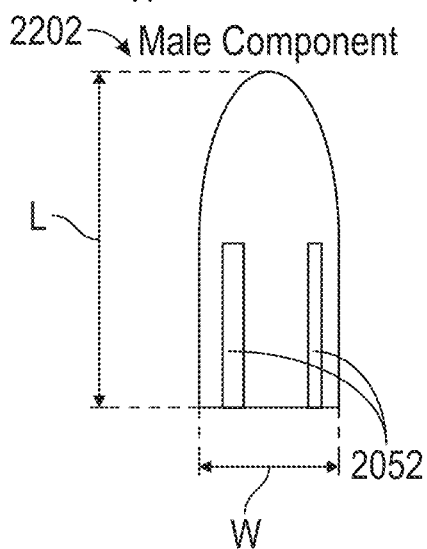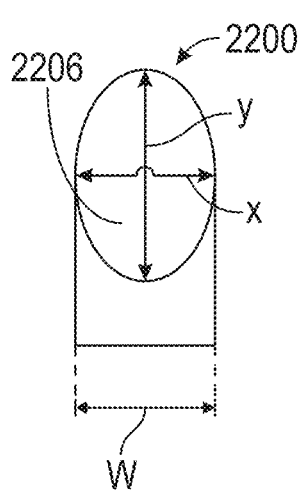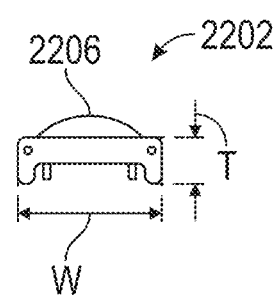
FIG. 22A    FIG. 22B    FIG. 22C
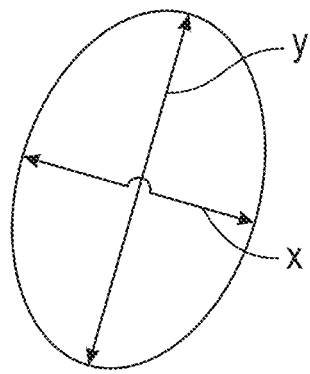
FIG. 22D

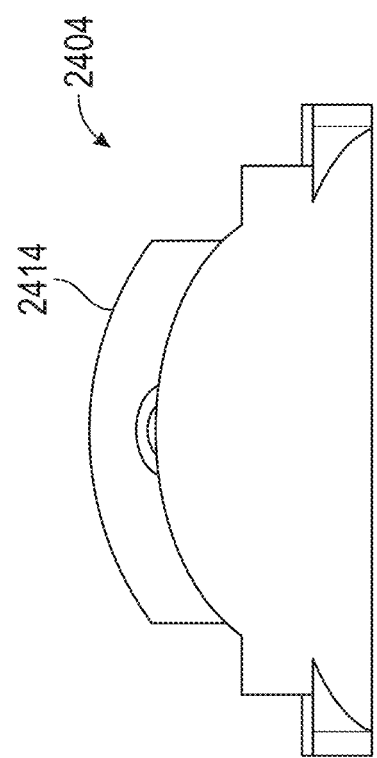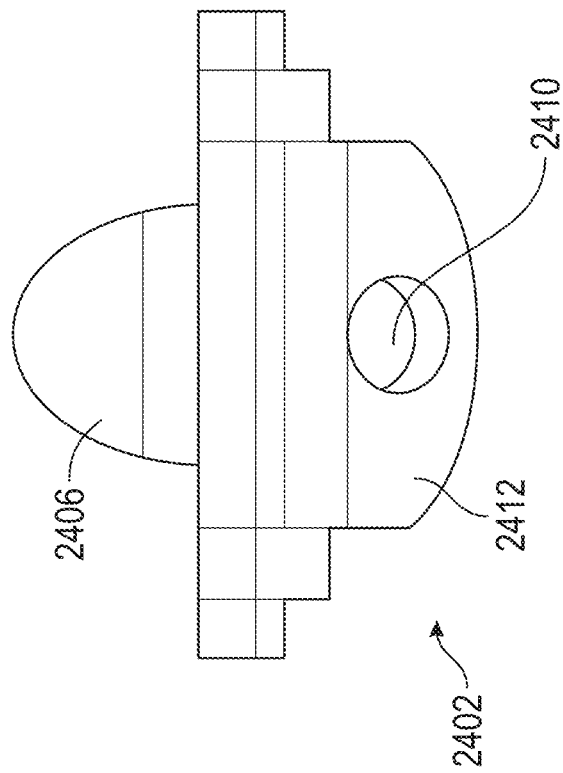
FIG. 24E

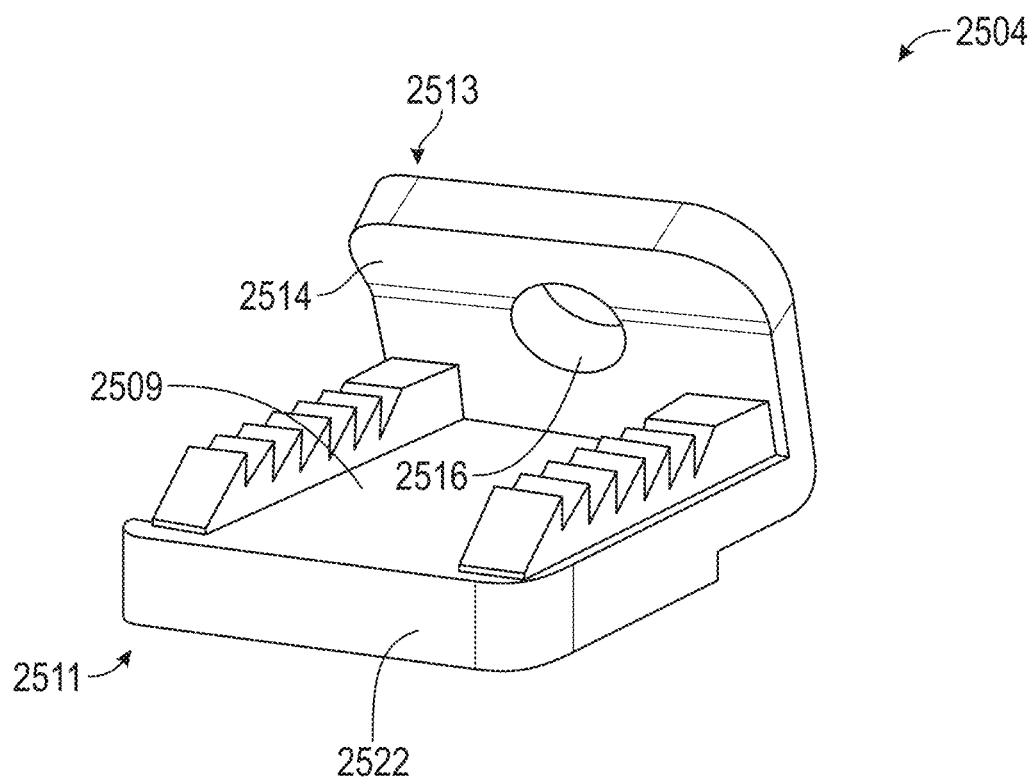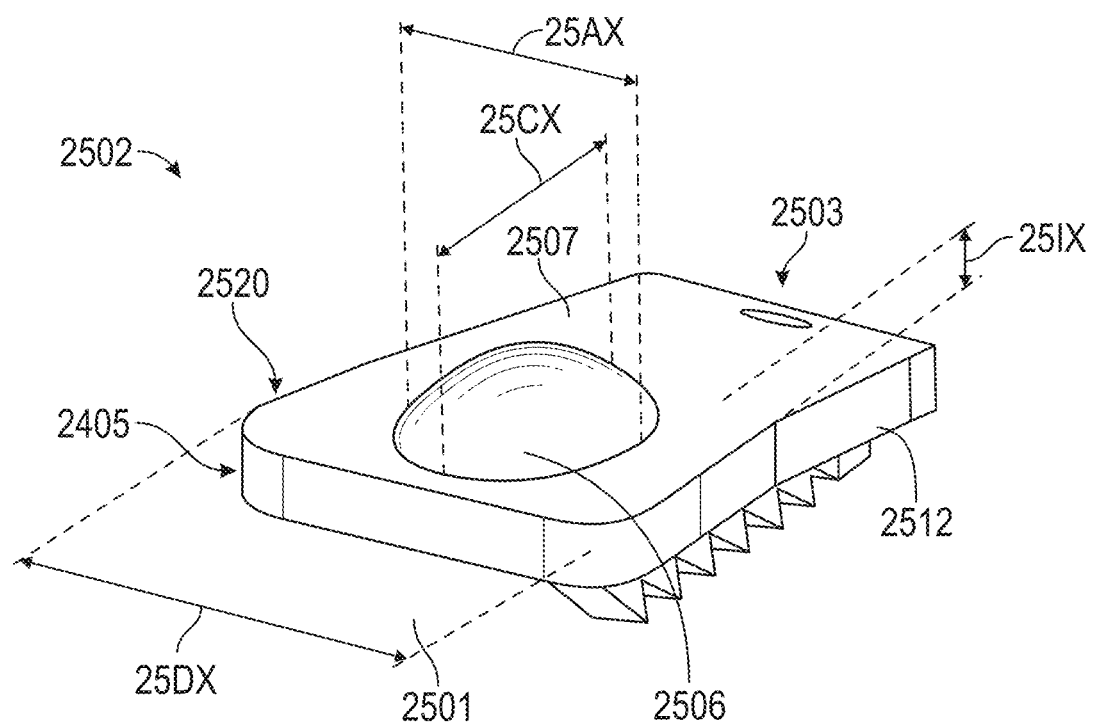
FIG. 25B

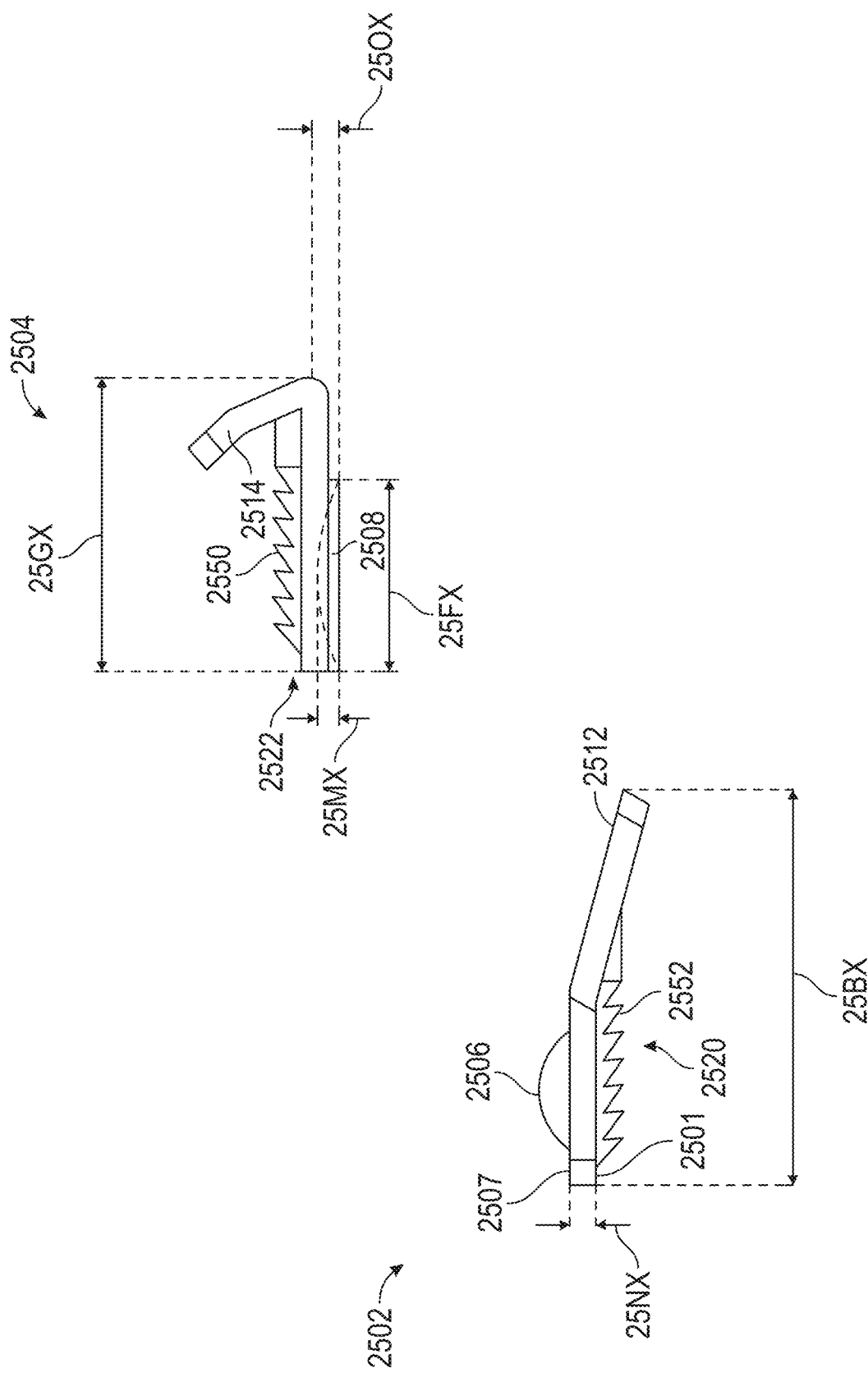

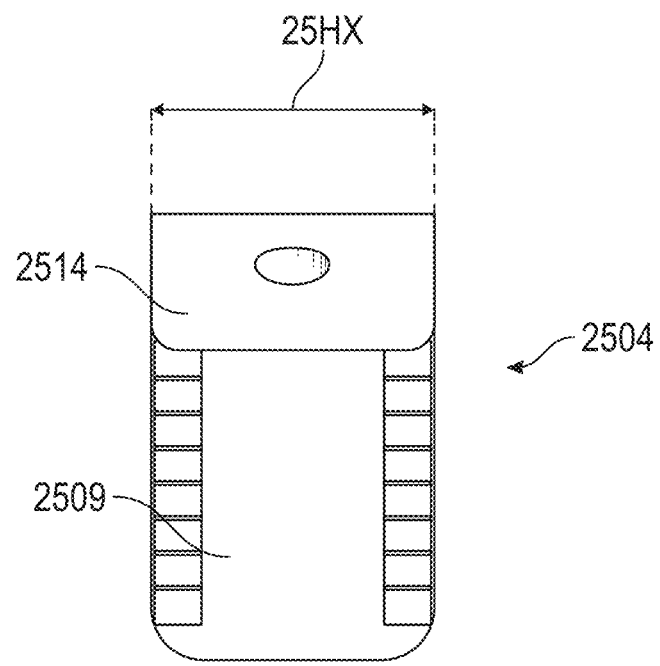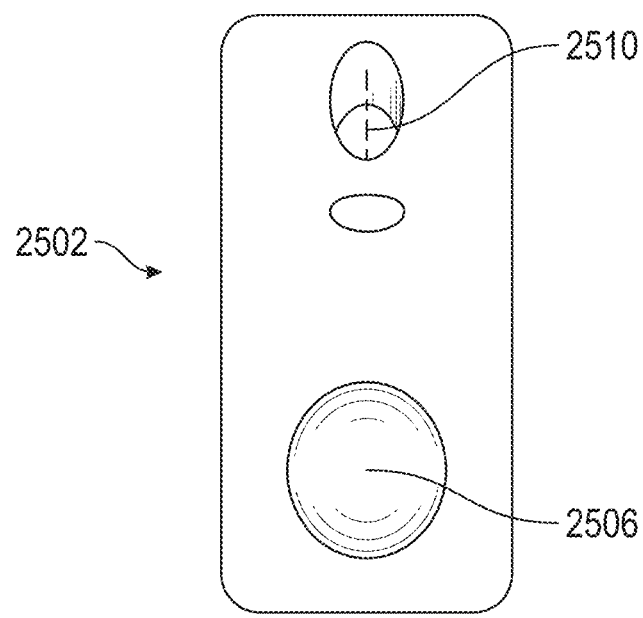
FIG. 25D

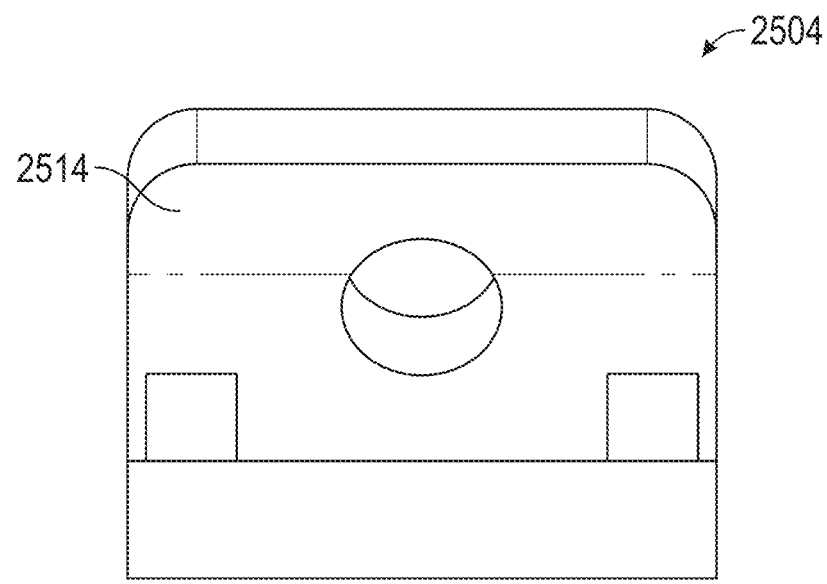
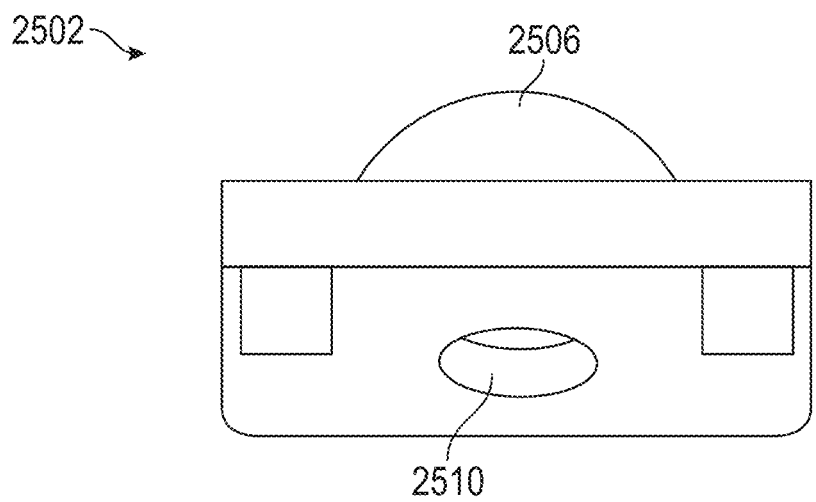
FIG. 25E

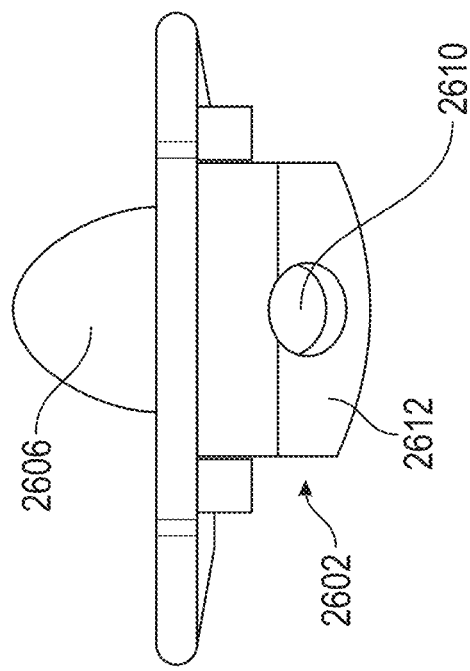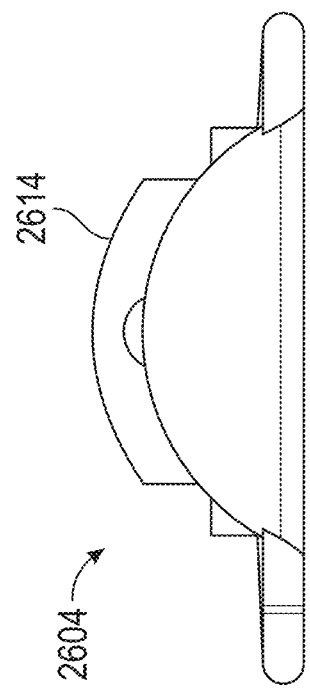
FIG. 26C

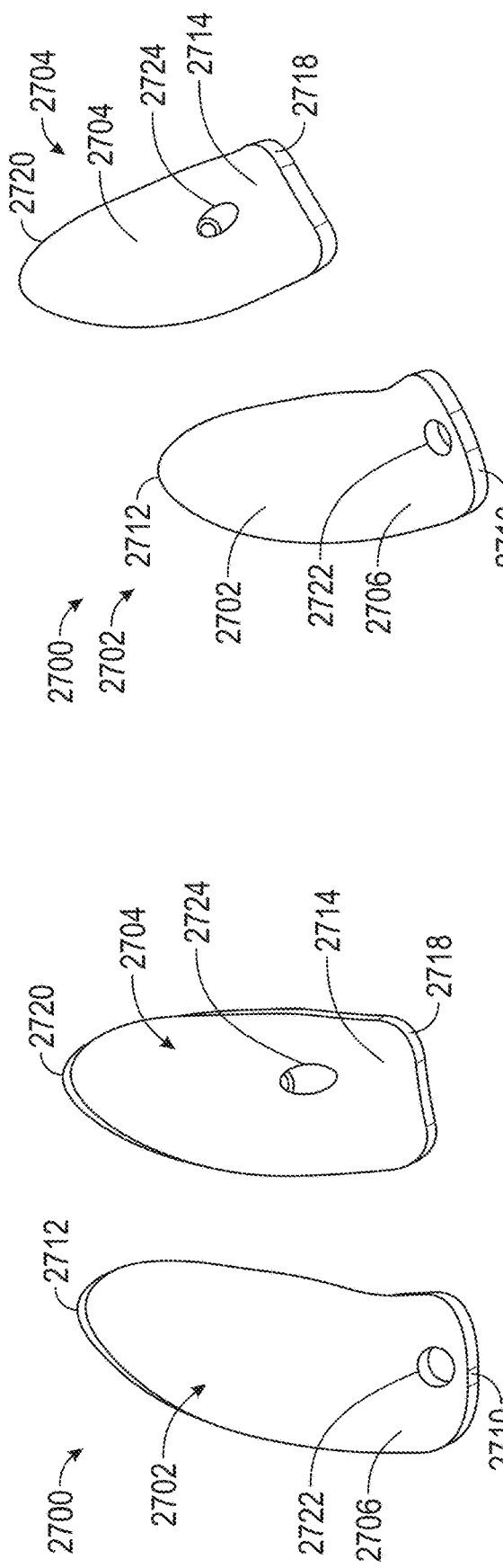
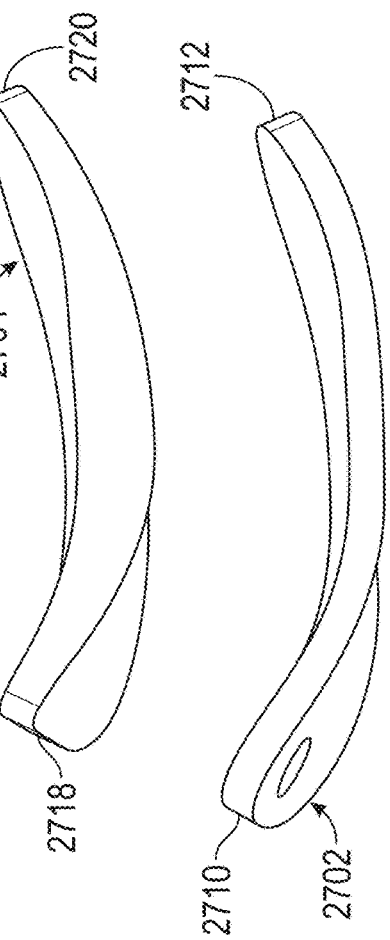
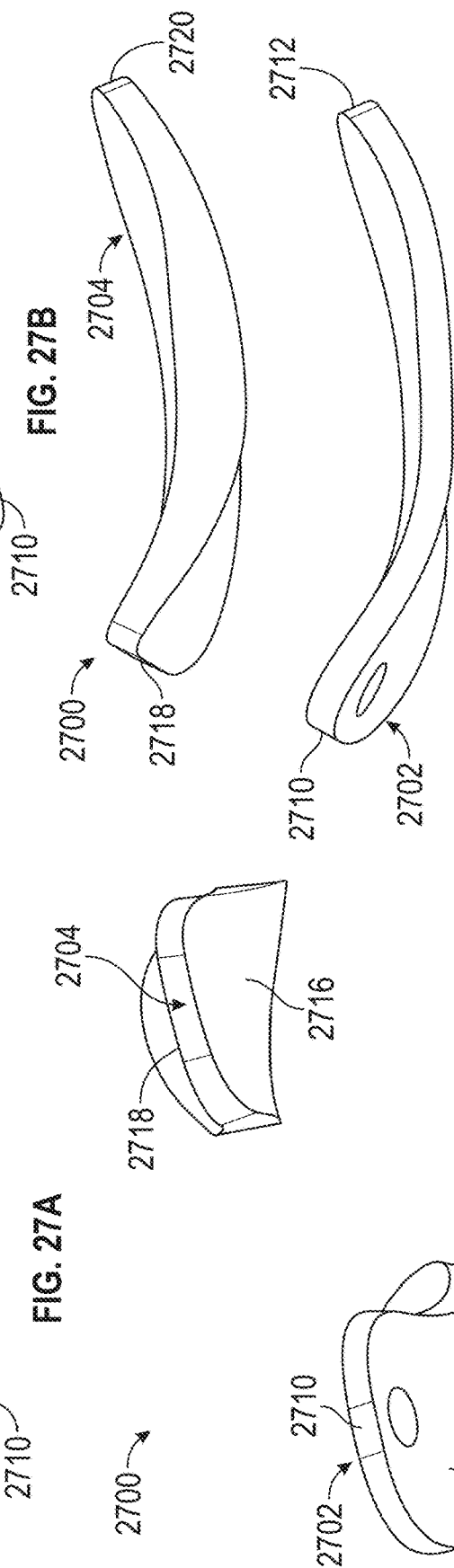
FIG. 27A
FIG. 27B
FIG. 27C
FIG. 27D

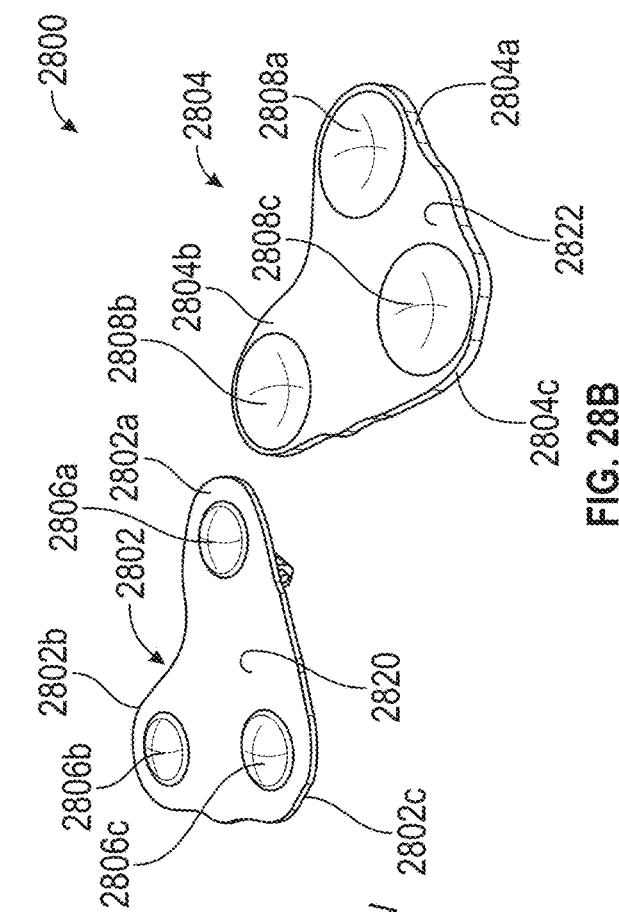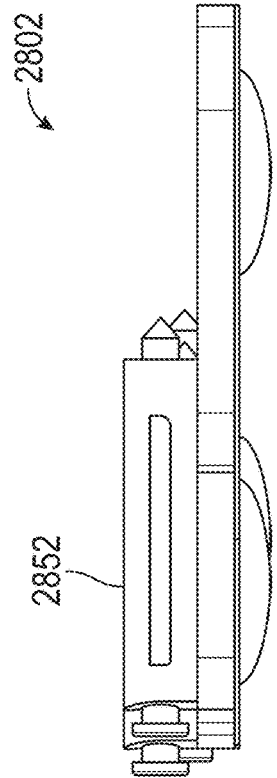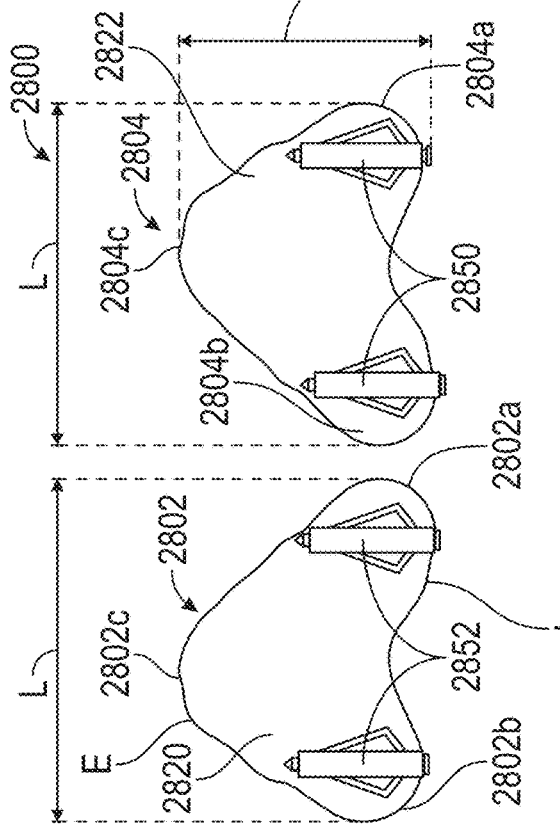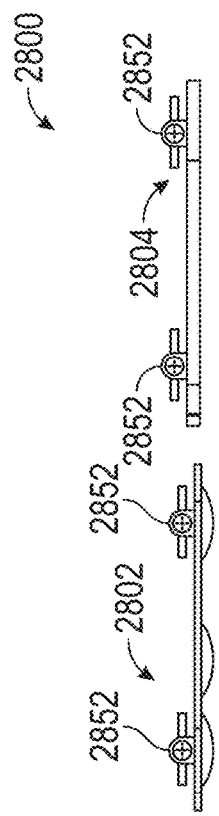
FIG. 28A
FIG. 28B
FIG. 28C
FIG. 28D

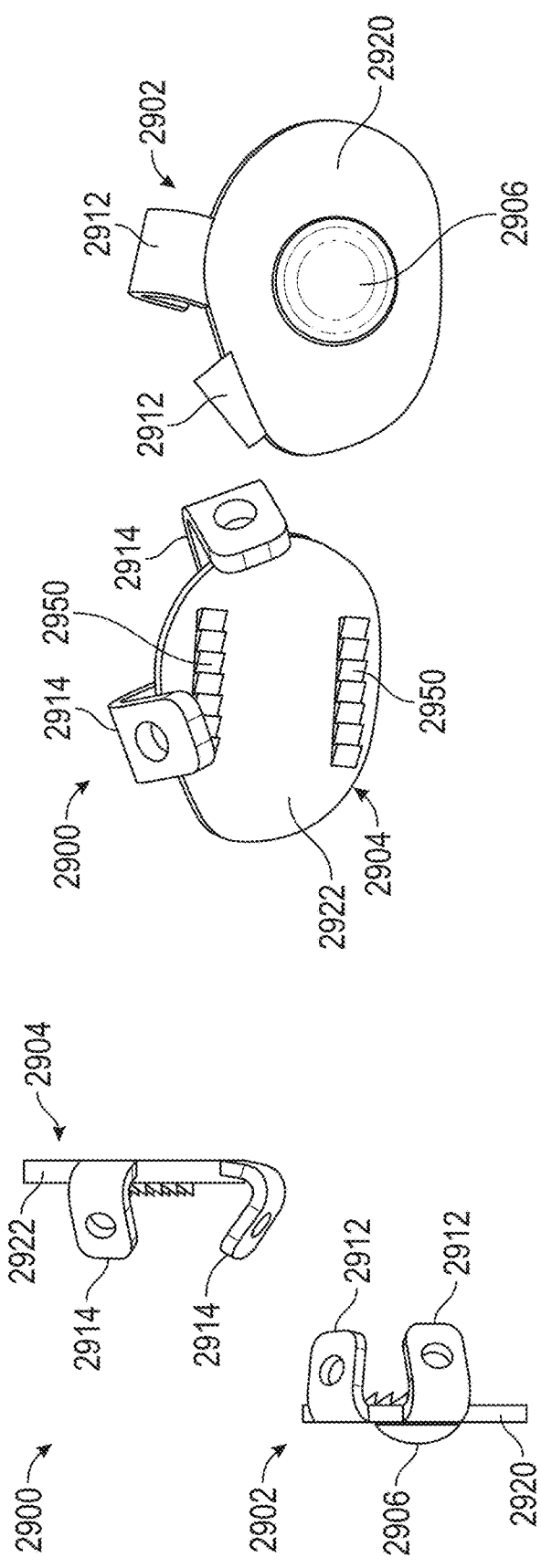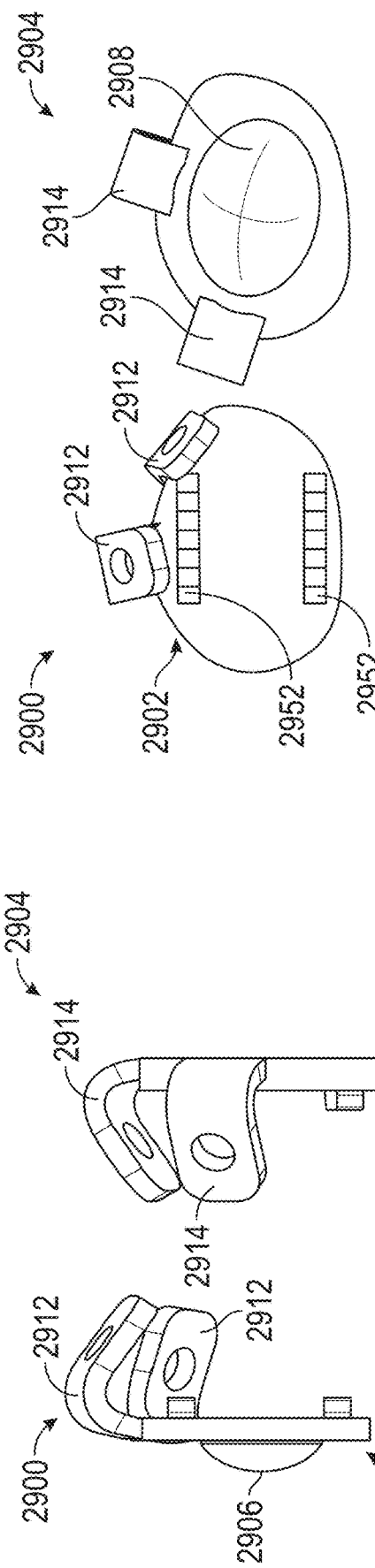

ARTIFICIAL SPINAL PROSTHESIS AND METHOD

INCORPORATION BY REFERENCE TO RELATED APPLICATIONS

This application is a continuation of U.S. application Ser. No. 17/449,718, filed Oct. 1, 2021, which claims priority benefit of U.S. Provisional Application No. 63/087,124, filed Oct. 2, 2020, which is hereby incorporated by reference in its entirety herein.

BACKGROUND

Field

In some aspects, systems and methods relate to an artificial vertebral joint prostheses, including at the occipito-atlantal and atlanto-axial joints, cervical, thoracic, and lumbar facet joints, and sacroiliac joints, for example.

Description of the Related Art

Neck and back pain can be caused by, for example, vertebral joint disease, including osteoarthritis which represents the functional failure of the synovial facet joints. Improved less invasive spinal facet joint prostheses are also needed, as none are FDA approved or commercially available.

SUMMARY

The present disclosure is directed toward artificial spinal facet joint prostheses. The prostheses described herein are designed to treat facet joints, including the occipito-atlantal joint, cervical facet joint, thoracic facet joint, lumbar facet joint, or sacro-illiac joint. The facet joint prostheses described herein could advantageously treat chronic pain and preserve motion without requiring a total disc replacement in some cases. The implants described herein may be placed between adjacent vertebrae of the facet joint without extending into the vertebral disc. The implants may be secured to a posterior side of the facet joint.

The facet joint prostheses exhibit multiple degrees of freedom of movement, including axial rotation, lateral translation, anteroposterior translation, flexion-extension, and/or vertical movement. Different combinations of movement may be preserved and coupled together depending on the on the facet joint being treated. Methods to implant the facet joint prostheses do not fuse or wire the facet joint together.

The facet joint prostheses described herein may include a first component and a second component separate from and not fixed to the second component, even when implanted. For example, when implanted, the first and second components may be separated if not held in close relationship by the ligaments. A superior side of a first component may be placed against an inferior side of a first vertebrae in the region of the facet joint and an inferior side of a second component may be placed against a superior side of a second vertebrae in the region of the facet joint, without extending into the disc region of the vertebrae. One of the components can include one or more ball or convex elements and the other component can include one or more corresponding trough or concave elements. The convex element may be differently shaped and/or sized compared to the concave element depending on the desired movement. Each component may be secured to the bone using one or more screws. Depending on the target facet joint, the component may have a flange contoured to curve along the posterior side of the facet joint.

The contours of the bone facing surfaces of the prostheses described herein may be patient-specific based on based on pre-operative imaging of the patient's facet joint.

Certain aspects of the disclosure are directed to facet joint prosthesis configured to be between adjacent vertebrae in a facet joint. The prosthesis can include a first component configured to be attached to a first vertebrae and a second component configured to be attached to an adjacent second vertebrae. For example, the first component may be placed on an inferior facet of the first vertebrae without extending into the disc space. The second component may be placed on a posterior facet of the second vertebrae without extending into the disc space.

The first component can include a first body portion having a first articulating surface and a first bone facing surface configured to be placed on an articular facet of the first vertebrae. The second component can include a second body portion having a second articulating surface and a second bone facing surface configured to be placed on an articular facet of the second vertebrae. The first articulating surface configured to articulate relative to the second articulating surface. In some embodiments, the first articulating surface include one or more ball elements or one or more trough elements, and the second articulating surface may include the other one of one or more ball elements or one or more trough elements to permit rotational movement. In other embodiments, the prosthesis may include no ball and trough elements. In either configuration, the first component may be configured to translate relative to the second component in a medial-lateral direction and/or anterior-posterior direction. The first component may be able to move vertically relative to the second component. The first component may be able to tilt relative to the second component to permit flexion-extension.

The first component can include at least one flange configured to secure the first component to a posterior-facing side of an articular pillar of the first vertebrae. The at least one flange can be curved or angled relative to the first body portion. Each of the at least one flange can include an aperture configured to receive a first bone anchor. The second component can include at least one flange configured to secure the second component to a posterior-facing side of an articular pillar of the second vertebrae. The at least one flange can be curved or angled relative to the second body portion. Each of the at least one flange can include an aperture configured to receive a second bone anchor. The first bone anchor and/or the second bone anchor may be expandable, for example an expandable screw. Additionally or alternatively, the first component and/or the second component can include at least one keel, for example a pair of keels. The pair of keels may be arranged parallel to each other or in a toe-in configuration. The pair of keels may be expandable.

The first component may include a concave or convex articulating surface. The second component may include the other of a concave or convex articulating surface. A depth of the concave articulating surface may be different from, for example greater than or less than, a height of the convex articulating surface. A diameter of the concave articulating surface may be greater than a diameter of the convex articulating surface. One or both of the concave articulating surface and the convex articulating surface may be non-circular.

The first body portion and the second body portion may be sized to be positioned entirely within the articular facets. For example, a length of each of the first component and the second component may be no more than about 25 mm, no more than 20 mm, or no more than 10 mm. A width of each of the first component and the second component may be no more than about 15 mm or no more than about 10 mm. In some configurations, the first component and the second component may have a generally rectangular foot print or a rounded periphery. In some embodiments, the first component may include a first pair of paddles extending laterally from the first body portion, and the second component may include a second pair of paddles extending laterally from the second body portion. The first pair of paddles may be differently shaped and/or sized from each other. The second pair of paddles may be differently shaped and/or sized from each other or the first pair of paddles.

Disclosed herein is a method of treating occipito-atlantal and atlanto-axial joints, cervical, thoracic, and lumbar facet joints, and sacroiliac facet joints, for example. In some embodiments, disclosed is a method of treating the atlanto-axial joint, comprising: providing an atlanto-axial joint replacement prosthesis, wherein the prosthesis comprises a first component comprising a ball element, and a second component comprising a trough element; attaching the first component to an atlas of the patient; and attaching the second component to an axis of the patient, wherein the ball element and the trough element articulate with each other and allow for lateral motion of the atlanto-axial joint, wherein the method does not fuse the atlanto-axial joint.

In some embodiments, the method does not comprise sub-laminar wiring.

In some embodiments, the first component is not fixed to the second component.

In some embodiments, the method does not comprise transecting the C2 nerve root.

In some embodiments, the prosthesis is delivered via an expandable tube.

In some embodiments, disclosed herein is a method of treating the atlanto-axial joint, comprising: providing an atlanto-axial joint replacement prosthesis, wherein the prosthesis comprises a first component comprising a first articulating surface, and a second component comprising a second articulating surface; attaching the first component to an atlas of the patient; and attaching the second component to an axis of the patient, wherein the first articulating surface is a convex surface, and the second articulating surface is a convex surface or a flat surface.

In some embodiments, the second articulating surface is a convex surface.

In some embodiments, the second articulating surface is a flat surface.

In some embodiments, the first component and the second component comprise curved flanges.

In some embodiments, disclosed herein is a joint replacement system for treating the atlanto-axial joint, comprising: an atlanto-axial joint replacement prosthesis, wherein the prosthesis comprises a first component comprising a ball element, and a second component comprising a trough element; wherein the first component is configured to attach to an atlas of the patient, wherein the second component is configured to attach to an axis of the patient, and wherein the ball element and the trough element articulate with each other and allow for lateral motion of the atlanto-axial joint, wherein the system does not fuse the atlanto-axial joint.

In some embodiments, disclosed herein is a system for treating the atlanto-axial joint, comprising: an atlanto-axial joint replacement prosthesis, wherein the prosthesis comprises a first component comprising a first articulating surface, and a second component comprising a second articulating surface; wherein the first component is configured to attach to an atlas of the patient; wherein the first component is configured to attach to an axis of the patient, and wherein the first articulating surface is a convex surface or a flat surface, and the second articulating surface is a convex surface or a flat surface.

In some embodiments, the second articulating surface is a convex surface.

In some embodiments, the second articulating surface is a flat surface.

In some embodiments, the first component and the second component comprise curved flanges.

In some embodiments, disclosed herein is a method of treating a sub-axial facet joint, comprising: providing a cervical facet joint replacement prosthesis, wherein the prosthesis comprises a first component comprising a ball element, and a second component comprising a trough element; attaching the first component to first cervical vertebrae of the patient; and attaching the second component to a second cervical vertebrae of the patient directly inferior to the first cervical vertebrae, wherein the ball element and the trough element articulate with each other and allow for lateral motion of the atlanto-axial joint, wherein the method does not fuse the facet joint.

In some embodiments, the method does not comprise performing any sub-laminar wiring.

In some embodiments, the first component is not fixed to the second component.

In some embodiments, the method does not comprise transecting a cervical nerve root.

In some embodiments, the prosthesis is delivered via an expandable tube.

In some embodiments, disclosed herein is a method of treating a cervical facet joint, comprising: providing a cervical facet joint replacement prosthesis, wherein the prosthesis comprises a first component comprising a first articulating surface, and a second component comprising a second articulating surface; attaching the first component to a first cervical vertebrae of the patient; and attaching the second component to a second cervical vertebrae of the patient, wherein the first articulating surface is a convex surface, and the second articulating surface is a concave surface or a flat surface.

In some embodiments, the second articulating surface is a concave surface.

In some embodiments, the second articulating surface is a flat surface.

In some embodiments, the first component and the second component comprise curved flanges.

In some embodiments, disclosed herein is a joint replacement system for treating a sub-axial cervical facet joint, comprising: a cervical facet joint replacement prosthesis, wherein the prosthesis comprises a first component comprising a ball element, and a second component comprising a trough element; wherein the first component is configured to attach to a first cervical vertebrae of the patient, wherein the second component is configured to attach to a second cervical vertebrae of the patient, and wherein the ball element and the trough element articulate with each other and allow for motion of the cervical facet joint, wherein the system does not fuse the cervical facet joint.

In some embodiments, disclosed herein is a system for treating a sub-axial cervical facet joint, comprising: a cervical facet joint replacement prosthesis, wherein the prosthesis comprises a first component comprising a first articulating surface, and a second component comprising a second articulating surface; wherein the first component is configured to attach to a first cervical vertebrae of the patient, wherein the second component is configured to attach to a second cervical vertebrae of the patient, and wherein the first articulating surface is a convex surface, and the second articulating surface is a concave surface or a flat surface.

In some embodiments, the second articulating surface is a concave surface.

In some embodiments, the second articulating surface is a flat surface.

In some embodiments, the first component and the second component comprise curved flanges.

In some embodiments, disclosed herein is a method of treating a spinal joint, comprising: providing a spinal joint replacement prosthesis, wherein the prosthesis comprises a first component comprising a ball element, and a second component comprising a trough element; attaching the first component to a superior articulating structure of the patient; and attaching the second component to an inferior articulating structure of the patient, wherein the ball element and the trough element articulate with each other and allow for lateral motion of the spinal joint, wherein the method does not fuse the spinal joint.

In some embodiments, the method does not comprise sub-laminar wiring.

In some embodiments, the first component is not fixed to the second component.

In some embodiments, the prosthesis is delivered via an expandable tube.

In some embodiments, the joint is a facet joint.

In some embodiments, the joint is the occipito-atlantal joint.

In some embodiments, the joint is a cervical facet joint.

In some embodiments, the joint is a thoracic facet joint.

In some embodiments, the joint is a lumbar facet joint.

In some embodiments, the joint is a sacro-iliac joint.

In some embodiments, the method further comprises implanting a first spinal joint replacement prostheses in an intervertebral disc joint, and at least a second spinal joint replacement prostheses in a non-intervertebral disc joint.

In some embodiments, a system can comprise, not comprise, consist essentially of, or consist of any number of features as disclosed herein.

In some embodiments, a method can comprise, not comprise, consist essentially of, or consist of any number of features as disclosed herein.

Certain aspects of the disclosure are directed to a method of treating the occipito-atlantal joint. The method can include providing an occipito-atlantal joint replacement prosthesis. The prosthesis may include a first component having a first articulating surface without a ball or trough feature, and a second component having a second articulating surface without a ball or trough feature. The first articulating surface may slide relative to the second articulating surface in an anterior-posterior direction and/or a medial-lateral direction. The method may include attaching the first component to an occiput of the patient, for example by driving a first anchoring element through the first articulating surface. The method may include attaching the second component to an atlas of the patient, for example by driving a second anchoring element through the second articulating surface. The first and second anchoring elements may be expandable anchors, for example expandable screws. The first component may be positioned entirely on an interior facet, and the second component may be positioned entirely on a superior facet.

Certain aspects of the disclosure are directed to a joint replacement system for treating the occipito-atlantal joint. An occipito-atlantal joint replacement prosthesis may include a first component having a first articulating surface and a first bone facing surface. The prosthesis may include a second component comprising a second articulating surface and a second bone facing surface. Neither the first component nor the first component may have ball and trough elements. The first component and the second component may articulate with each other and allow for lateral motion and anterior-posterior motion of the occipito-atlantal joint without fusing the occipito-atlantal joint.

The first component may include a first aperture extending through the first articulating surface and the first bone facing surface. The first aperture may be configured to receive a first bone anchor. The entrance and exit of the first aperture may be offset such that the first aperture extends at an angle relative to the first component. The second component may include a second aperture extending through the second articulating surface and the second bone facing surface. The second aperture may be configured to receive a second bone anchor. The entrance and exit of the second aperture may be offset such that the second aperture extends at an angle relative to the second component. The first and second bone anchors may be expandable, for example expandable screws.

Certain aspects of the disclosure are directed toward a method of treating a lumbar facet joint. The method may include providing a lumbar joint replacement prosthesis having a first component and a second component. The first component may have a ball element or a trough element, and the second component may have the other one of the ball element or the trough element. The method may include attaching the first component to a lumbar facet of a first vertebrae and attaching the second component to a lumbar facet of a second vertebrae. The ball element and the trough element may articulate with each other without fusing the lumbar facet joint.

Certain aspects of the disclosure are related to joint replacement system for treating the lumbar facet joint. The lumbar joint replacement prosthesis may include a first component comprising a ball element and a second component comprising a trough element. The first component may be configured to attach to a lumbar facet of a first vertebrae of the patient, and the second component may be configured to attach to a lumbar facet of a second vertebrae. The first component and the second component may articulate with each other without fusing the lumbar facet joint, for example the first component and the second component may rotate and/or translate relative to each other in the medial-lateral and/or anterior-posterior direction.

The first component may have a body portion with a rounded periphery. The first component may include a pair of curved flanges for securing the first component to a posterior facing side of the articular pillar. The second component may have a body portion with a rounded periphery. The second component may include a pair of curved flanges for securing the second component to a posterior facing side of the articular pillar. Additionally or alternatively, the first component and/or the second component may include a pair of keels.

The ball element and/or the trough element may be non-circular, for example the ball element may be circular and the trough element may be non-circular. A diameter of the trough element may be at least 1.5×, at least 2.0×, or at least 2.5× greater than a diameter of the ball element.

Certain aspects of the disclosure are related to a method of treating a sacro-illiac joint. The method may include providing a sacro-illiac joint replacement prosthesis having a first component with a plurality of ball elements and a second component with a plurality of trough elements. The method may include attaching one of the first component or the second component to a sacrum of the patient and attaching the other one of the first component or the second component to the illium of the patient. The ball element and the trough element may articulate with each other without fusing the sacro-illiac joint.

Certain aspects of the disclosure are directed joint replacement system for treating the sacro-illiac joint. The sacro-illiac joint replacement prosthesis may include a first component having a first body portion with a plurality of ball elements, for example three ball elements, and a first bone facing surface, and a second component having a second body portion with a plurality of trough elements, for example three trough elements, and a second bone facing surface. The first component or the second component is configured to attach to a sacrum of the patient, and the other one of the first component or the second component is configured to attach to the illium of the patient. The first component and the second component are configured to articulate with each other without fusing the sacro-illiac joint.

The first body portion may include a pair of wings extending at an angle relative to each other. The pair of wings may have different lengths. Each wing may include a ball element or a trough element. The second body portion may include a pair of wings extending at an angle relative to each other. The pair of wings may have different lengths. Each wing may include a ball element or a trough element.

The first component may include a pair of expandable anchoring elements along the first bone facing surface. The expandable anchoring elements may extend from a posterior edge of the first component toward an anterior edge of the first component. The expandable anchoring elements may be oriented parallel to each other. The expandable anchoring elements may extend in a plane generally parallel to a plane of the first body portion. The expandable anchoring elements may be expandable keels that expand radially outward.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIGS. 5A-5D illustrate another example of a joint prostheses that can be placed in the atlanto-axial joint.

FIGS. 5E-5Q illustrate yet another example of a joint prostheses that can be placed in the atlanto-axial joint.

FIGS. 20I-20M illustrate another joint prosthesis that can be placed in the occipito-atlantal joint.

FIGS. 22A-22E illustrate a joint prosthesis that can be placed in a lumbar facet joint.

FIGS. 24A-24E illustrate another joint prosthesis that can be placed in the atlanto-axial joint.

FIGS. 25A-25E illustrate another joint prosthesis that can be placed in the sub-axial cervical joint.

FIG. 26A-26D illustrate another joint prosthesis that can be placed in the atlanto-axial joint.

FIGS. 27A-27F illustrate a joint prosthesis that can be placed in the occipito-atlantal joint.

FIGS. 28A-28D illustrate a joint prosthesis that can be placed in the sacro-iliac joint.

FIGS. 29A-29E illustrate a joint prosthesis that can be placed in a lumbar facet joint.

DETAILED DESCRIPTION

Figure 1B:
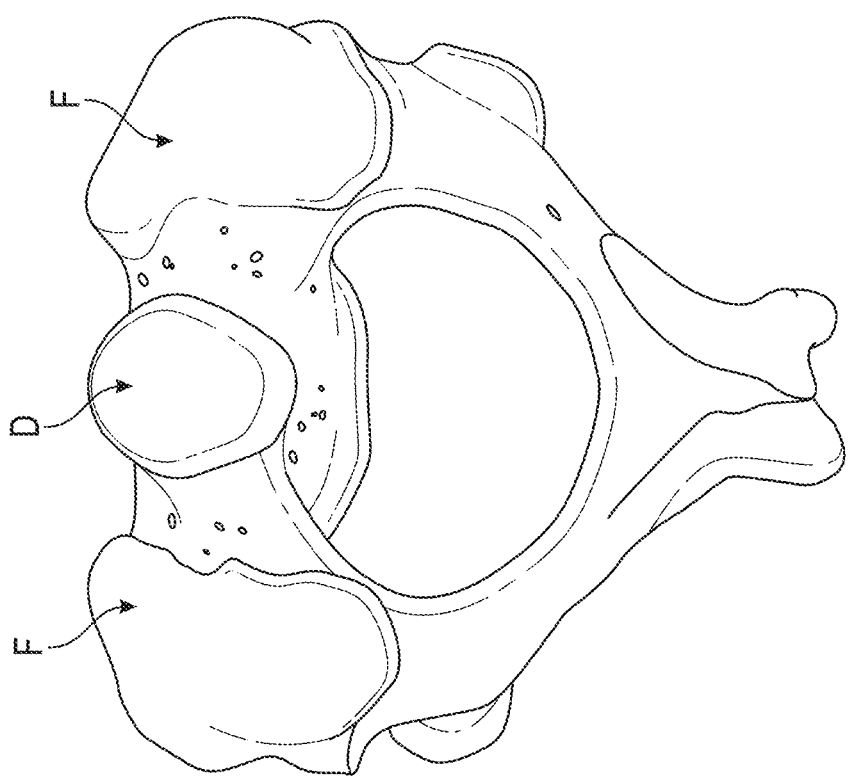
FIG. 1B shows a superior view of the second cervical vertebra (also referred to as the axis or C2).

In some aspects, systems and methods relate to artificial vertebral joint prostheses and methods of use. Any number of joints can be treated, including, for example, at the occipito-atlantal and atlanto-axial joints, as well as one or more of the cervical, thoracic, and lumbar facet joints, and sacroiliac joints.

A wide range of artificial joint prostheses are available for partially or completely replacing the function of native intervertebral discs between adjacent vertebrae in the vertebral column. The intervertebral discs are symphysis (fibrocartilagenous), slightly movable joints. The facet joints, atlanto-axial joints, and the atlanto-occipital joints, each of which do not comprise intervertebral discs, differ anatomically and functionally from the intervertebral disc joints. For example, the facet joints prevent two adjacent vertebrae from engaging in relative motions that could overload and damage the surrounding spinal structures, such as the intervertebral disc, the nerve roots that exit the spinal column, and the spinal cord. The facet joints are plane joints (also called an arthrodial joint, gliding joint or plane articulation) which are synovial joints which allows only gliding movement in the plane of the articular surfaces. The opposed surfaces of the bones are flat or almost flat, with movement generally limited by tight capsules and ligaments. The atlanto-axial joint is primarily involved with cervical rotation, and has increased flexibility compared to intervertebral disc joints. The primary movement of the atlanto-occipital joint is flexion-extension. Treatment of the foregoing non-intervertebral disc spinal joints has conventionally been limited to fusion procedures, as the number of joint replacement devices has been limited and to the inventors' knowledge few to none have been FDA approved, let alone achieved any degree of clinical or commercial success. The inventors have unexpectedly discovered that certain types of prostheses conventionally used to treat intervertebral disc joints, as is or with some modifications, are highly clinically advantageous for use in at least partially non-intervertebral disc joints, despite the vastly different anatomy and kinematics of these non-intervertebral disc joints.

In some embodiments, the artificial non-intervertebral disc joint prosthesis can be any of a variety of types of prostheses, including but not limited to mechanical prostheses such as ball-and-socket, ball-and-trough, hinged or pivotable devices, or devices with complementary sliding surfaces (e.g., metal-on-metal, or metal-on-plastic for example). Prostheses can also include hydraulic devices, elastic devices, or composite devices. In some embodiments, no joints are fused together. In some embodiments, the lamina and the facet joints are spared/not removed during the procedure.

Several non-limiting embodiments of indications and prostheses will now be described. While some device configurations are specifically listed under one indication (e.g., atlanto-axial), they can be used or configured for use for other indications described elsewhere herein (e.g., sub-cervical facet, thoracic, lumbar, sacroiliac, etc.).

Atlanto-Axial

The C1-2 (atlanto-axial) joint is unique and is responsible for more than 50% of neck rotation. Pain from the C1-2 joint typically causes unilateral neck pain associated with rotation to the side of the arthropathic joint. Pain may radiate to the occiput, the parietal skull and rarely to the eye, and is associated with localized muscle spasm. Improved systems and methods of treating C1-2 joint pain are needed. Neck pain can also be caused by, for example, cervical facet joint disease, including osteoarthritis which represents the functional failure of the synovial facet joints. Improved cervical facet joint prostheses are also needed.

An artificial joint or C1-2 arthroplasty, including systems and methods described herein can enhance range of motion and markedly improve quality of life. In some embodiments, a C1-2 artificial joint that mimics motion of the normal joint could be very advantageous in improving outcomes.

Neck pain is a common complaint in the general population. Yin and Bogduk reported a prevalence of zygapophysial joint pain of 55%, discogenic pain of 16%, and atlanto-axial joint pain of 9%.

Treatment options of C1-2 joint pain are limited. Fusion of the C1-2 joint compromises cervical rotation, thereby adversely affecting the patient's quality of life, with an up to 33% incidence of C2 nerve dysfunction in some studies. As such, some embodiments do not involve a joint fusion procedure, such as a C1-2 fusion procedure.

Sublaminar wiring techniques have been developed. Unfortunately, primary stability following sublaminar wiring and bone grafting is often poor, requiring prolonged postoperative immobilization with a considerable rate of non-union. The placement of the sublaminar wires increased the chance of injury to neural structures within the spinal canal. As such, some systems and methods as disclosed herein do not include sublaminar wiring.

Magerl's technique consists of "in situ" C1-2 transarticular screw fixation with posterior wiring to hold bone graft. This technique avoided the need for external orthosis. Unfortunately screw placement was associated with risk of vertebral artery injury.

Wright noted 4.1% incidence of vertebral artery injury, and risk of neurological deficit from vertebral artery injury was 0.2%.

In Harms's technique, polyaxial screws are independently inserted in C1 lateral masses and C2 pedicles and connected by a rod. Harms's technique permits direct intraoperative reduction of C1-2 misalignment without posterior wiring and sparing of occiput. Unfortunately, C2 pedicle screws may violate the foramen transversarium, and some embodiments do not require C2 pedicle screws. As a result, crossed translaminar C2 screws have been suggested as an alternative.

C1 lateral mass screws may impinge the C2 nerve root, requiring screw removal. As such, some embodiments do not include C1 lateral mass screws.

C1-2 fusion with the Goel technique uses a screw-plate system for atlantoaxial fixation, cutting the C2 nerve root. This places the patient at risk for occipital neuralgia or numbness. Some embodiments spare the C2 nerve root. Some embodiments include ball and trough elements that are offset (e.g., not symmetrical) with the axial midline of the implant.

The most common complication of C1-C2 fusion was related to instrumentation failure after nonunion with rate of 6.7%. Injury to the vertebral artery during C1-2 transarticular screws 4.1%, especially in case of high-riding vertebral artery. Other complications include, for example, dural tears, wound infection, risk of neurological deficit from vertebral artery injury (~0.2%), C2 neurotmesis leading to occipital neuralgia, occipital numbness, C2 pedicle screw violation of foramen transversarium, and a C2 pedicle screw fracture. Some embodiments as disclosed herein do not involve C1-2 fusion, or fusion of any other joints.

Atlanto-axial osteoarthritis can be divided into the following sub-categories: idiopathic, degenerative, and post-traumatic. In the elderly, it is most often a result of a degenerative disorder, and in younger patients is due to trauma. Typically, most patients are female (74%) and present with unilateral osteoarthritis. The severity of osteoarthritis increases exponentially with age, and is associated with dens fractures.

The cervical vertebrae are typically the smallest movable vertebrae, forming the bony skeleton of the neck. A key distinctive feature is the presence of an oval foramen transverserium (e.g., foramen of the transverse process). The vertebral arteries run through the foramina in the transverse processes, with the exception of that of C7, which houses small accessory vertebral veins. C3-6 have short, bifid spinous processes, while the spinous process of C7 is typically much longer. The cervical vertebrae typically have almost equal-sized vertebral notches.

C1 and C2 have an especially unique anatomy. C1 is a ring-shaped bone known as the atlas, supporting the skull. The concave superior articular facets of C1 receive the occipital condyles. The atlas lacks a spinous process or body, having only anterior and posterior arches, each having a tubercle and lateral mass. In contrast, C2 is considered the strongest cervical vertebrae, known as the axis because C1 carrying the skull rotates onto C2 (the axis), such as when a person shakes their head. As shown in FIG. 1B, C2 includes two large flat bearing surfaces F—the superior articular facets of which the atlas rotates. C2 also uniquely includes the odontoid process (dens) D projecting superiorly from the body. Each facet joint may receive a separate prosthesis as described herein, for example a C2 component may be positioned on each of the two large flat bearing surfaces F. The dens is maintained in position by the transverse ligament of the atlas, see FIGS. 2A-2B, which prevents horizontal displacement of the atlas. C2 also includes a large bifid spinous process. Comparison of C1-2 joint morphology with other cervical joints illustrates the aforementioned differences between C1-2 and other cervical joints.

The atlanto-axial joint's long axis is oriented obliquely, and joint innervation is from the ventral rami of C2. The articular surface of the axis is convex, and allows approximately 40 degrees of rotation to either side of midline. The atlanto-axial joint includes the left and right lateral atlanto-axial joints, as well as the median atlantoaxial joint. Pain caused by joint arthritis and other conditions can be localized to the sub-occipital, postauricular level.

Figure 1A:
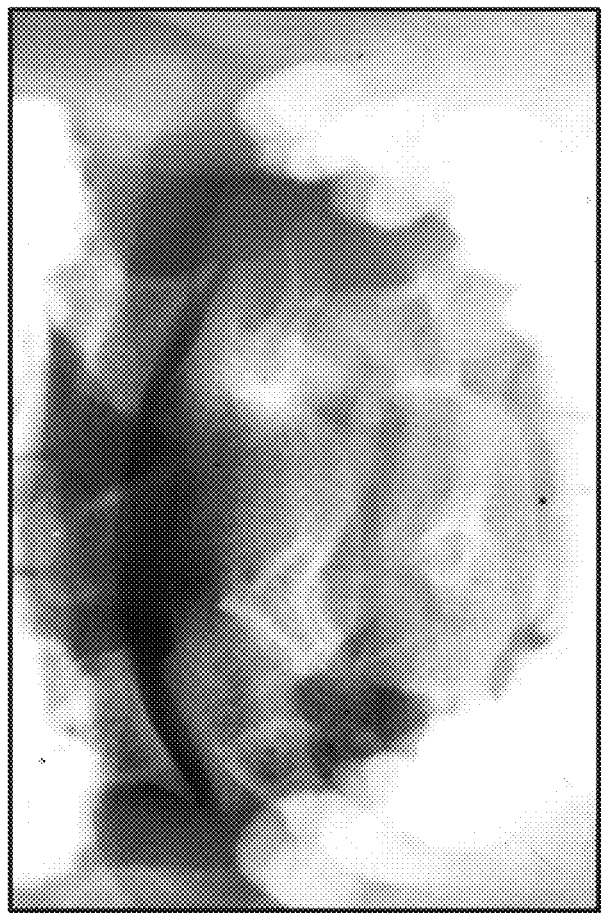
FIG. 1A is an x-ray showing the relationship between C1 and C2 through an opened mouth.

The articular surfaces of C1-C2 are generally flat in the sagittal plane and inclined in the coronal plane (about 165 degrees to the foramen magnum), as shown in FIGS. 1A and 1B. C1-2 stability is maintained by strong ligaments and the unique bony architecture itself.

The anterior movement of the dens is prevented by the C1 anterior arch, whereas the posterior movement is checked by the transverse ligament.

Figures 2A, 2B:
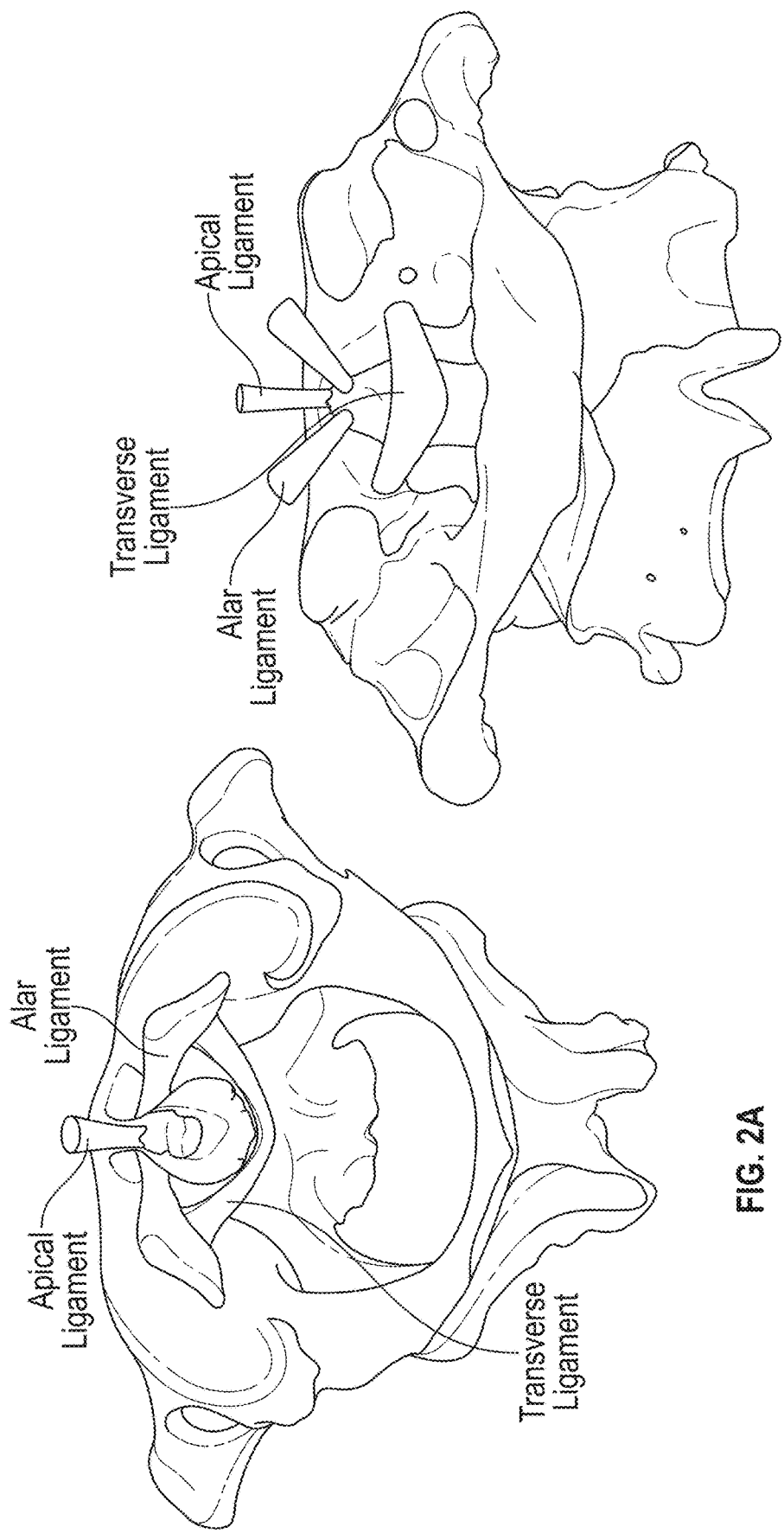
FIGS. 2A-2B and 3A-3C show different views of the C1-C2 joint anatomy.

Apical, alar, and transverse ligaments prevent excessive rotation, angulation and translation. Any laxity of ligaments can lead to abnormal mobility. FIGS. 2A and 2B schematically illustrates the apical, alar, and transverse ligaments of the C1-2 joint.

Figure 3A:
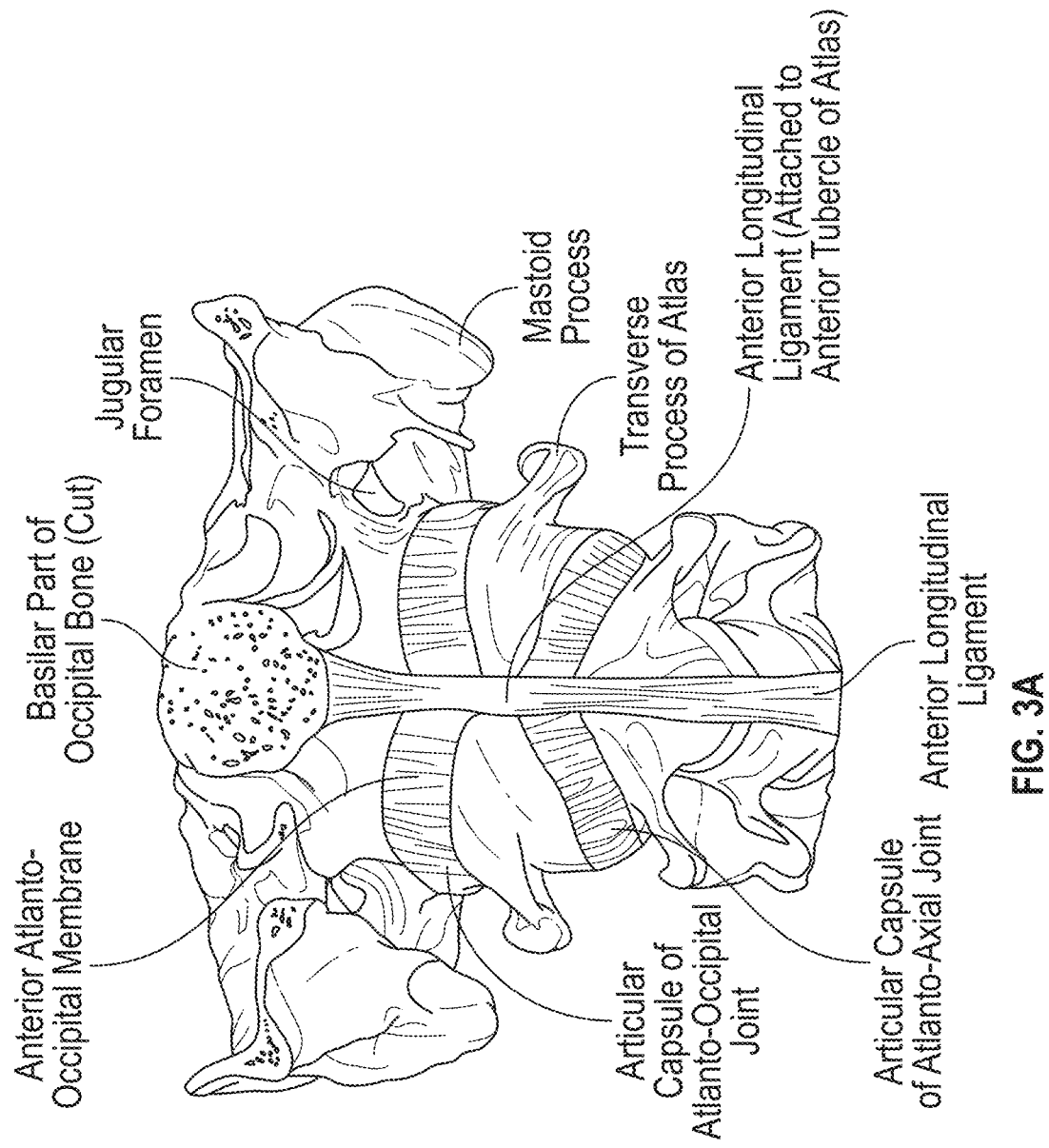
Figure 3B:
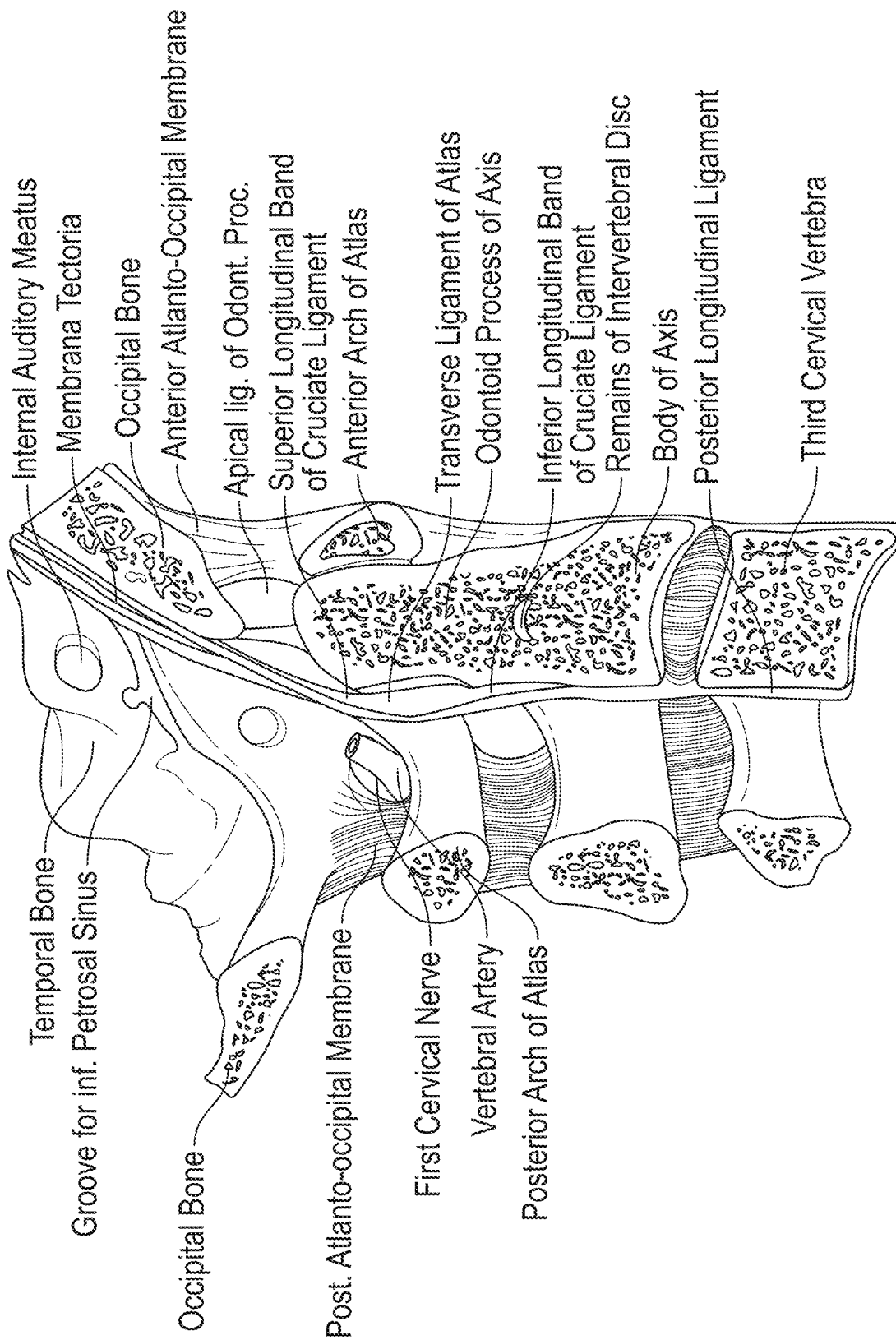
Figure 3C:
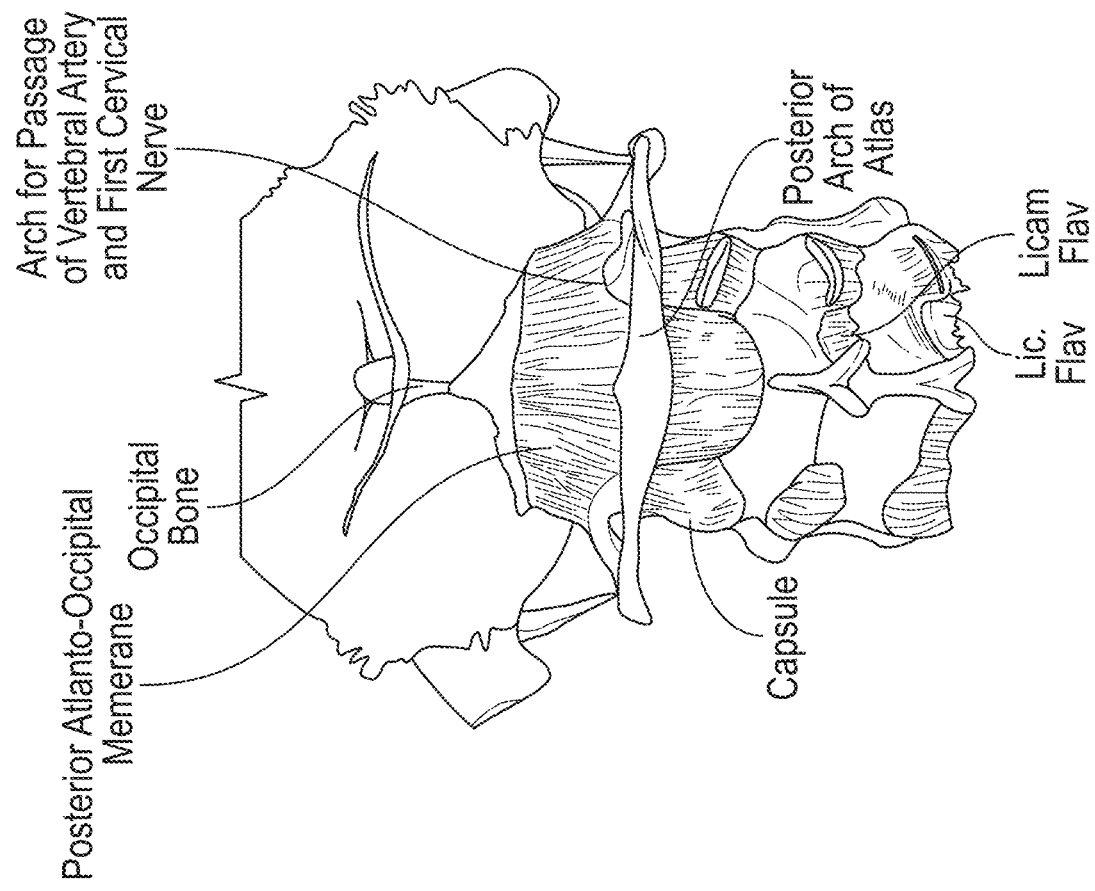
Figure 4B:
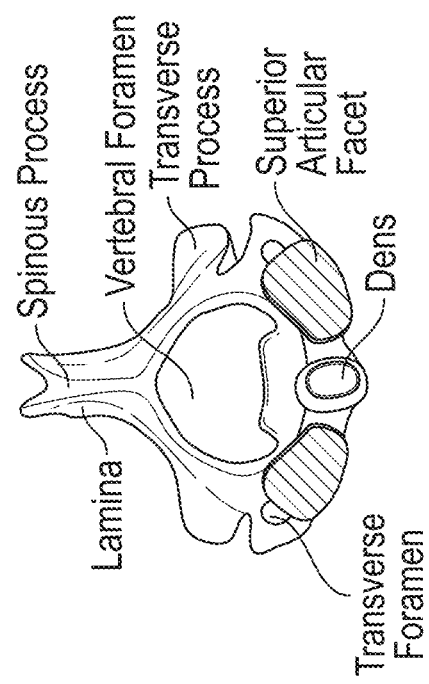
FIGS. 4A-4D schematically illustrates features of the atlanto-axial joint compared with other cervical joints.
Figure 4D:
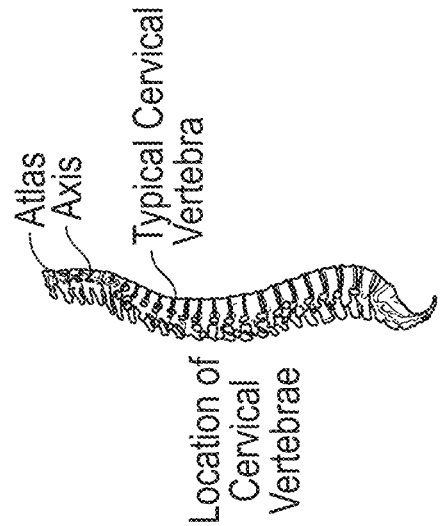
Figure 4A:
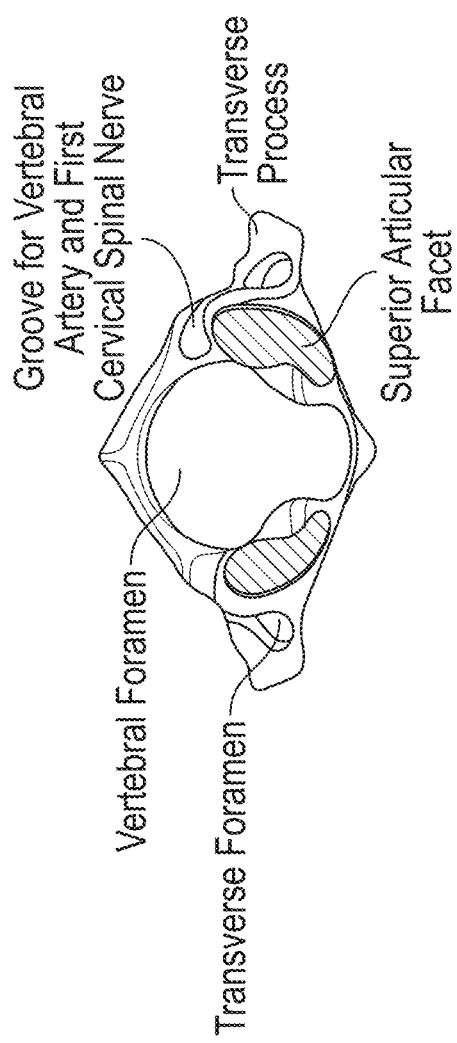
Figure 4C:
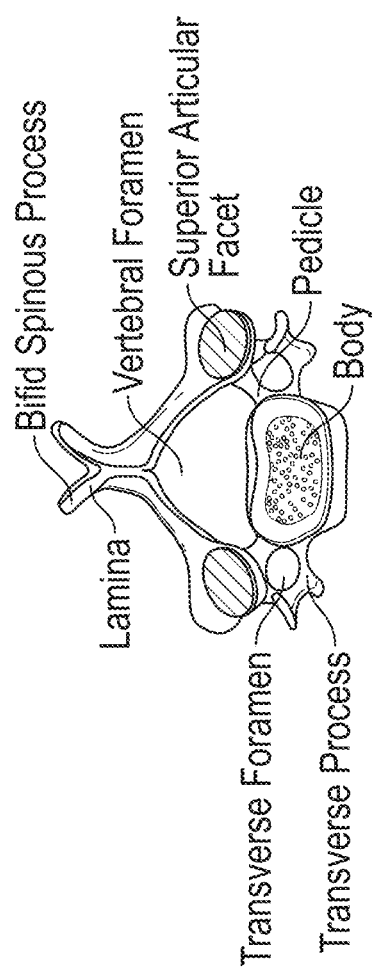

The capsular ligaments are thin and loose. They encompass the C1-2 articular facets and are lined with synovial membrane. Anteriorly, the two vertebra are connected by a continuation of the anterior longitudinal ligament. Posteriorly, the atlas and axis are joined by a thin membrane which is in series with the ligamenta flava. FIGS. 3A-3C further illustrate C1-2 ligamentous anatomy.

The joints exhibit six degrees of freedom of movement, the most being axial rotation. Other movements include lateral translation of about 3 mm, anteroposterior translation of about 3 mm, flexion-extension of between about 5-10 degrees, and a few millimeters (such as between about 2 mm to about 4 mm) of vertical movement of C2 within C1 coupled with rotation. The C1-C2 prostheses described herein are designed to mimic the aforementioned movement. FIGS. 4A-4D schematically illustrates features of the atlanto-axial joint compared with other cervical joints. Some embodiments of systems and methods preserve all six degrees of freedom of movement.

The kinematics of the C1-2 joint will now be described. On right rotation, the right facet of C1 glides in the posterior direction, and the left facet glides in the anterior direction. On left rotation, the opposite occurs.

During flexion, both facet surfaces of C1 roll anteriorly. The anterior arch of C1 glides in a caudal direction on the anterior surface of the dens. During extension, the opposite occurs. In some cases, the C1-2 joint cartilage converts the articular surfaces into convex on convex. In some embodiments, the prosthesis can be sized and configured for implantation within the C1-2 (atlantoaxial) joint, or other joints, including but not limited to C2-3, C3-4, C4-5, C5-6, C6-7, C7-T1, and other thoracic, lumbar, or sacral joints.

The prosthesis can be configured to be placed within an intervertebral joint, including but not limited to a cervical joint, such as the atlanto-axial joint. The prostheses may be placed on the facets and secured to a posterior facing side of the facet joint.

Figure 5:
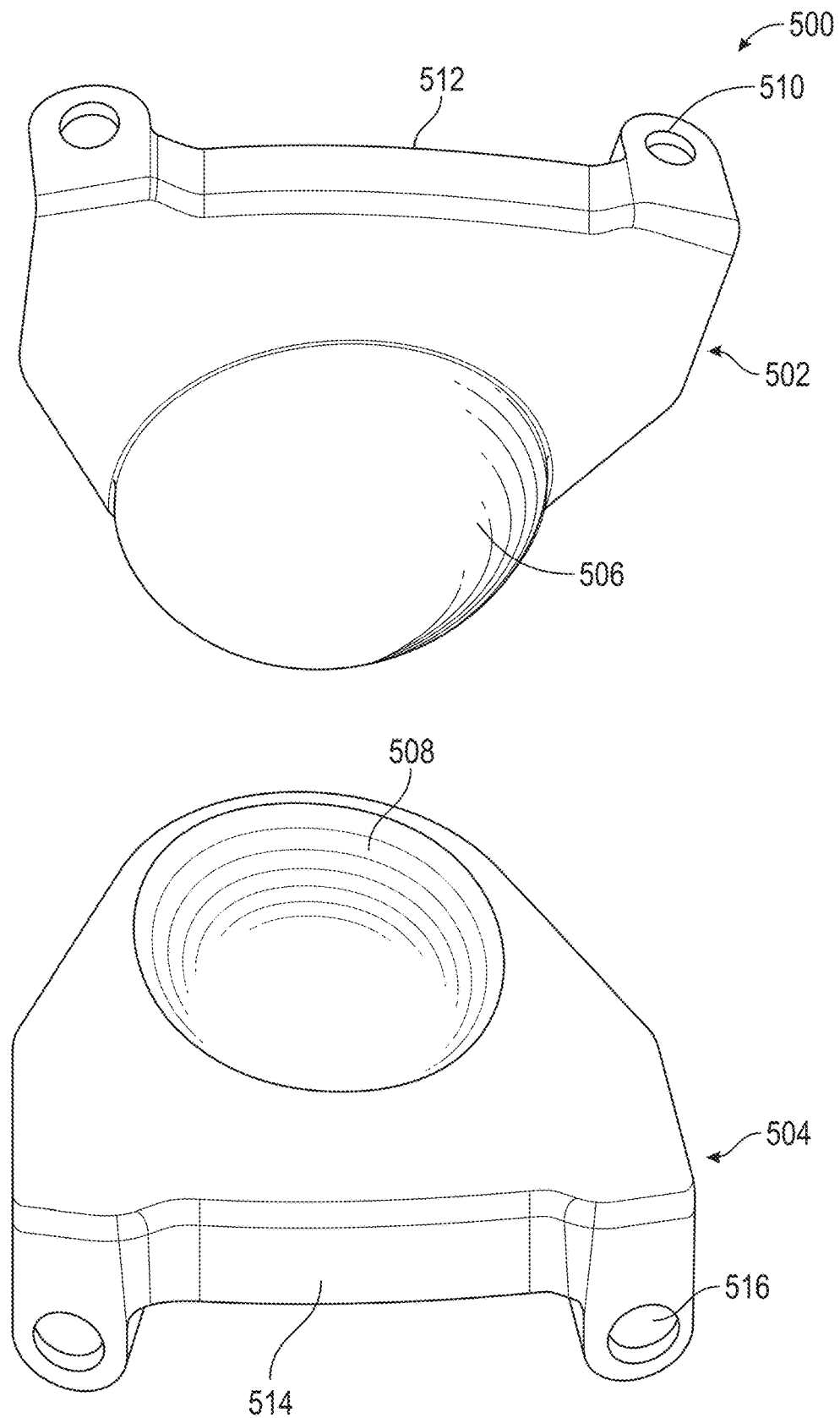
FIG. 5 illustrates an example of a joint prostheses that can be placed in the atlanto-axial joint.

As illustrated in FIG. 5, the prosthesis 500 can include a ball element 502 for placement in a first vertebrae (such as the C1 vertebrae for example), and a trough element 504 for placement in a second vertebrae directly adjacent to the first vertebrae (such as the C2 vertebrae for example). The ball element 502 can include a convex inferior surface 506 and a generally flat superior surface, as well as a generally superiorly-extending flange 512 including one or more apertures, for example two laterally-spaced apart apertures 510 configured to house bone screws therethrough to attach the ball element to a vertebrae, such as the C1 vertebrae. The convex inferior surface 506 can be substantially spherical, oval, oblong, or another shape in some cases. The trough element 504 can include a concave superior surface 508 configured to articulate with the convex inferior surface 506 of the ball element, and at least a portion of the perimeter of the surfaces 506, 508 can be proximate a posterior end of each respective component, in some embodiments. The trough element 504 can also include a generally flat inferior surface opposite the superior surface (not shown), as well as a generally inferiorly-extending flange 514 including one or more apertures, for example two laterally-spaced apart apertures 516 configured to house bone screws therethrough to attach the ball element 502 to a vertebrae, such as the C1 vertebrae, for example on a posterior facing side of the facet joint (see FIGS. 6A-6B). In some embodiments, the ball element 502 and the trough element 504 can have substantially the same diameter or radius. In some embodiments, the prosthesis or any element thereof can comprise a biocompatible material, such as a metal such as titanium, for example. In some embodiments, both the bearing surfaces of the ball element 502 and the socket element 504 may not exactly match. The ball element 502 and the trough element 504 may comprise the same material, for example both plastic or both metal, but in other configurations, may comprise different materials, for example one plastic element and one metal element.

FIG. 5A illustrates a top view of components of another embodiment of a ball-and-trough prosthesis 600 including a ball element 602 and a trough element 604 that can include any of the features of the other cervical joint prostheses described herein. The ball element 602 can include an arcuate, convex inferior surface 606 that can be, for example, as previously described, and at least partially forming an end (e.g., posterior end) of the ball element 602 as shown. The inferior surface 606 can have a circular or oval perimeter in some embodiments. The ball element 602 can have a length dimension 6BX and a width dimension 6DX. The inferior surface 606 of the ball element 602 can have a length dimension 6CX and a width dimension 6AX.

Also shown is trough element 604 including a concave superior surface 608 configured to articulate with the convex inferior surface 606 of the ball element 602. The concave superior surface 608 of the trough element 604 can have a length dimension 6FX and a width dimension 6EX, and be generally ovoid or ellipsoid in some cases. The trough element 604 can include a length dimension 6GX and a width dimension 6HX. The ball element 602 can also include a generally superiorly-extending flange 612 including laterally-spaced apart apertures 610 that can be as previous described. The trough element 604 can also include a generally inferiorly-extending flange 614 including laterally-spaced apart apertures 616 that can be as previously described.

In some embodiments, the width dimension 6AX can be, for example, between about 8 mm and about 12 mm, or about, at least about, or no more than about 5, 6, 7, 8, 9, 10, 11, 12, 13, 14, or 15 mm or more or less, including ranges encompassing any two of the foregoing values.

In some embodiments, the length dimension 6CX can be about the same as the width dimension 6AX, for example, between about 8 mm and about 12 mm, or about, at least about, or no more than about 5, 6, 7, 8, 9, 10, 11, 12, 13, 14, or 15 mm or more or less, including ranges encompassing any two of the foregoing values. As illustrated, the ball element 602 is generally circular, but the length dimension 6CX could be greater than the width dimension 6AX, giving the ball element 602 a more oval perimeter (see FIG. 5E).

In some embodiments, the length dimension 6BX can be, for example, between about 13 mm and about 20 mm, or about, at least about, or no more than about 10, 11, 12, 13, 14, 15, 16, 17, 18, 19, 20, 21, 22, 23, 24, 25 mm or more or less, including ranges encompassing any two of the foregoing values.

In some embodiments, the width dimension 6DX can be, for example, between about 13 mm and about 20 mm, or about, at least about, or no more than about 10, 11, 12, 13, 14, 15, 16, 17, 18, 19, 20, 21, 22, 23, 24, 25 mm or more or less, including ranges encompassing any two of the foregoing values.

In some embodiments, the width dimension 6EX can be, for example, between about 8 mm and about 12 mm, or about, at least about, or no more than about 5, 6, 7, 8, 9, 10, 11, 12, 13, 14, or 15 mm or more or less, including ranges encompassing any two of the foregoing values. The width dimension 6EX may be greater than or equal to the width dimension 6AX. For example, the width dimension 6EX may be greater than the width dimension 6AX to permit translational movement in the lateral direction.

In some embodiments, the length dimension 6FX can be the same or greater than the width dimension 6EX, for example, between about 8 mm and about 12 mm, or about, at least about, or no more than about 5, 6, 7, 8, 9, 10, 11, 12, 13, 14, or 15 mm or more or less, including ranges encompassing any two of the foregoing values. The length dimension 6FX may be greater than the length dimension 6CX to permit anteroposterior translational movement between the ball element 602 and trough element 604.

In some embodiments, the length dimension 6GX can be about the same as the length dimension 6BX, for example, between about 13 mm and about 20 mm, or about, at least about, or no more than about 10, 11, 12, 13, 14, 15, 16, 17, 18, 19, 20, 21, 22, 23, 24, 25 mm or more or less, including ranges encompassing any two of the foregoing values.

In some embodiments, the width dimension 6HX can be about the same as the width dimension 6DX, for example, between about 13 mm and about 20 mm, or about, at least about, or no more than about 10, 11, 12, 13, 14, 15, 16, 17, 18, 19, 20, 21, 22, 23, 24, 25 mm or more or less, including ranges encompassing any two of the foregoing values.

Figure 5B:
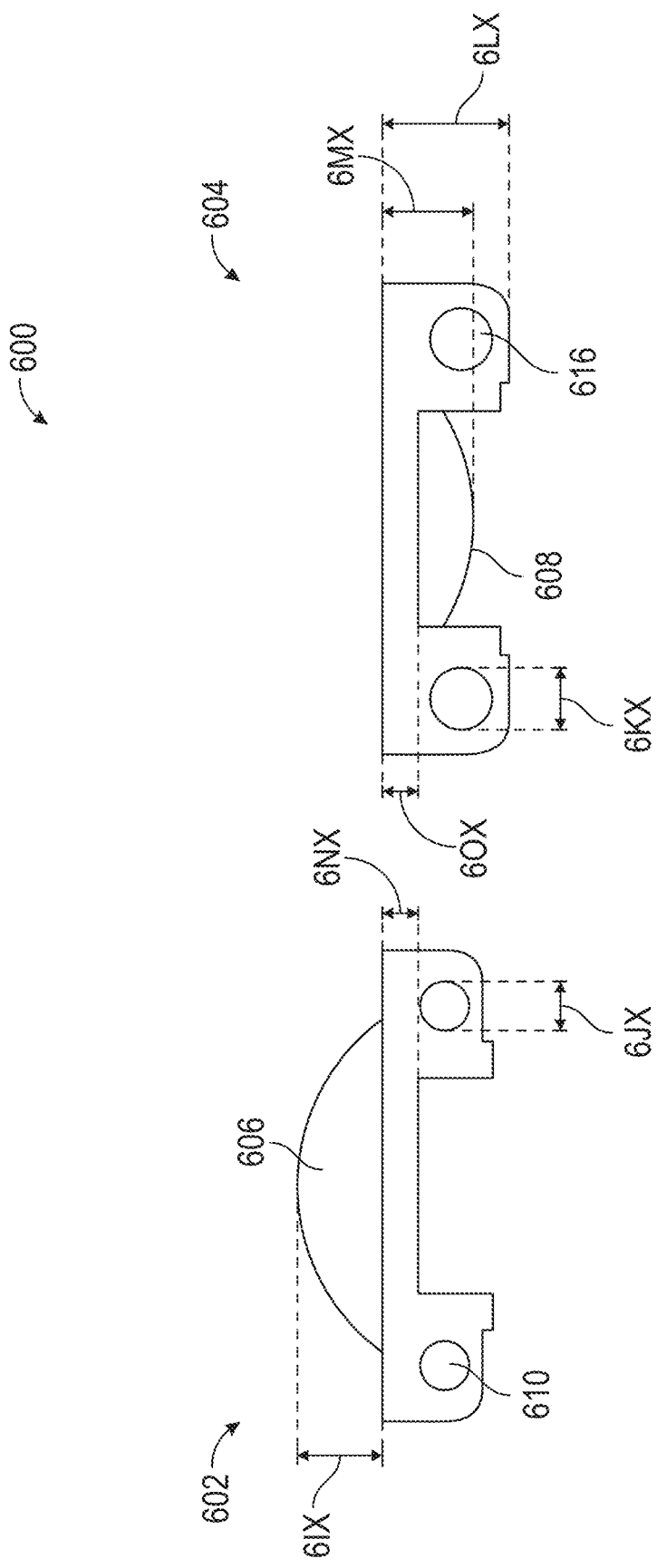

FIG. 5B illustrates a posterior end view of components of the ball-and-trough prosthesis 600 of FIG. 5A including the ball element 602 with flange 612 and apertures 610 and trough element 604 with flange 614 and apertures 616 that can be as previously described. The arcuate, convex inferior surface 606 of the ball element 602 can have a depth dimension 6IX. Apertures 610 can have a diameter 6JX. The flange 612 can have a thickness dimension 6NX.

In some embodiments, the depth dimension 6IX can be, for example, between about 1 mm and about 5 mm, or about, at least about, or no more than about 1, 1.5, 2, 2.1, 2.2, 2.3, 2.4, 2.5, 2.6, 2.7, 2.8, 2.9, 3, 3.5, 4 mm or more or less, including ranges encompassing any two of the foregoing values.

In some embodiments, the diameter 6JX can be, for example, between about 1 mm and about 2 mm, or about, at least about, or no more than about 1.0, 1.1, 1.2, 1.3, 1.4, 1.5, 1.6, 1.7, 1.8, 1.9, 2.0 mm or more or less, including ranges encompassing any two of the foregoing values.

In some embodiments, the thickness dimension 6NX can be, for example, between about 0.5 mm and about 2 mm, or about, at least about, or no more than about 0.5, 0.6, 0.7, 0.8, 0.9, 1.0, 1.1, 1.2, 1.3, 1.4, 1.5, 1.6, 1.7, 1.8, 1.9, 2.0 mm or more or less, including ranges encompassing any two of the foregoing values.

Still referring to FIG. 5B, the concave superior surface 608 of the trough element 604 can have a depth dimension 6MX. The apertures 616 can have a diameter 6KX. The flange 614 can have a thickness dimension 6OX. The trough element 604 can have a maximum thickness 6LX.

In some embodiments, the depth dimension 6MX can be, for example, between about 1 cm and about 5 cm, or about, at least about, or no more than about 1, 1.5, 2, 2.1, 2.2, 2.3, 2.4, 2.5, 2.6, 2.7, 2.8, 2.9, 3, 3.5, 4 mm or more or less, including ranges encompassing any two of the foregoing values. The depth dimension may be greater than, equal to, or less than the height 6IX of the convex surface 606 depending on the desired tilt.

In some embodiments, the diameter 6KX can be, for example, between about 1 mm and about 2 mm, or about, at least about, or no more than about 1.0, 1.1, 1.2, 1.3, 1.4, 1.5, 1.6, 1.7, 1.8, 1.9, 2.0 mm or more or less, including ranges encompassing any two of the foregoing values.

In some embodiments, the depth dimension 6LX can be, for example, between about 2 mm and about 6 mm, or about, at least about, or no more than about 2, 2.5, 3, 3.1, 3.2, 3.3, 3.4, 3.5, 3.6, 3.7, 3.8, 3.9, 4, 4.5, 5, 6 mm or more or less, including ranges encompassing any two of the foregoing values.

In some embodiments, the thickness dimension 6OX can be, for example, between about 0.5 mm and about 2 mm, or about, at least about, or no more than about 0.5, 0.6, 0.7, 0.8, 0.9, 1.0, 1.1, 1.2, 1.3, 1.4, 1.5, 1.6, 1.7, 1.8, 1.9, 2.0 mm or more or less, including ranges encompassing any two of the foregoing values.

Figure 5C:
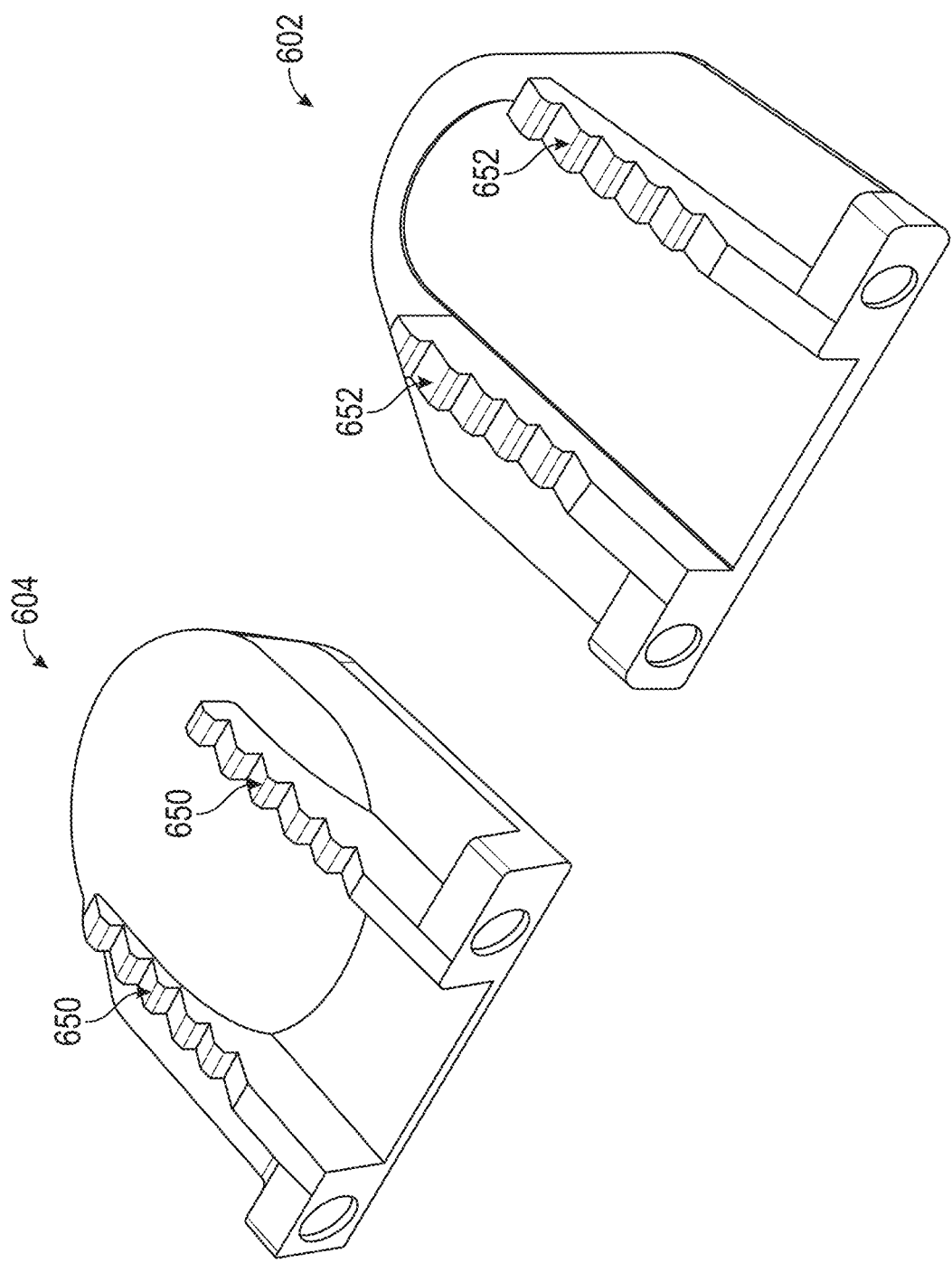

FIG. 5C illustrates a view of anchoring surfaces of the components of the ball-and-trough prosthesis 600 of FIGS. 5A-5B, which may have one or more anchoring elements 652, 650 along at least a partial length of the ball element 602 and/or trough element 604. For example, FIG. 5C illustrates a plurality of anchoring elements 650, 652 in a linear array spaced apart from the axial and/or longitudinal midline of each of the trough element 604 and ball element 602 components, respectively. The anchoring elements 650, 652 can include areas of increased surface area, such as keels with sawtooth patterns as illustrated in some embodiments that can be positioned parallel to the major axis, parallel to the minor axis, or oblique to the major or minor axis of each of the ball element 602 or the trough element 604 in some embodiments. As illustrated, anchoring elements 650, 652 extend along a majority of a length of the ball element 602 and the trough element 604, but the sawtooth patterns do not extend the length of anchoring elements 650, 652. For example, the sawtooth patterns may be present generally in the areas opposite the convex inferior surface 606 and the concave superior surface 608. The anchoring elements 650, 652 maybe positioned sufficiently inward such that the sawtooth pattern is inward of a periphery of the ball and trough features. The anchoring elements 650, 652 can be configured to promote or inhibit bony ingrowth in some cases.

Figure 5D:
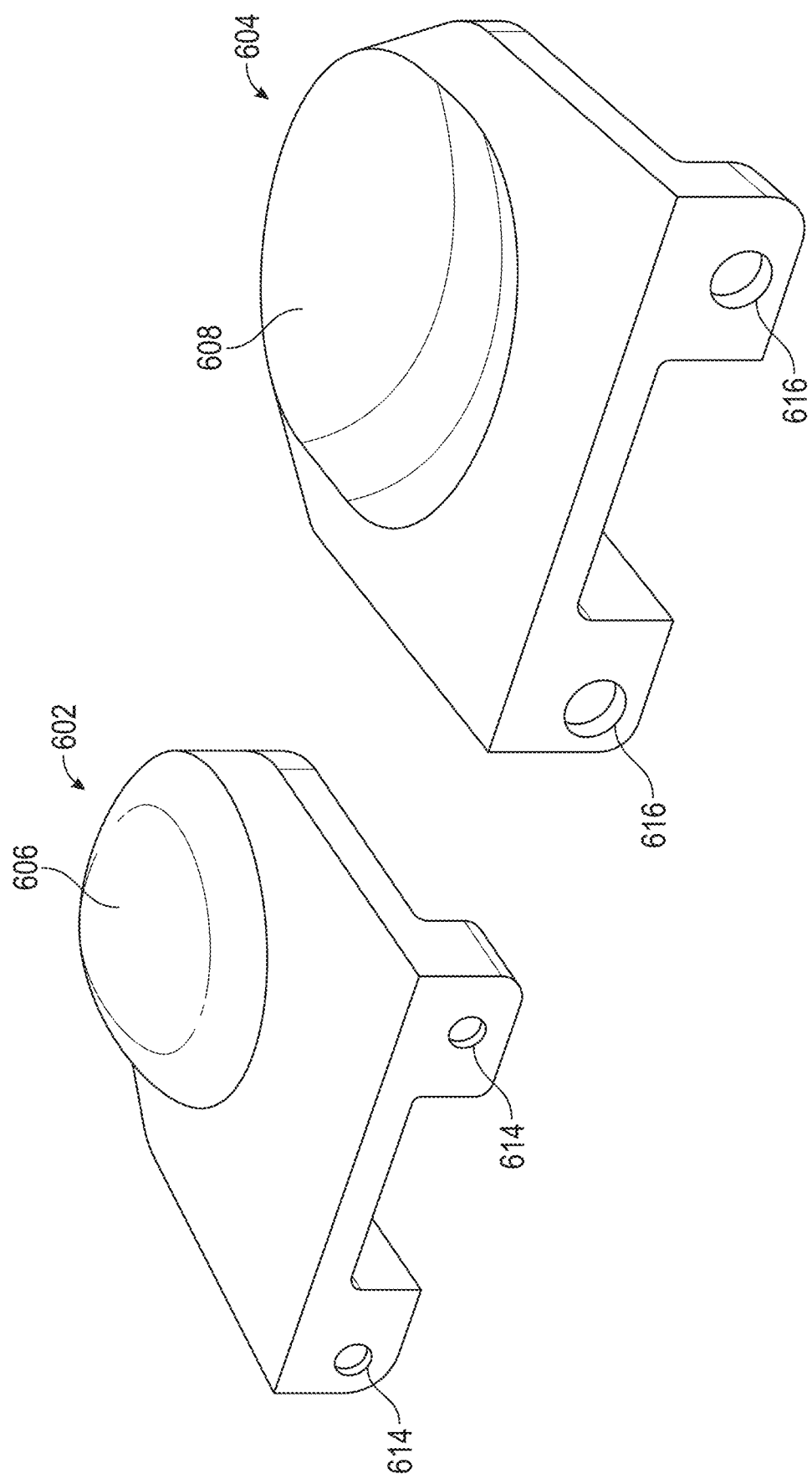
Figure 5F:
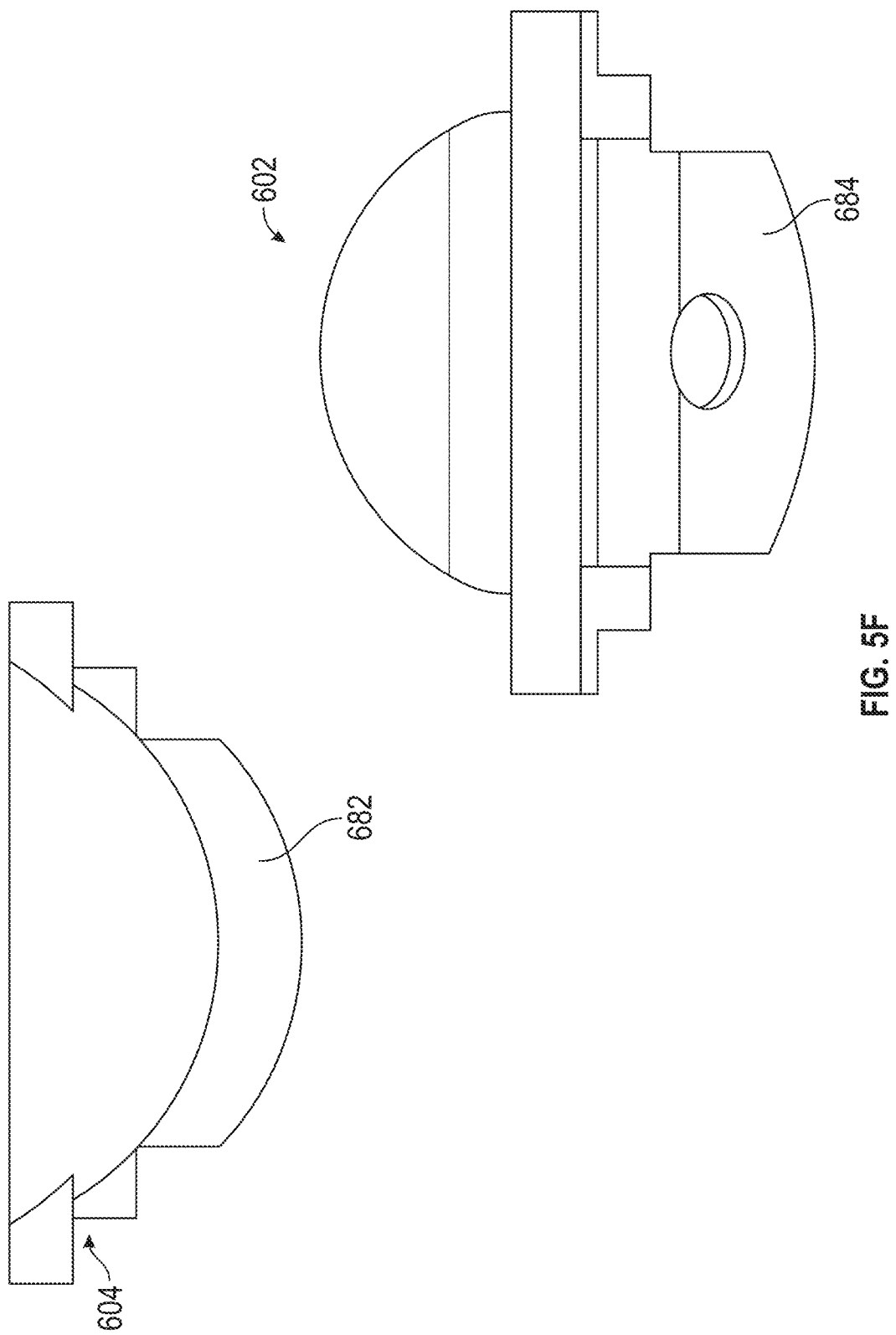
Figure 5G:
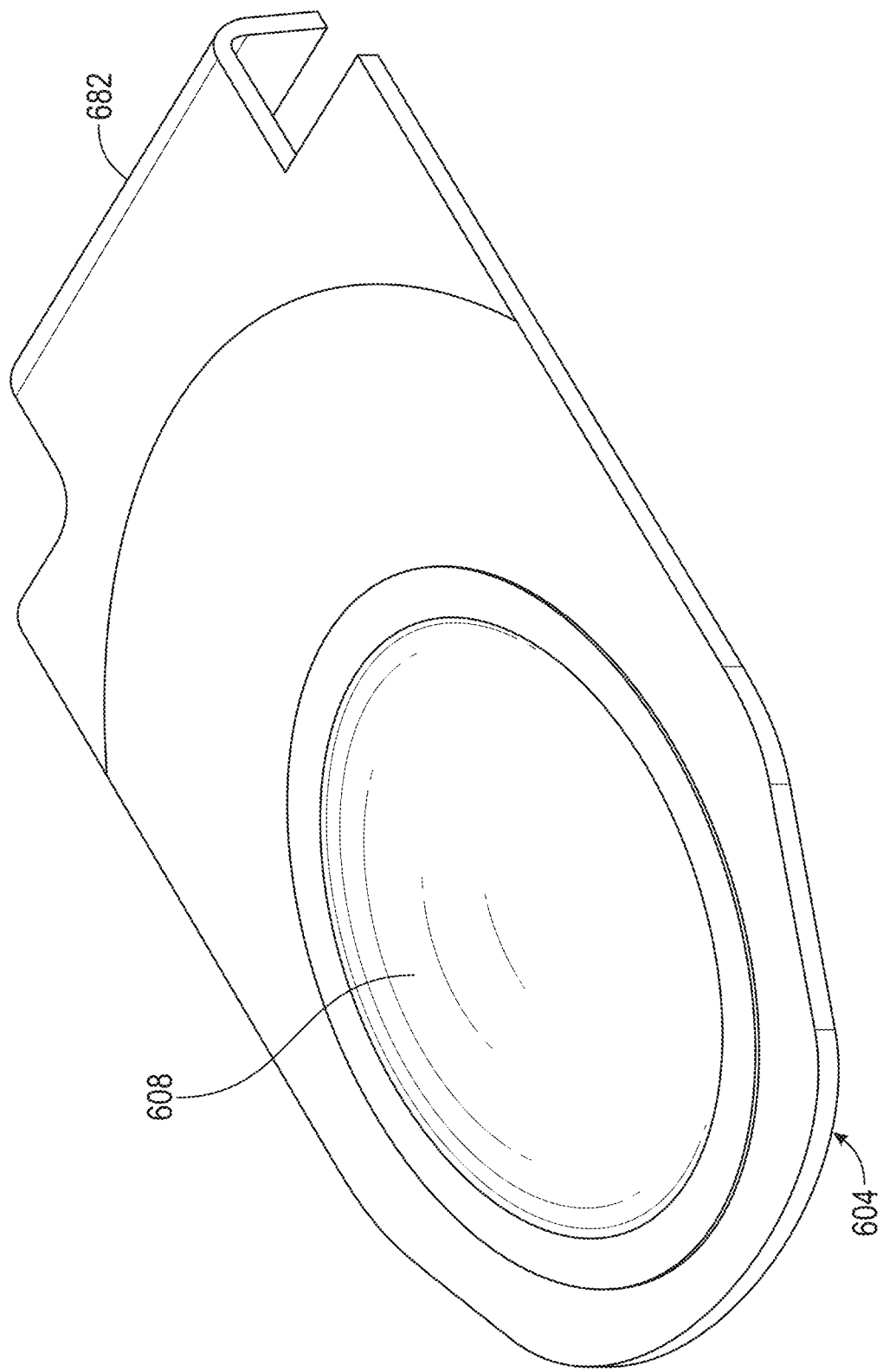
Figure 5H:
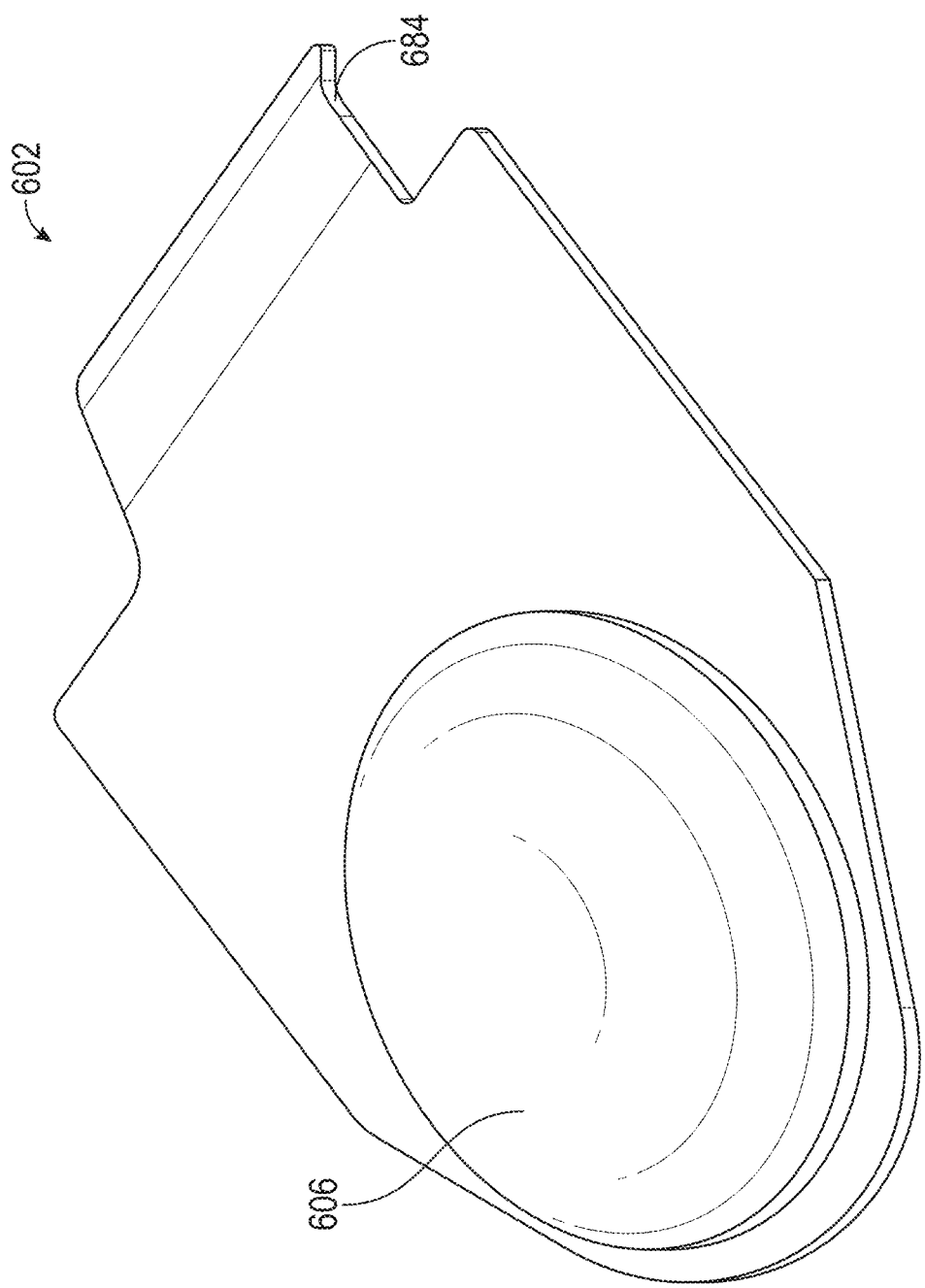

FIG. 5D illustrates a view of articulating surfaces opposite those shown in FIG. 5C of the components of the ball-and-trough prosthesis of FIGS. 5A-5B.

FIGS. 5E-5H illustrate additional embodiments of a ball-and-trough prosthesis 680 that can include any number of features of the prosthesis of FIGS. 5A-5D for example, with a posterior extension of flanges 682, 684 of the ball element 602 and the trough element 604 respectively that curve in a superior or inferior direction as shown, and that can include one or more anchoring apertures. Unlike the prosthesis 600, each component 602, 604 of the prosthesis 680 only includes a single flange 682, 684 with a single anchoring aperture. In contrast to the anchoring elements 650, 652 shown in FIG. 5C, the anchoring elements 650, 652 in the prosthesis 680 approach region opposite the convex inferior surface 606 and concave superior surface 608 (see FIGS. 5M and 5N compared to FIG. 5C), but are not positioned inward of a periphery of the convex inferior surface 606 and concave superior surface 608.

Figure 5I:
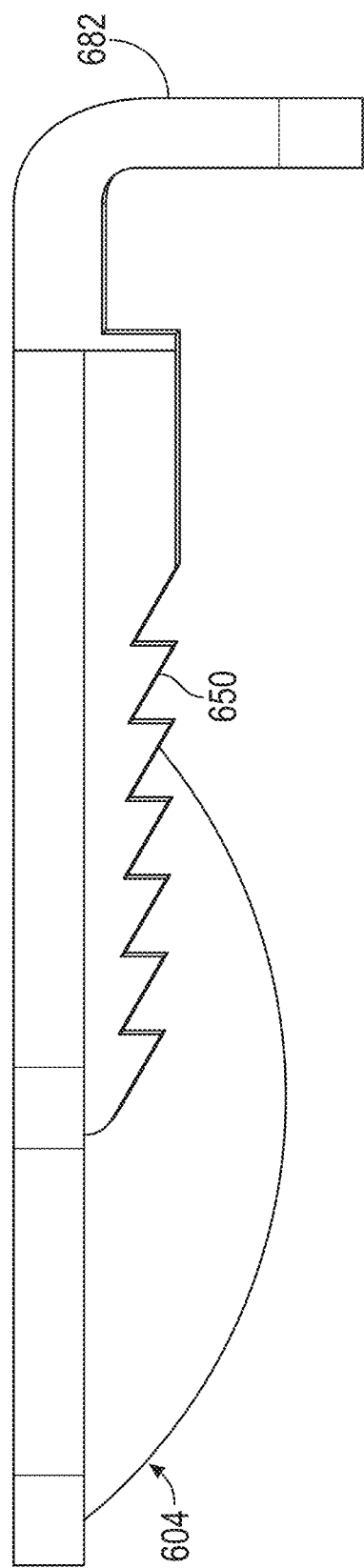
Figure 5J:
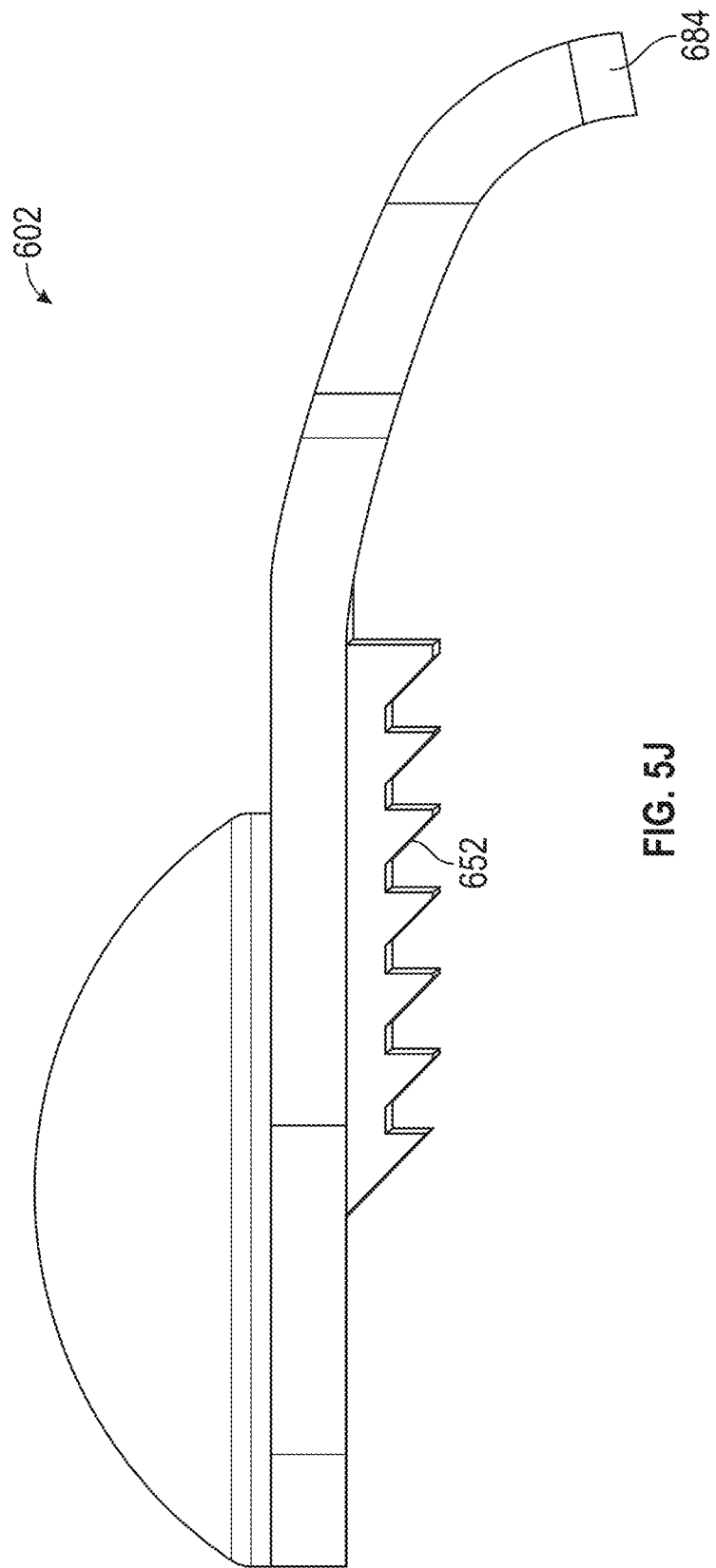
Figure 5K:
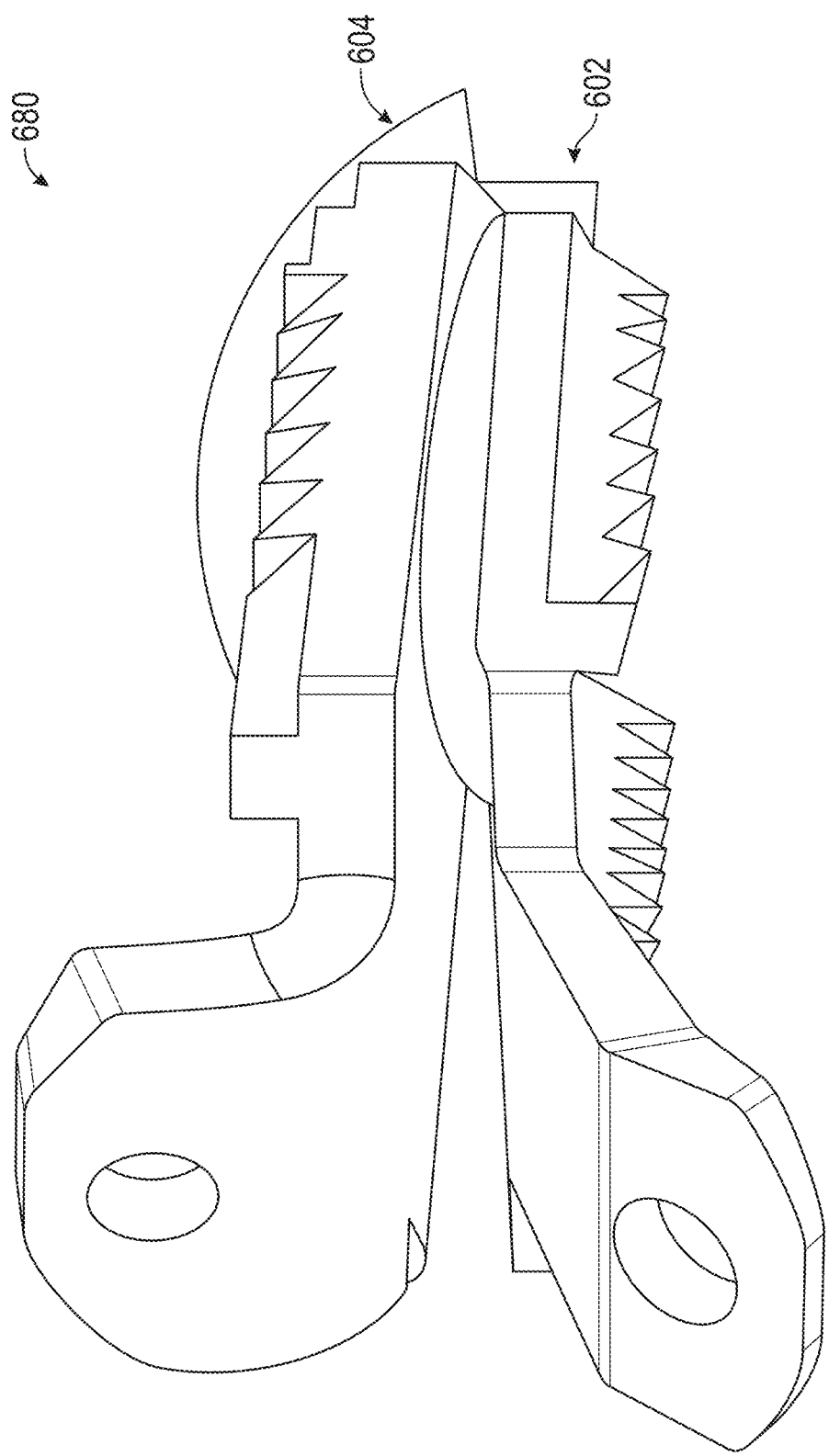
Figure 5L:
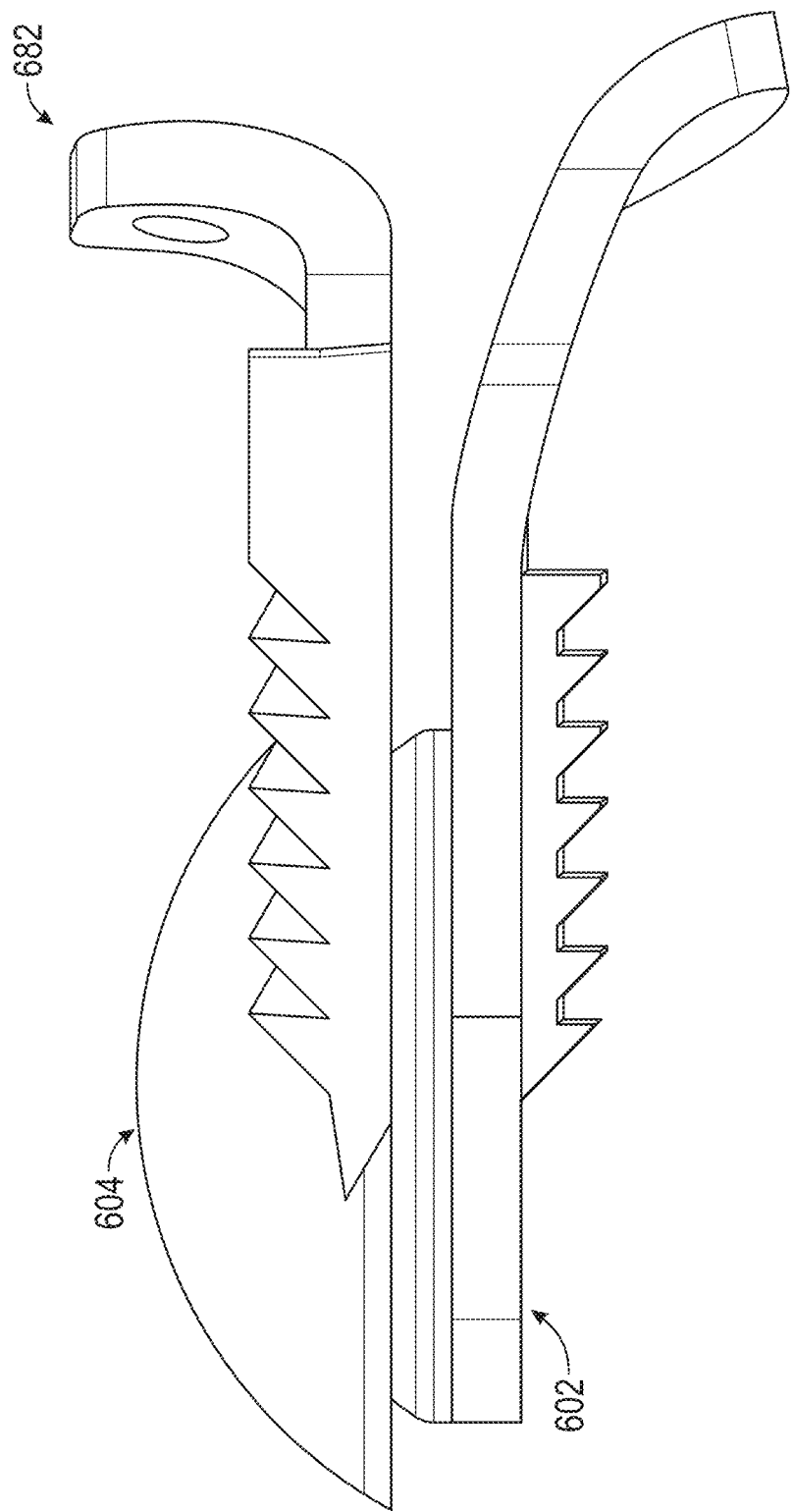
Figure 5N:
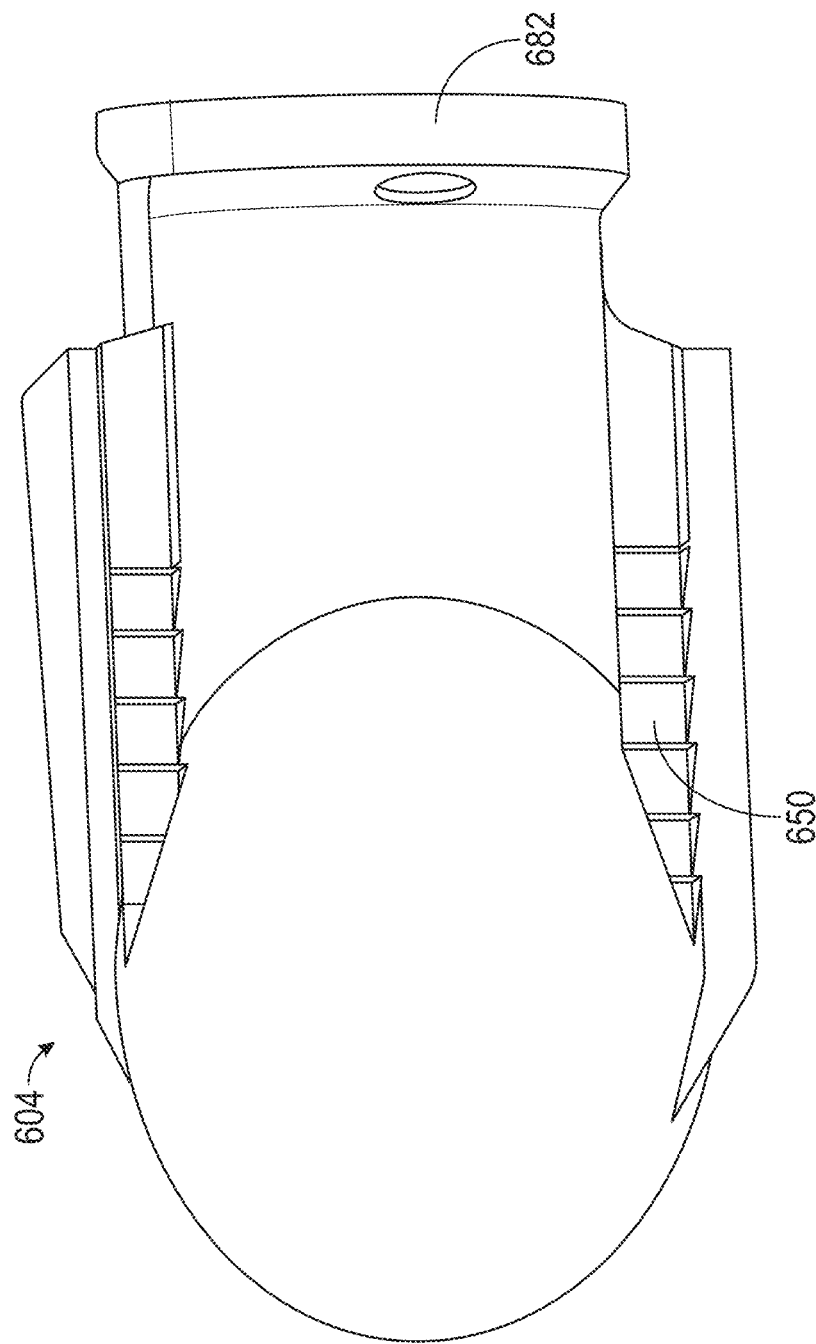
Figure 50:
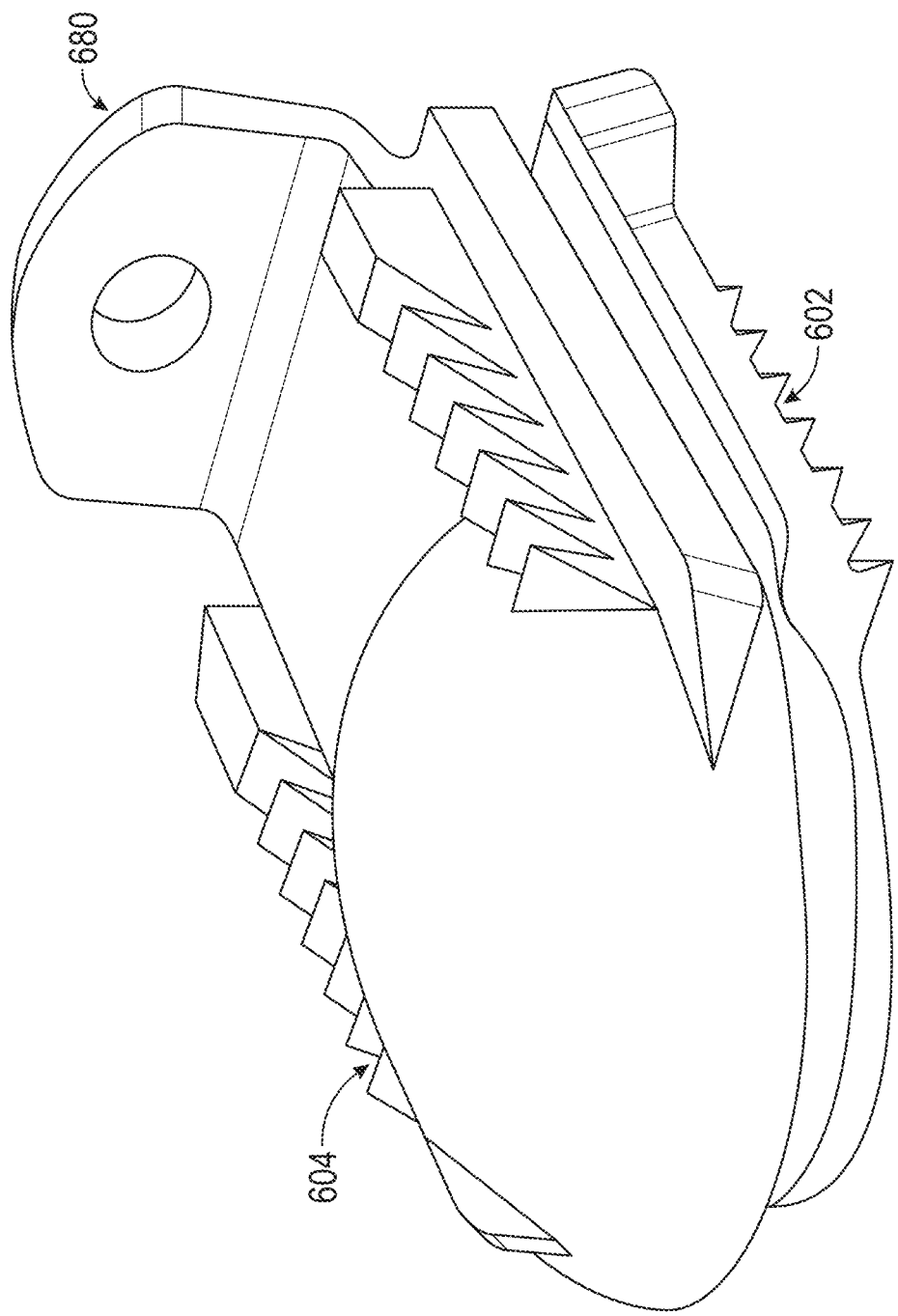

FIGS. 5I and 5J illustrate additional views of components of the ball-and-trough prosthesis of FIGS. 5E-5H showing anchoring elements 650, 652.

FIGS. 5K-5O illustrate further additional views of the ball-and-trough prosthesis 680 of FIGS. 5E-5J, with the ball element 602 mated with the trough element 604 to form an artificial joint prosthesis.

Figure 5P:
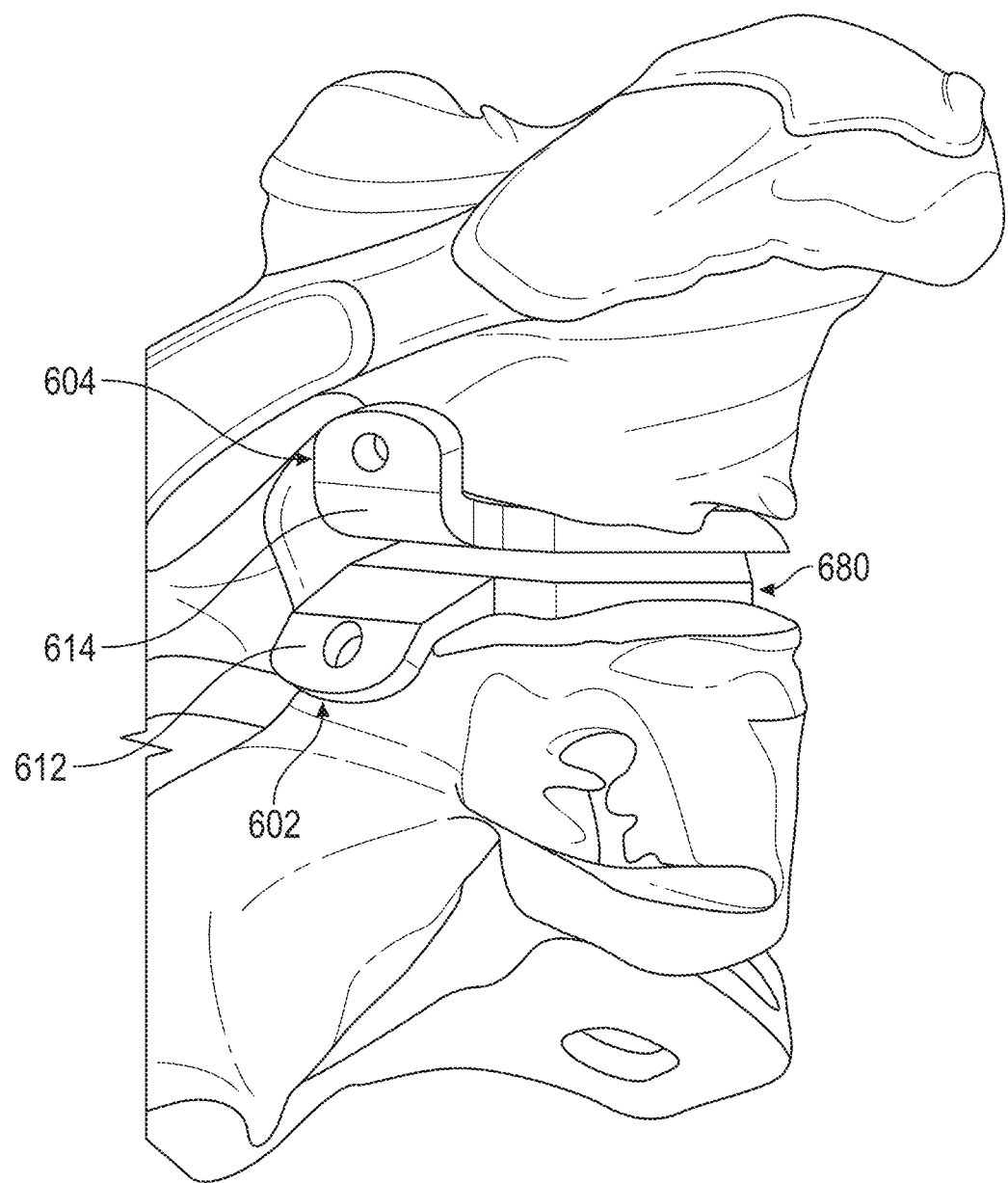
Figure 5Q:
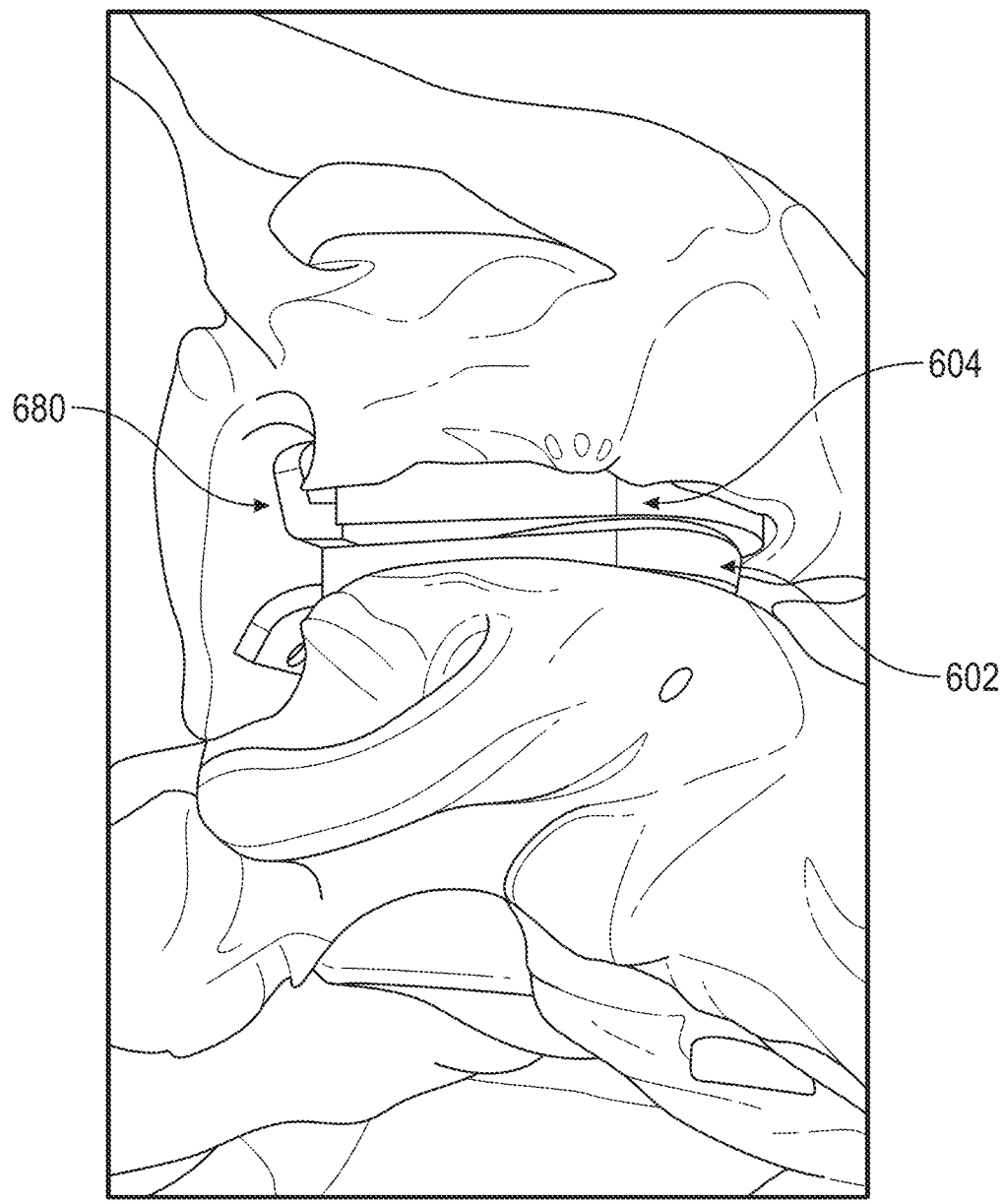

FIGS. 5P-5Q illustrates views of the joint prosthesis 680 of FIGS. 5E-5O installed within the atlanto-axial joint. As illustrated, each of the ball element 602 and the trough element 604 of the prosthesis 680 are attached to a posterior facing side of the facet joint. The flanges 612, 614 may be differently shaped and contoured to bend about a rim of the respective vertebrae. Each flange 612, 614 may receive a bone screw or other fastener to secure the prostheses to the vertebrae.

Figure 6B:
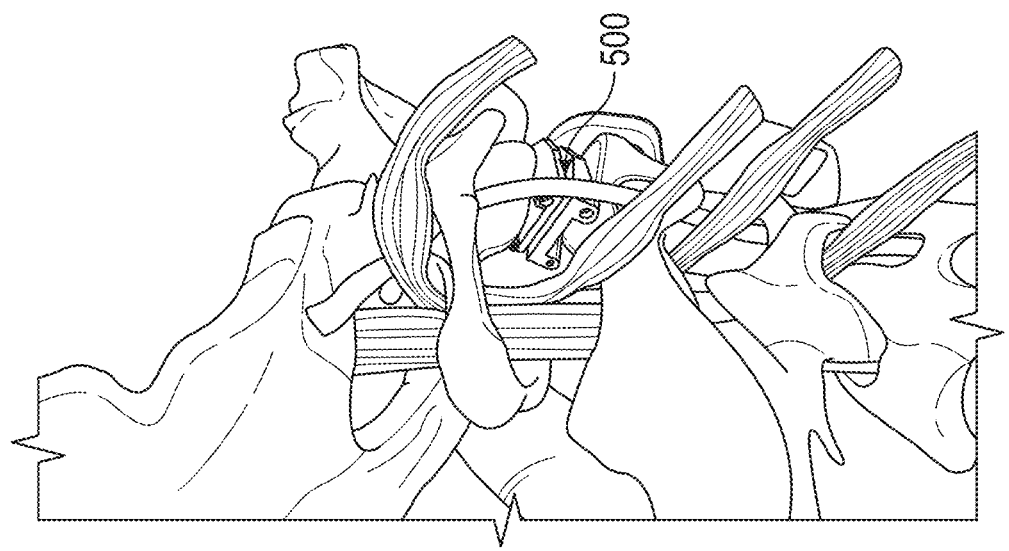
FIGS. 6A-6B illustrate the joint prosthesis shown in FIG. 5 placed in the atlanto-axial joint.
Figure 6A:
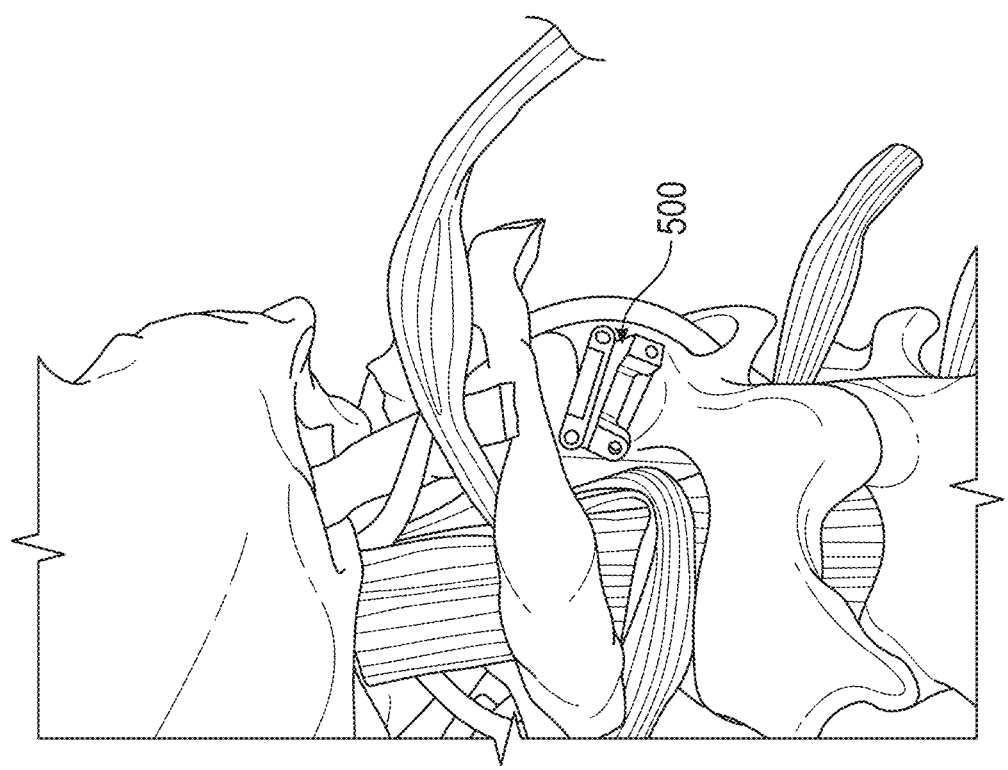

FIGS. 6A-6B illustrates schematically a ball-and-trough joint replacement prosthesis 500 placed in the atlanto-axial joint. As illustrated, each of the ball element and the trough element of the prosthesis 500 are attached to a posterior facing side of the facet joint.

Figure 7A:
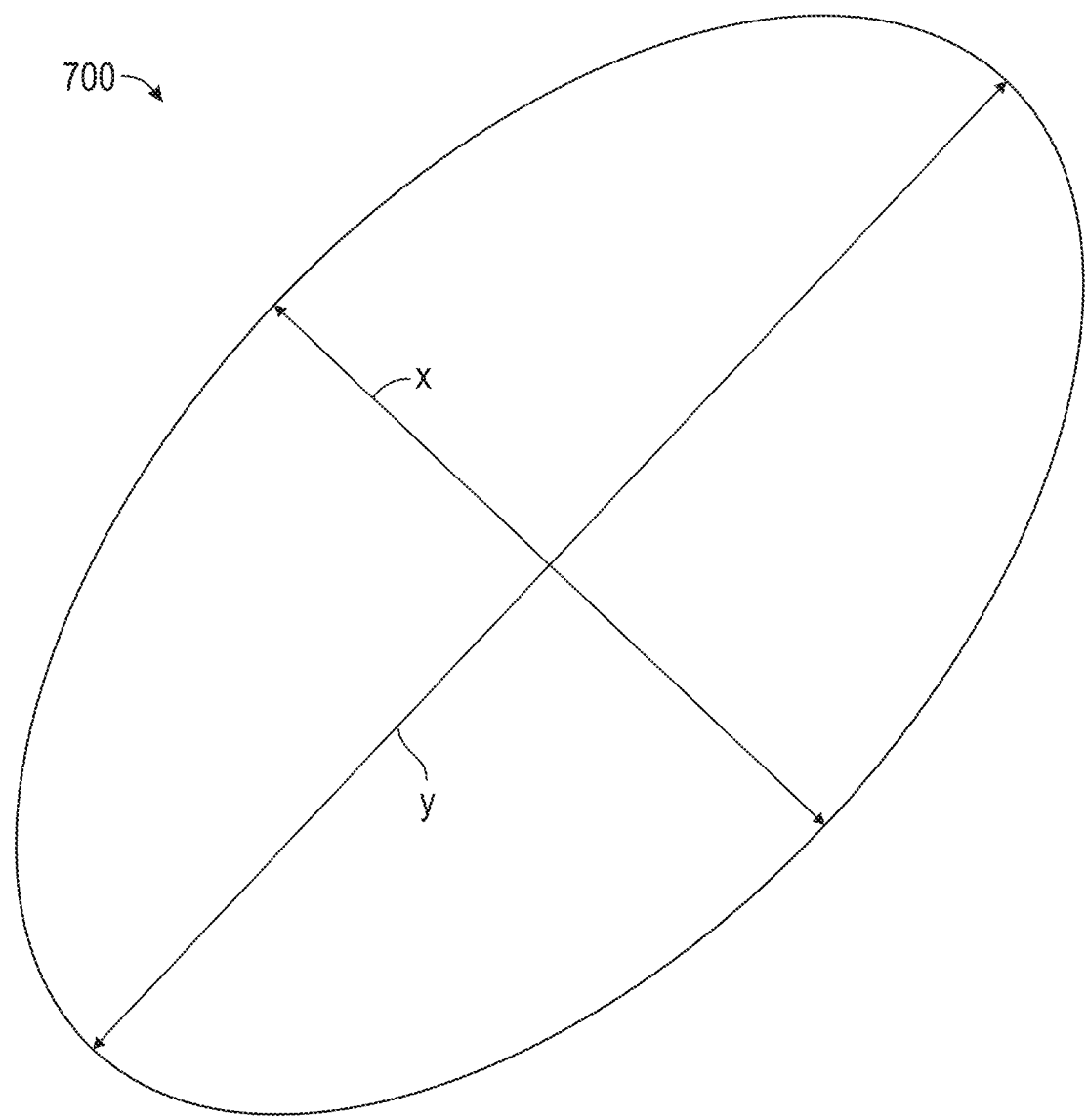
FIG. 7A illustrates a footprint of a joint prosthesis that can be placed in the atlanto-axial joint.

FIG. 7A illustrates schematically a footprint of an intervertebral joint prosthesis 700 that can be combined with any of the features of the C1-C2 joint prostheses described herein. In some embodiments, the prosthesis can be configured to be placed within an intervertebral joint, including but not limited to a cervical joint, such as the atlanto-axial joint. In some embodiments, the prosthesis can include a generally ovoid, or ellipsoid cross-sectional geometry. The prosthesis can include a major axis dimension y of, for example, between about 12 mm and about 22 mm, such as about 12, 13, 14, 15, 16, 17, 18, 19, 20, 21, or 22 mm, or ranges including any two of the foregoing values. The prosthesis can also include a minor axis dimension x of, for example, between about 10 mm and about 20 mm, such as between about 10, 11, 12, 13, 14, 15, 16, 17, 18, 19, or 20 mm, or ranges including any two of the foregoing values. In some embodiments, the major axis dimension y is about, at least about, or no more than about 1.25×, 1.2×, 1.19×, 1.18×, 1.17×, 1.16×, 1.15×, 1.14×, 1.13×, 1.12×, 1.11× 1.1×, 1.09×, 1.08×, 1.07×, 1.06×, 1.05×, 1.04×, 1.03×, 1.02×, 1.01×, or more or less of the minor axis dimension x, including ranges including any two of the foregoing values.

Figure 7B:
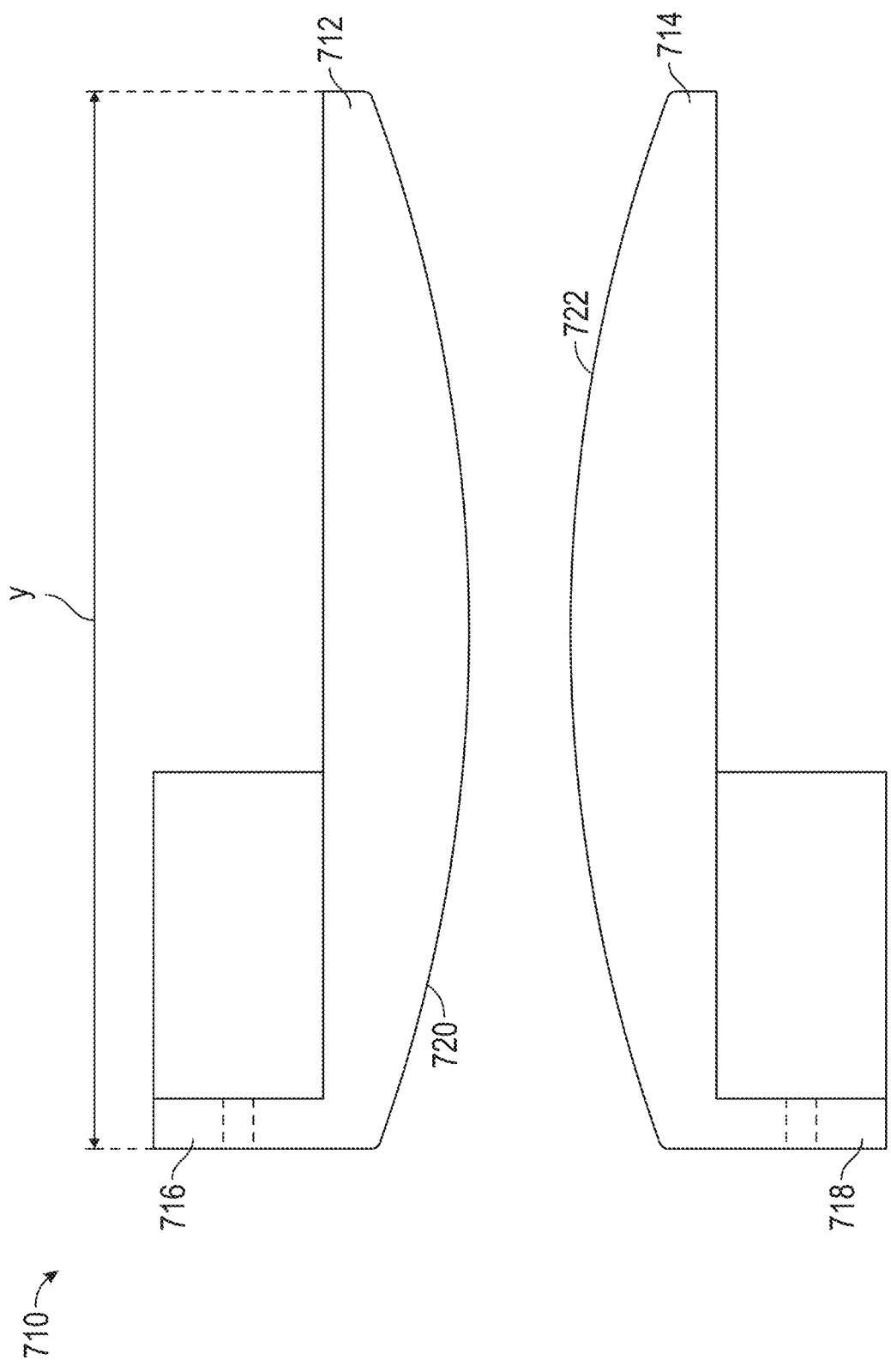
FIGS. 7B and 7C illustrates schematically a joint prosthesis that can be placed in the atlanto-axial joint.
Figure 7C:
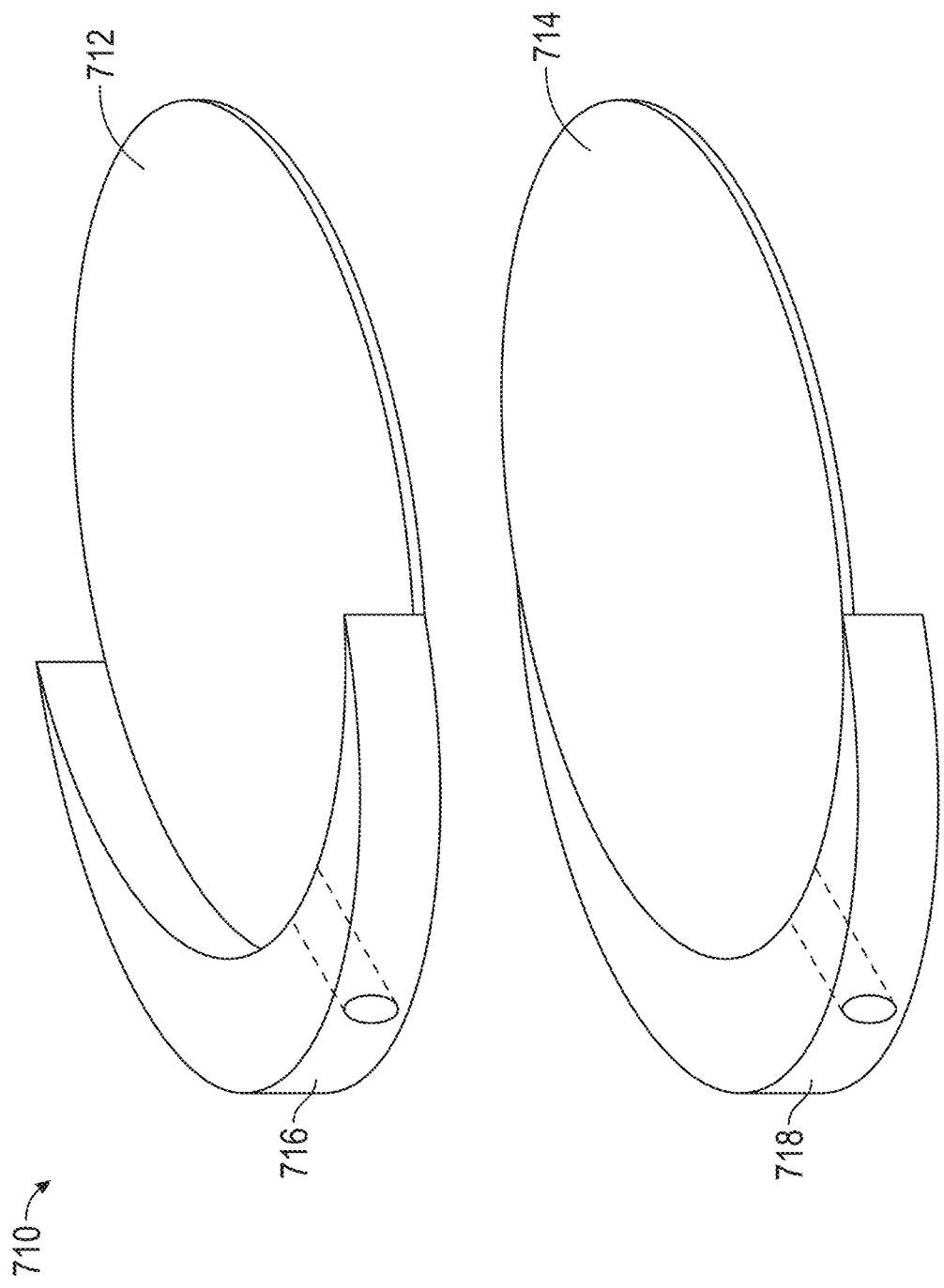

FIG. 7B illustrates schematically a side view of an embodiment of a joint replacement prosthesis 710 (e.g., cervical vertebral joint replacement prosthesis, such as at C1-2 for example), including a first superior component 712 configured to attach to a first vertebrae, and a second inferior component 714 configured to attach to a second vertebrae. The prosthesis can include a bi-convex design, with both the first component 712 and the second component 714 including convex articulating surfaces 720, 722. In some embodiments, the convex surfaces 720, 722 of the respective first and second components 712, 714 can have the same or substantially matching radii of curvature. Each component 712, 714 of the prosthesis 710 can include dimensions similar to the joint prosthesis 700. The first component and the second component can include flanges 716, 718 configured for attachment to respective vertebrae, which can include any number of features described elsewhere herein. As in FIG. 7C, the flanges 716, 718 can be generally curved, and in some cases configured to mimic the rounded surface/geometry of articular pillars of vertebrae, including at C1 and C2. Each flange 716, 718 can include at least one aperture for receiving a screw to secure the components 712, 714 to the respective vertebrae.

Figure 8:
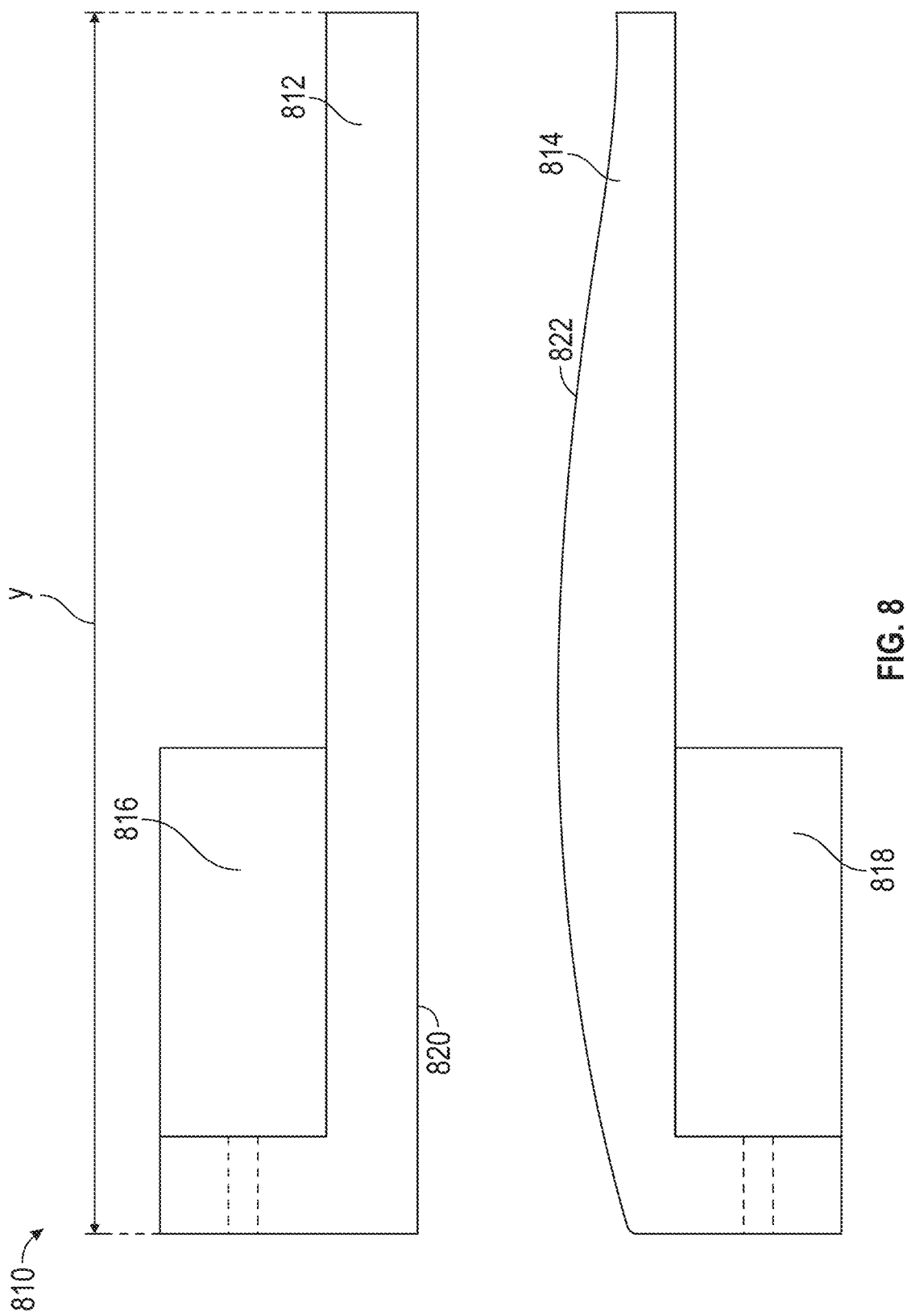
FIG. 8 illustrates schematically another joint prosthesis that can be placed in the atlanto-axial joint.

FIG. 8 illustrates schematically a side view of another embodiment of a joint replacement prosthesis 810, including a first superior component 812 configured to attach to a first vertebrae, and a second inferior component 814 configured to attach to a second vertebrae. The prosthesis 810 can include features as described elsewhere herein, and in some cases the first, superior component 812 includes a generally flat articulating surface 820, while the second, inferior component 814 also includes a generally convex articulating surface 822.

In some embodiments, a vertebral joint replacement prosthesis, (e.g., cervical vertebral joint replacement prosthesis, such as at C1-2 for example) as described anywhere herein, can include any number of the following features:

A keel or coating with, for example, hydroxyapatite (e.g., nano-sized or micro-sized) and/or other osteoinductive materials to integrate with bone.

The curved fixation flange can be configured to minimize the impact on either vertebral artery or canal.

The prosthesis can be 3D printed for difficult anatomic cases.

The impact of the prosthesis can be minimized on supportive ligaments, e.g., the alar, transverse, apical, anterior longitudinal, and capsular ligaments.

The spinal nerves (e.g., at C2), spinal canal contents, and vertebral artery can be preserved during placement.

In some embodiments, preoperative imaging, such as a CT angiogram, for example, can be utilized to rule out an anomalous vertebral artery. In 976 C1-2 joints examined, incidence of anomalous vertebral artery was 0.72%. The variability of posterior arch anatomy of C1 may also emerge as a factor in surgical planning in some cases.

Figure 9B:
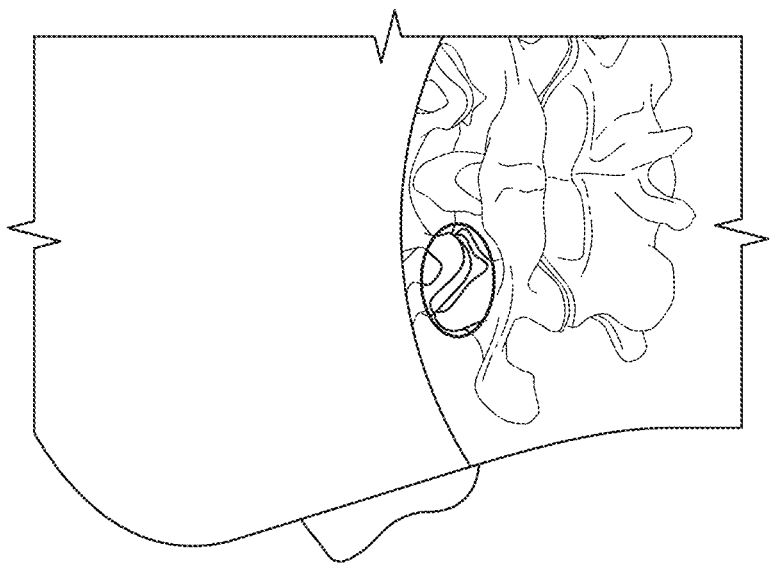
FIGS. 9A-9B illustrate an expandable delivery device to access the mid-point of the atlanto-axial joint.
Figure 9A:
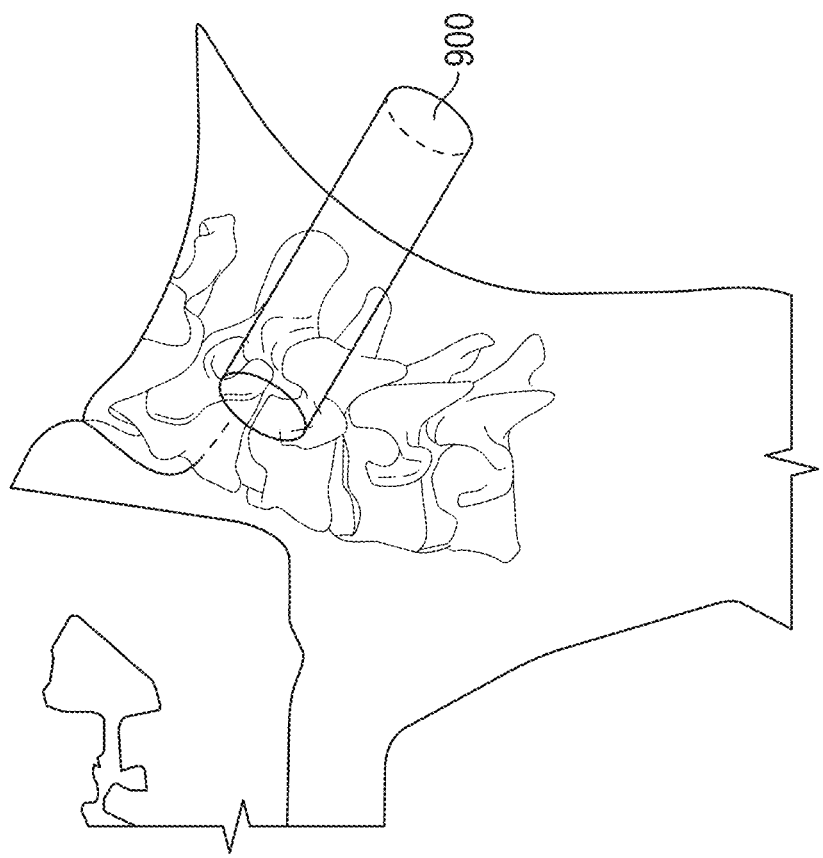

In some embodiments, a vertebral joint replacement prosthesis, such as a cervical joint replacement prosthesis (e.g., at C1-2) can be performed utilizing an anterior, posterior, or lateral approach. Placement of a bifid spinous process over mid-dens shadow on fluoroscopy provides a true AP direction, and allows placement of an expandable delivery device, such as an expandable tube 900 to the mid-point of the vertebral joint, e.g., C1-2 joint, avoiding the vertebral artery and canal, as shown schematically in FIGS. 9A and 9B. Alternatively, a guide wire can be placed fluoroscopically, and serve as initial step in tube placement using a Seldinger technique.

Use of an O-arm for intra-operative navigation can confirm accuracy of placement of the device win patients with difficult anatomy.

FIGS. 24A-24E illustrate yet another prosthesis 2400 that can be implanted anywhere from the occipito-atlantal to the sacroiliac joint. The prosthesis can include a first or ball element 2402 for placement in a first vertebrae (such as the C1 vertebrae for example), and a second or trough element 2404 for placement in a second vertebrae directly adjacent to the first vertebrae (such as the C2 vertebrae for example). Although the prosthesis is described with respect to features shown in FIGS. 24A-24E, the prosthesis can be combined with features of any of the other prostheses described herein.

Figure 24A:
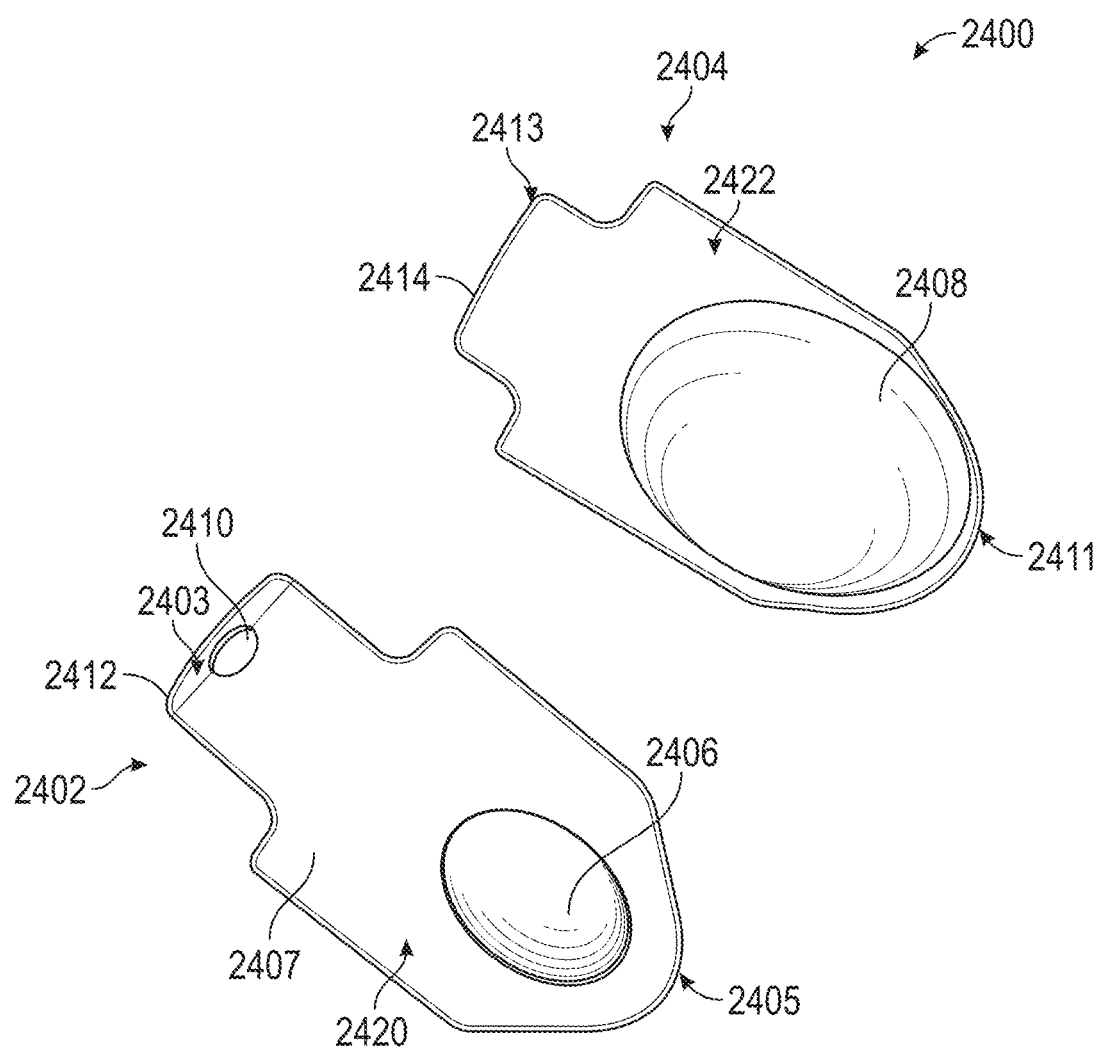

The ball element 2402 can include a body portion 2420 with an articulating surface and a bone facing surface. The ball element 2402 can include a convex surface 2406 on a first or superior side of the body portion 2420 and/or a generally flat surface 2401 on a second or inferior side of the body portion 2420. As shown in FIG. 24A, the convex surface 2406 is non-spherical. The convex surface 2406 can be substantially spherical, oval, oblong, or another shape in some cases. The convex surface 2406 can extend from or be surrounded by an otherwise generally flat surface 2407.

A posterior side 2403 of the body portion 2420 can include one or more flanges 2412 to secure the ball element 2402 to a posterior side of the vertebrae. The flange 2412 may be shaped to the profile of the C2 facet so that the ball element 2402 can be secured to a posterior facing side of the facet joint. The free end 2412a of the flanges 2412 can extend generally away or in an opposite direction from the convex surface 2406 (see FIG. 24C), for example an inferior direction. The free end portion 2412a of the flange 2412 can be positioned at a non-zero angle relative to the generally flat surface 2401, for example between about 90 degrees and 135 degrees, or between about 110 degrees and 130 degrees. A transition portion 2412b between the generally flat surface 2401 and the free end portion 2412a can be at a greater angle relative to the generally flat surface 2401 compared to the free end portion 2412a, for example between about 135 degrees and about 180 degrees, or between about 150 degrees and 170 degrees. Each of the one or more flanges 2412 can include at least one aperture 2410 configured to house bone screws therethrough to attach the ball element 2402 to a vertebrae, such as the C1 vertebrae on the posterior side of the facet joint. For example, as illustrated, the ball element 2402 can include a single flange 2412 with a single aperture 2410. Each aperture 2410 can have a diameter at least about 1.0 mm and/or less than or equal to about 3.0 mm, for example between about 1.5 mm and 2.5 mm, or about, at least about, or no more than about 1.0, 1.5, 2.0, 2.5, or 3.0 mm or more or less, including ranges encompassing any two of the foregoing values.

The trough element 2404 can include a body portion 2422 with an articulating surface and a bond facing surface. The trough element 2404 can include a concave surface 2408 on a first or inferior side of the body portion 2422. The concave surface 2408 is configured to articulate with the convex surface 2406 of the ball element 2402. The trough element 2404 can include a generally convex surface 2409 opposite the concave surface 2408 on a second or superior side of the body portion 2422 (see FIG. 24C), although in other embodiments, the generally convex surface 2409 can be a generally flat surface. In this configuration, the concave surface 2408 may have a greater depth than the remainder of the body portion 2422. A posterior side 2413 of the body portion 2422 can include one or more flanges 2414 to secure the trough element 2404 to a posterior side of the vertebrae. The flange 2412 may be shaped differently from the flange 2412 of the ball element 2402. For example, the flange 2412 may be shaped to match the profile of the C1 facet so that the trough element 2404 can be secured to a posterior facing side of the facet joint. The flange 2412 can generally extend in the same direction as the convex surface 2409 or in the inferior direction. The flange 2414 can be positioned at a non-zero angle relative to a longitudinal axis extending the superior-inferior direction, for example less than or equal to about 45 degrees, less than or equal to about 30 degrees, or less than or equal to about 15 degrees. Each flange 2414 can include at least one aperture 2416 configured to house bone screws therethrough to attach the trough element 2404 to a vertebrae, such as the C2 vertebrae. For example, as illustrated, the trough element 2404 can include a single flange 2414 with a single aperture 2416. Each aperture 2416 can have a diameter at least about 1.0 mm and/or less than or equal to about 3.0 mm, for example between about 1.5 mm and 2.5 mm, or about, at least about, or no more than about 1.0, 1.5, 2.0, 2.5, or 3.0 mm or more or less, including ranges encompassing any two of the foregoing values. The flange 2414 may extend beyond the generally convex surface 2409 in the superior direction.

The convex surface 2406 and the concave surface 2408, also referred to herein as bearing surfaces, can be displaced from the flanges 2412, 2414 and positioned closer to the opposite end of each respective component 2402, 2404. For example, the bearing surfaces 2406, 2408 can be positioned closer to the anterior sides 2405, 2411 than the posterior sides 2403, 2413 of each respective component 2402, 2404.

The joint prosthesis 2400 may exhibit multiple degrees of freedom of movement, including axial rotation, lateral translation, anteroposterior translation, flexion-extension, and/or vertical movement. The bearing surfaces 2406, 2408 permit the ball and trough elements 2402, 2404 to move relative to each other in one or more directions, for example, the bearing surfaces 2406, 2408 may allow the ball and trough elements 2402, 2404 to bend or tilt relative to each in the anterior-posterior direction such that anterior or posterior ends of the ball and trough elements 2402, 2404 move closer together or further apart in the longitudinal direction when implanted. The bearing surfaces 2406, 2408 may allow the ball and trough elements 2402, 2404 to bend or tilt relative to each in the medial-lateral direction such that the lateral sides of the ball and trough elements 2402, 2404 move closer together or further apart in the longitudinal direction when implanted. The bearing surfaces 2406, 2408 may allow the ball and trough elements 2402, 2404 to rotate relative to each other about a longitudinal axis of the bearing surfaces 2406, 2408, for example within a single horizontal plane when implanted.

The bearing surfaces 2406, 2408 may not exactly match. For example, the length 24FX and/or the width 24EX of the concave surface 2408 can be greater than, equal to, or less than the respective dimensions of the convex surface 2406, depending on the desired range of motion, for example at least 1.25× greater, at least 1.5× greater, at least 2× greater, or at least 3× greater. This allows the ball element 2402 and the trough element 2404 to translate relative to each other in the anterior-posterior direction and/or the medial-lateral direction when implanted. In some configurations, the ball element 2402 may translate relative to the trough element 2404 in any direction when implanted. As illustrated, each bearing surface 2406, 2408 may have a length in the anterior-posterior direction that is greater than a width in the medial-lateral direction to permit a greater range of translation in the anterior-posterior direction compared to the medial-lateral direction, for example at least 1.5× greater or at least 2× greater.

Figure 24B:
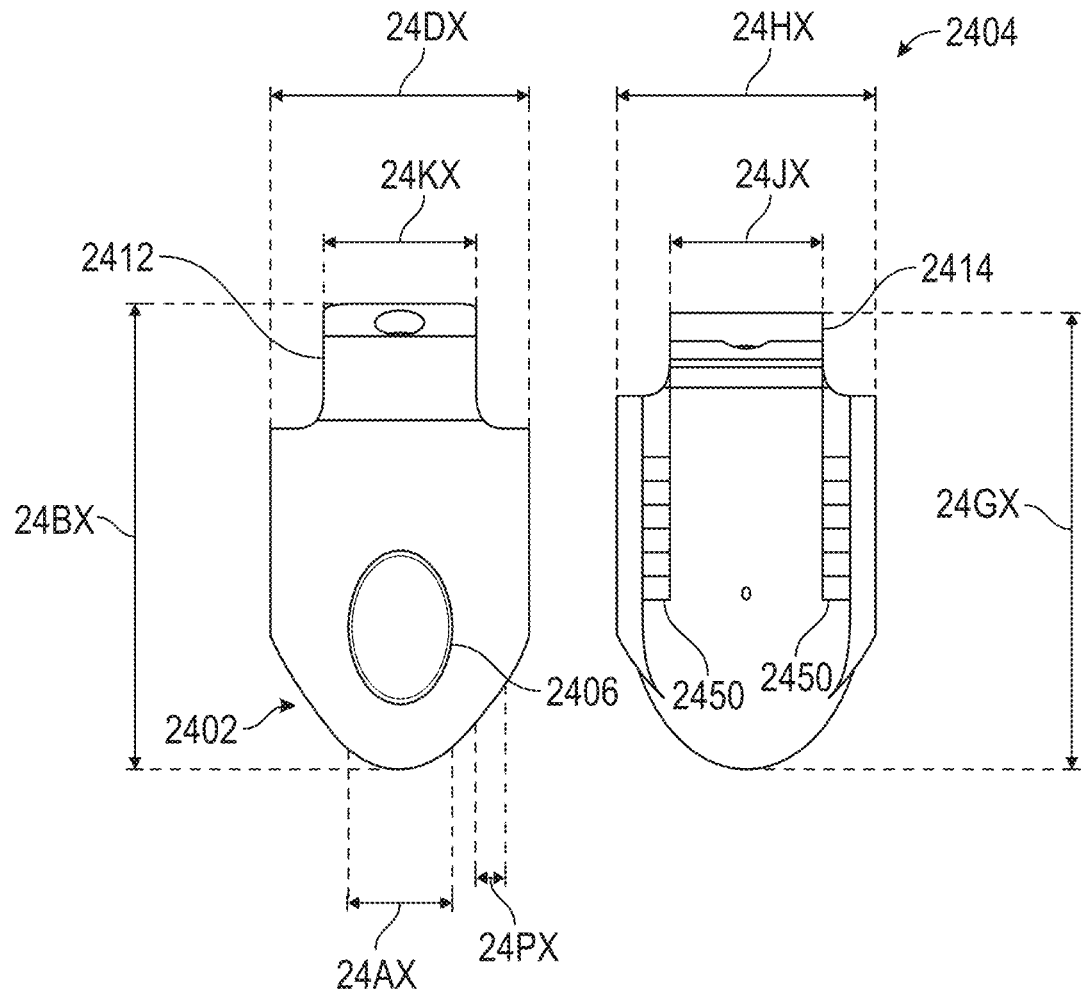

FIG. 24B illustrates a plan view of components shown in FIG. 24A. The prosthesis 2400 can be sized to fit within a C1-C2 facet joint. The ball element 2402 can have a length dimension 24BX in an anterior-posterior direction and a width dimension 24DX in the medial-lateral direction. The length dimension 24BX can be greater than the width dimension 24DX, for example at least 1.25×, at least 1.5× or at least 2.0×. In some embodiments, the length dimension 24BX can be, for example, between at least about 10 mm and/or less than or equal to about 25 mm, for example between about 20 mm and about 25 mm, or about, at least about, or no more than about 15, 16, 17, 18, 19, 20, 21, 22, 23, 24, 25 mm or more or less, including ranges encompassing any two of the foregoing values. In some embodiments, the maximum width dimension 24DX can be, for example, at least about 10 mm and/or less than or equal about 20 mm, for example between about 10 mm and about 15 mm, or about, at least about, or no more than about 10, 11, 12, 13, 14, 15, 16, 17, 18, 19, 20 mm or more or less, including ranges encompassing any two of the foregoing values.

The trough element 2404 can include a length dimension 24GX in the anterior-posterior direction and a width dimension 24HX in the medial lateral direction. The length dimension 24GX of the trough element 2404 can be less than or equal to the length dimension 24BX of the ball element 2402. In some embodiments, the length dimension 24GX can be, for example, at least about 10 mm and/or less than or equal to about 25 mm, for example between about 15 mm and about 20 mm, or about, at least about, or no more than about 10, 11, 12, 13, 14, 15, 16, 17, 18, 19, 20, 21, 22, 23, 24, 25 mm or more or less, including ranges encompassing any two of the foregoing values. The maximum width dimension 24HX of the trough element 2404 can be about the same as maximum width dimension 24DX of the ball element 2402. In some embodiments, the width dimension 24HX can be, for example, at least about 10 mm and/or less than or equal about 20 mm, for example between about 10 mm and about 15 mm, or about, at least about, or no more than about 10, 11, 12, 13, 14, 15, 16, 17, 18, 19, 20 mm or more or less, including ranges encompassing any two of the foregoing values.

The flange 2412 of the ball element 2402 can have a width dimension 24KX that is less than or equal to the maximum width dimension 24DX of the ball element 2402. The flange 2414 of the trough element 2404 can have a width dimension 24JX that is less than or equal to the maximum width dimension 24HX of the trough element 2404. In some embodiments, the width dimensions 24KX, 24JX can be, for example, at least about 5 mm and/or less than or equal about 15 mm, for example between about 5 mm and about 10 mm, or about, at least about, or no more than about 5, 6, 7, 8, 9, 10, 11, 12, 13, 14, 15 mm or more or less, including ranges encompassing any two of the foregoing values. As annotated in FIG. 24D, the flange 2412 can have a depth dimension 24LX from the flat surface 2407 to the tip of the flange 2412. In some embodiments, the depth dimension 24LX can be, for example, at least about 2 mm and/or less than or equal to about 6 mm, or about, at least about, or no more than about 2, 2.5, 3, 3.1, 3.2, 3.3, 3.4, 3.5, 3.6, 3.7, 3.8, 3.9, 4, 4.5, 5, 6 mm or more or less, including ranges encompassing any two of the foregoing values. A depth dimension of the flange 2414 can be less than or equal to the depth dimension 24LX of the flange 2412.

Figure 24C:
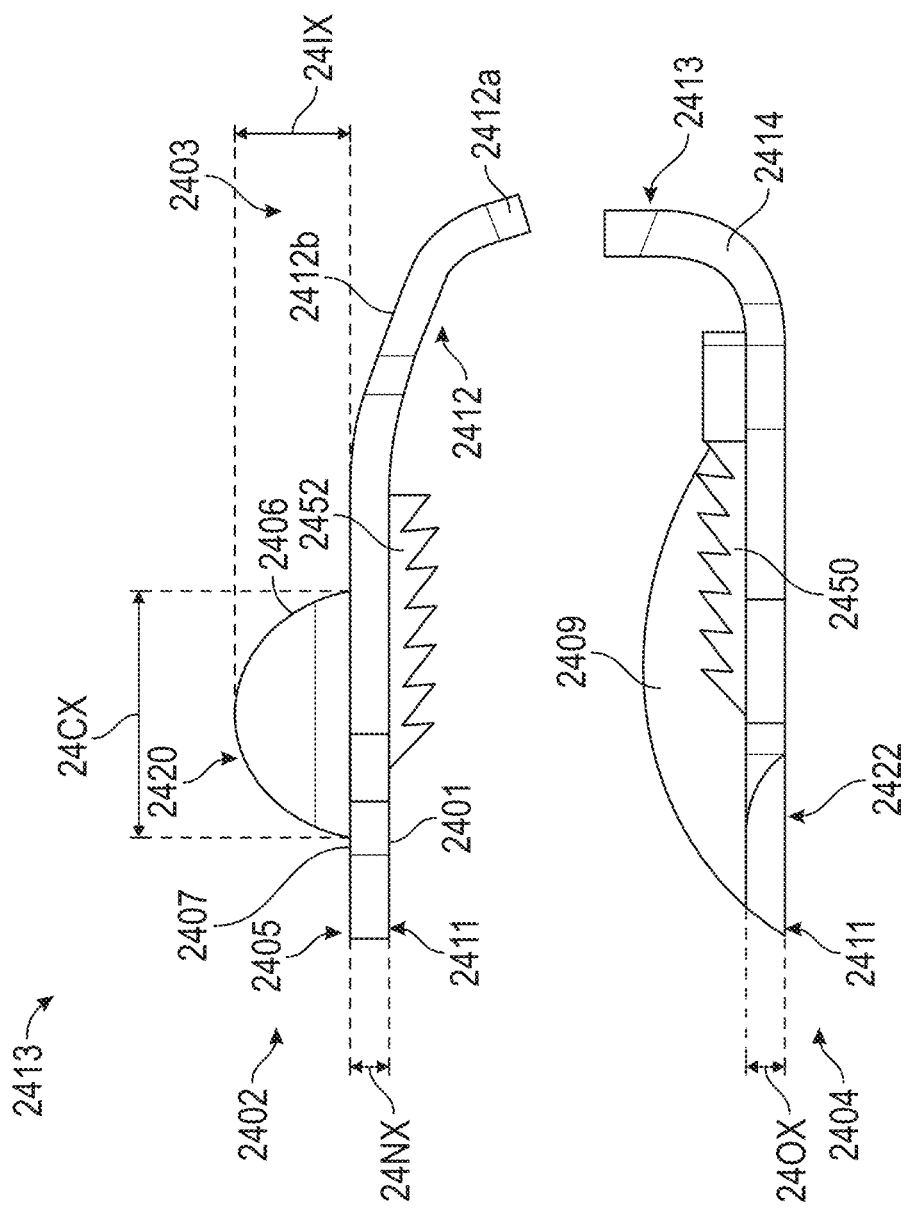

FIG. 24C illustrates side views of the ball element 2402 and trough element 2404 of FIG. 24A. One or both of the ball element 2402 and trough element 2404 can have one or more anchoring elements 2452, 2450 on the respective body portions 2420, 2422 to anchor the components 2402, 2404 to inferior or superior surfaces of the vertebrae. The anchoring elements 2452, 2450 may extend along less than an entire length of the respective ball and trough elements 2402, 2404. In some embodiments, the prosthesis or any element thereof can comprise a biocompatible material, such as a metal such as titanium, for example. Each of the ball element 2402 and the trough element 2404 can be a monolithic element. Although, in some embodiments, the anchoring elements 2452, 2450 may be separately attached to the respective body portions 2420, 2422.

The ball element 2402 can have one or more anchor elements 2452 opposite the convex surface 2406, for example on the second or inferior side of the ball element 2402. The anchoring elements 2452 can include surface features to promote or inhibit bony ingrowth. Each anchoring element 2452 can be a keel with one or more saw teeth, for example a linear array of saw teeth. The linear array of saw teeth may extend in any direction, for example the anterior-posterior direction, the medial-lateral direction, parallel to the major axis of the convex surface 2406, or parallel to the minor axis of the convex surface 2406. As illustrated, the ball element 2402 can include two anchoring elements 2452 spaced apart from each other. The anchoring elements 2452 can extend in the anterior-posterior direction along lateral sides of the ball element 2402. Each anchoring element 2452 can be positioned laterally outward from the convex surface 2406. The anchoring elements 2452 can be spaced apart from the convex surface 2406 in the lateral direction. Each anchoring element can have a width dimension 24PX (annotated on FIG. 24B) in the medial-lateral direction of less than or equal to about 3 mm, less than or equal to about 2 mm, or less than or equal to about 1 mm. In other configurations, the anchoring elements 2452 may be oriented in a different direction with respect to the body portion 2420 or relative to each other.

The trough element 2404 can have one or more anchor elements 2450 opposite the concave surface 2408, for example on the second or superior side of the trough element 2404. The anchoring elements 2450 can include surface features to promote or inhibit bony ingrowth. Each anchoring element 2450 can be a keel with one or more saw teeth, for example a linear array of saw teeth. The linear array of saw teeth may extend in any direction, for example the anterior-posterior direction, the medial-lateral direction, parallel to the major axis of the concave surface 2408, or parallel to the minor axis of the concave surface 2408. As illustrated, the trough element 2404 can include two anchoring elements 2450 spaced apart from each other. The anchoring elements 2450 may extend along a periphery of the generally convex surface 2409. The generally convex surface 2409 may extend beyond the anchoring elements 2450 in the inferior direction. The anchoring elements 2450 can extend in the anterior-posterior direction along lateral sides of the trough element 2404. Each anchoring element 2450 can be positioned laterally outward from the concave surface 2408. Each anchoring element can have a width dimension in the medial-lateral direction of less than or equal to about 3 mm, less than or equal to about 2 mm, or less than or equal to about 1 mm. In other configurations, the anchoring elements 2452 may be oriented in a different direction with respect to the body portion 2420 or relative to each other.

Additionally or alternatively, the ball element 2402 and the trough element 2404 may be secured by an expandable anchor having any of the features of the anchoring elements 2750, 2852, 2850 described below. For example, expandable anchors may be advanced through the apertures in the flanges 2412, 2414.

The body portion 2420 of the ball element 2402 can have a thickness dimension 24NX between the generally flat surface 2407 on the first side and the generally flat surface 2401 on the second side. In some embodiments, the thickness dimension 24NX can be, for example, at least about 0.5 mm and/or less than or equal to about 2 mm, or about, at least about, or no more than about 0.5, 0.6, 0.7, 0.8, 0.9, 1.0, 1.1, 1.2, 1.3, 1.4, 1.5, 1.6, 1.7, 1.8, 1.9, 2.0 mm or more or less, including ranges encompassing any two of the foregoing values. The body portion 2420 can have the same thickness from the anterior side 2405 to the posterior side 2403.

The body portion 2422 of the trough element 2404 can have a thickness dimension 240X between flat surfaces on opposite sides of the trough element 2404 and surrounding the concave surface 2408. The thickness dimension 240X can be generally the same as the thickness dimension 24NX. The body portion 2422 have the same thickness from the anterior side 2411 to the posterior side 2413.

Figure 24D:
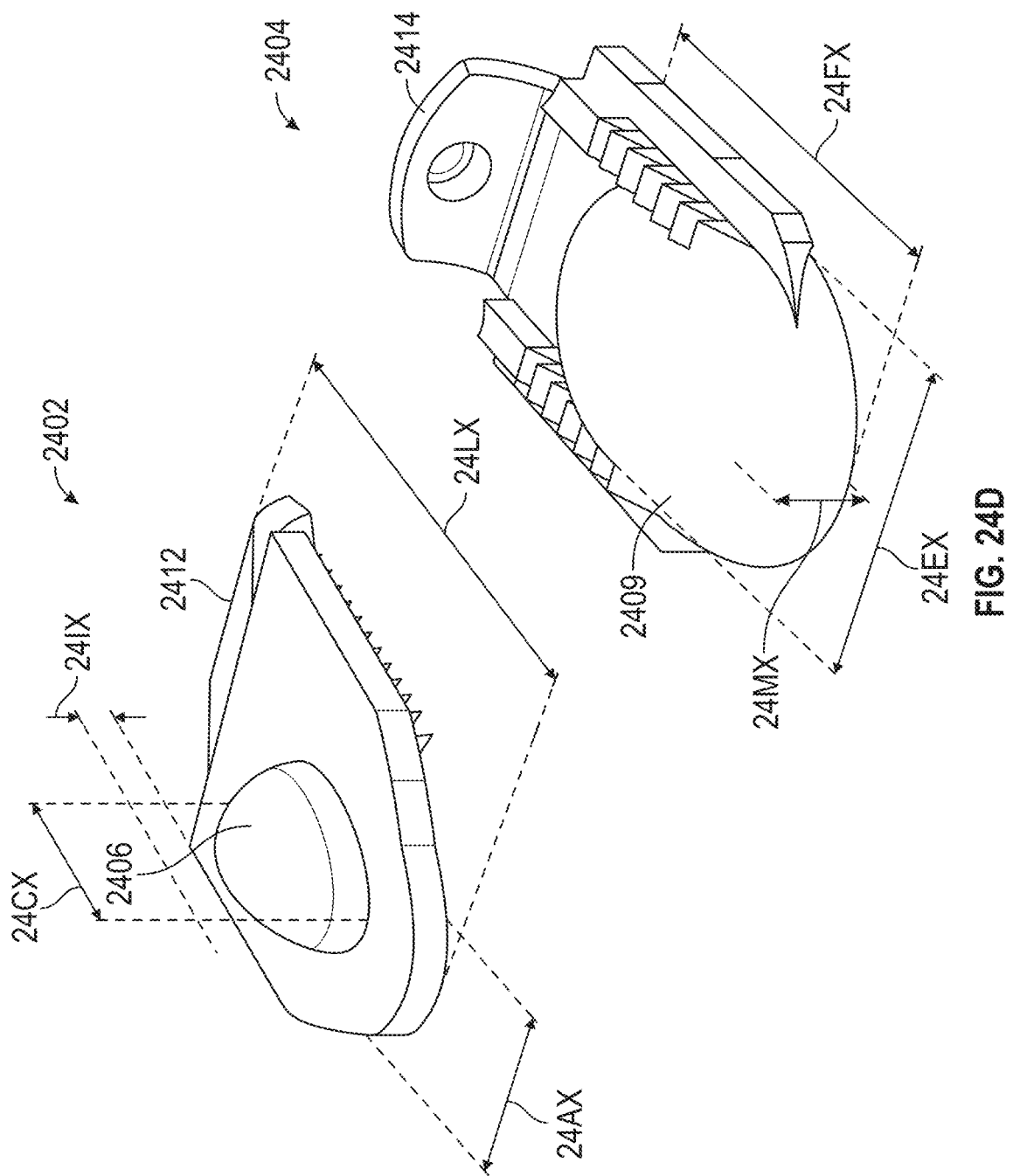

Now referring to FIG. 24D, which shows perspective views of the ball element 2402 and trough element 2404, the convex surface 2406 can have a length dimension 24CX in the anterior-posterior direction, a width dimension 24AX in the medial-lateral direction, and a thickness dimension 241X in the superior-inferior direction. The length dimension 24CX can be greater than or equal to the width dimension 24AX and the thickness dimension 241X. The width dimension 24AX can be greater than or equal to the thickness dimension 241X. The length dimension 24CX can be at least about 10%, at least about 20%, at least about 30%, at least about 40%, or at least about 50% longer than the width dimension 24AX or the thickness dimension 241X. In some embodiments, the width dimension 24AX can be, for example, at least about 2 mm and/or less than or equal to about 12 mm, for example between about 3 mm and about 6 mm, or about, at least about, or no more than about 2, 3, 4, 5, 6, 7, 8, 9, 10, 11, or 12 mm or more or less, including ranges encompassing any two of the foregoing values. In some embodiments, the length dimension 24CX can be between about 2 mm and about 12 mm, for example between about 4 mm and about 8 mm, or about, at least about, or no more than about 2, 3, 4, 5, 6, 7, 8, 9, 10, 11, or 12 mm or more or less, including ranges encompassing any two of the foregoing values. In some embodiments, the thickness dimension 241X is dependent on the desired amount of movement, for example a smaller thickness will increase range of motion. The thickness dimension 241X can be between about 1 mm and about 5 mm, or about, at least about, or no more than about 1, 1.5, 2, 2.1, 2.2, 2.3, 2.4, 2.5, 2.6, 2.7, 2.8, 2.9, 3, 3.5, 4 mm or more or less, including ranges encompassing any two of the foregoing values. The thickness dimension 241X can be less than the thickness dimension 24LX of the flange 2412 such that the flange 2412 extends further in one direction than the convex surface 2406 extends in the opposite direction.

The concave surface 2408 of the trough element 2404 can have a length dimension 24FX in the anterior-posterior direction, a width dimension 24EX in the medial-lateral direction, and a thickness dimension 24MX in the superior-inferior direction. The length dimension 24FX can be greater than or equal to the width dimension 24EX and/or the thickness dimension 24MX. The width dimension 24EX can be greater than or equal to the thickness dimension 241X. The length dimension 24FX can be at least about 10%, at least about 20%, at least about 30%, at least about 40%, or at least about 50% longer than the width dimension 24EX or the thickness dimension 24MX. In some embodiments, the width dimension 24EX can be, for example, at least about 2 mm and/or less than or equal to about 12 mm, for example between about 8 mm and about 12 mm, or about, at least about, or no more than about 2, 3, 4, 5, 6, 7, 8, 9, 10, 11, or 12 mm or more or less, including ranges encompassing any two of the foregoing values. In some embodiments, the length dimension 24FX can be between about 2 mm and about 12 mm, for example between about 8 mm and about 12 mm, or about, at least about, or no more than about 2, 3, 4, 5, 6, 7, 8, 9, 10, 11, or 12 mm or more or less, including ranges encompassing any two of the foregoing values. In some embodiments, the thickness dimension 24MX can be, for example, between about 1 mm and about 5 mm, or about, at least about, or no more than about 1, 1.5, 2, 2.1, 2.2, 2.3, 2.4, 2.5, 2.6, 2.7, 2.8, 2.9, 3, 3.5, 4 mm or more or less, including ranges encompassing any two of the foregoing values. The thickness dimension 24MX can be less than the thickness dimension 241X of the convex surface 2406 and/or greater than the thickness dimension 240X of the body portion 2422.

FIG. 24E illustrates a posterior side of the ball element 2402 and an anterior side of the trough element 2404.

With reference to FIGS. 26A-26D, another illustrative embodiment of a joint prosthesis for the C1-C2 joint is shown. The prosthesis 2600 resembles the prosthesis 2400 discussed above in many respects. Accordingly, numerals used to identify features of the prostheses 2400 are incremented by a factor of two hundred (200) to identify like features of the prosthesis 2600. This numbering convention generally applies to the remainder of the figures. Any component or step disclosed in any embodiment in this specification can be used in other embodiments.

The ball element 2602 can include a body portion 2620 having paddles 2621a, 2621b to increase stability and diminish subsidence. The paddles 2621a, 2621b may extend laterally outward from the anchor elements 2652 and/or the flange 2612. The region of the ball element 2602 having the lateral paddles 2621a, 2621b can form the widest region of the ball element 2602. The region having the lateral paddles 2621a, 2621b can be wider than the anterior end 2605 or the posterior end 2603 of the ball element 2602. A width of the region of the ball element 2602 having the lateral paddles 2621a, 2621b can be at least 1.5× greater, at least 2× greater, at least 2.5× greater, or at least 3× greater than the width of the flange 2612. As illustrated the lateral paddles 2621a, 2621b may be different in size and/or shape such that the ball element 2602 is asymmetric about the anterior-posterior axis of the ball element 2602. For example, a first lateral paddle 2621a can extend laterally outward from the flange 2612 a greater distance than the than a second lateral paddle 2621b. An outer periphery of the first paddle 2621a may be shaped differently than the outer periphery of the second paddle 2621b. In other configurations, the paddles 2621a, 2621b may be similarly shaped and sized such that the ball element 2602 is symmetrical about the anterior-posterior axis.

The trough element 2604 can include paddles 2623a, 2623b to increase stability and diminish subsidence. The paddles 2623a, 2623b may extend laterally outward from the generally convex surface 2609 or the flange 2614. The region of the trough element 2604 having the lateral paddles 2623a, 2623b can form the widest region of the trough element 2604. The region having the lateral paddles 2623a, 2623b can be wider than the anterior end 2611 or the posterior end 2613 of the trough element 2604. A width of the region of the trough element 2604 having the lateral paddles 2623a, 2623b can be at least 1.5× greater, at least 2× greater, at least 2.5× greater, or at least 3× greater than the width of the flange 2614. As illustrated the lateral paddles 2623a, 2623b may be different in size and/or shape such that the trough element 2604 is asymmetric about the anterior-posterior axis of the trough element 2604. For example, a first lateral paddle 2621a can extend laterally outward from the flange 2614 a greater distance than the than a second lateral paddle 2623b. An outer periphery of the first paddle 2623a may be shaped differently than the outer periphery of the second paddle 2623b. The paddles 2623a, 2623b may be shaped differently than the paddles 2621a, 2621b of the ball element 2602. A maximum width of the trough element 2604 in the region of the paddles 2623a, 2623b may be greater than a maximum width of the ball element 2602 in the region of the paddles 2621a, 2621b. In other configurations, the paddles 2623a, 2623b may be similarly shaped and sized such that the trough element 2604 is symmetrical about the anterior-posterior axis.

Figure 26A:
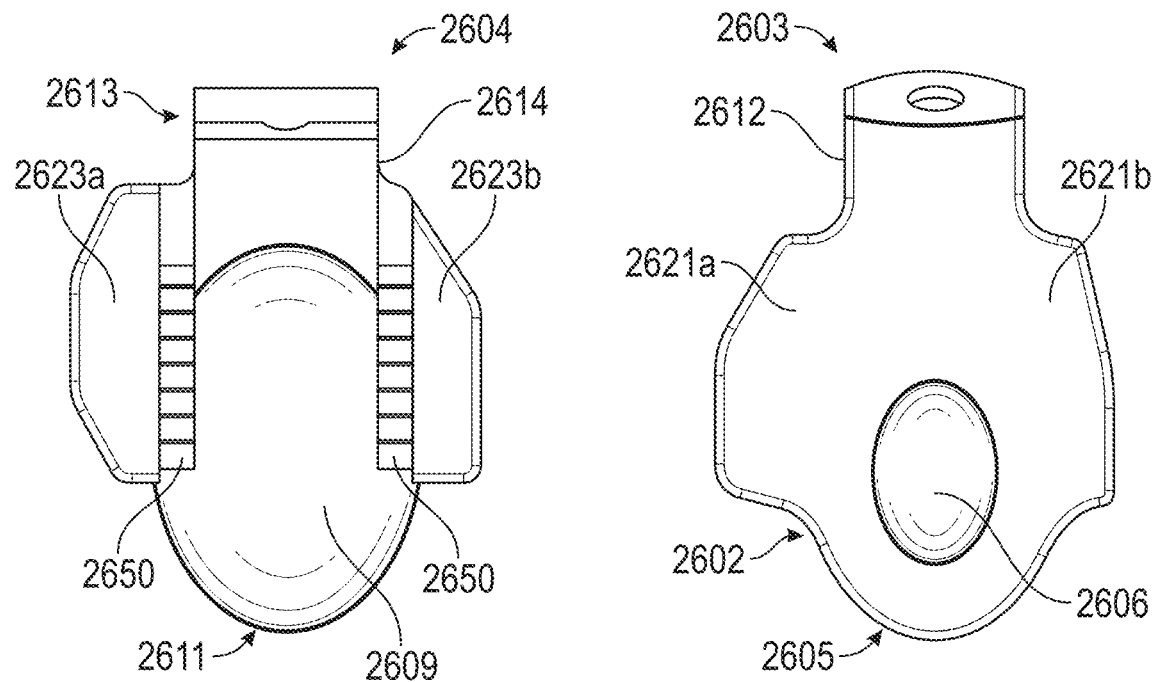
Figure 26B:
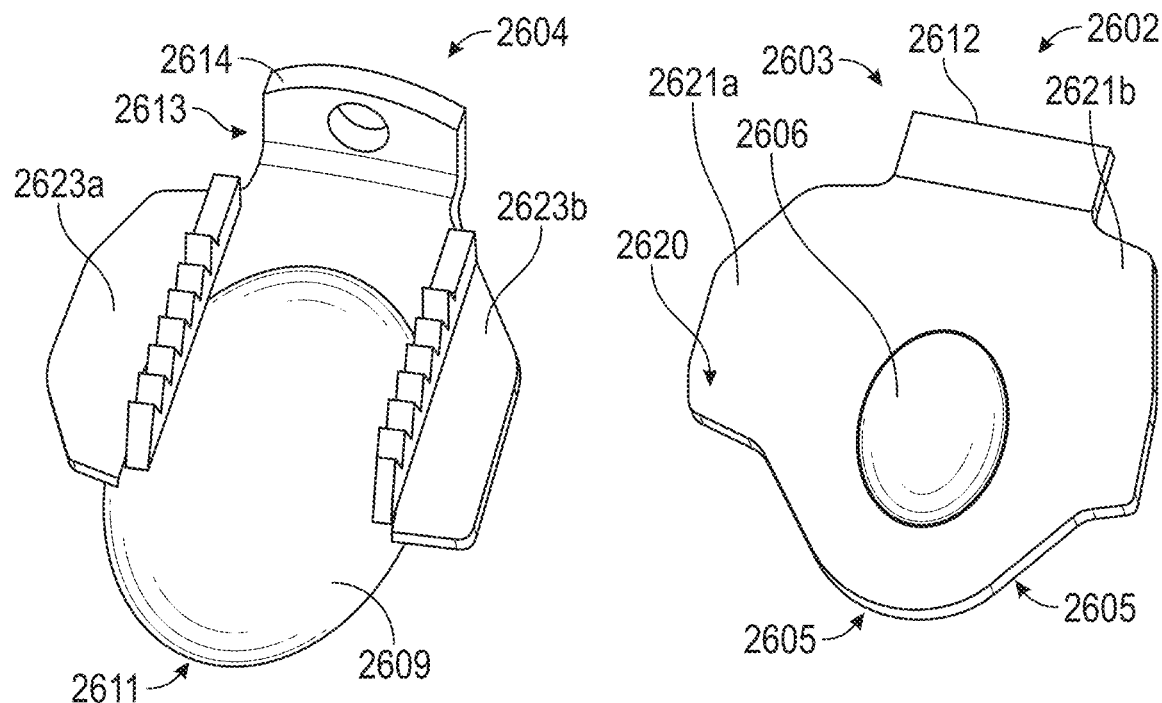
Figure 26D:
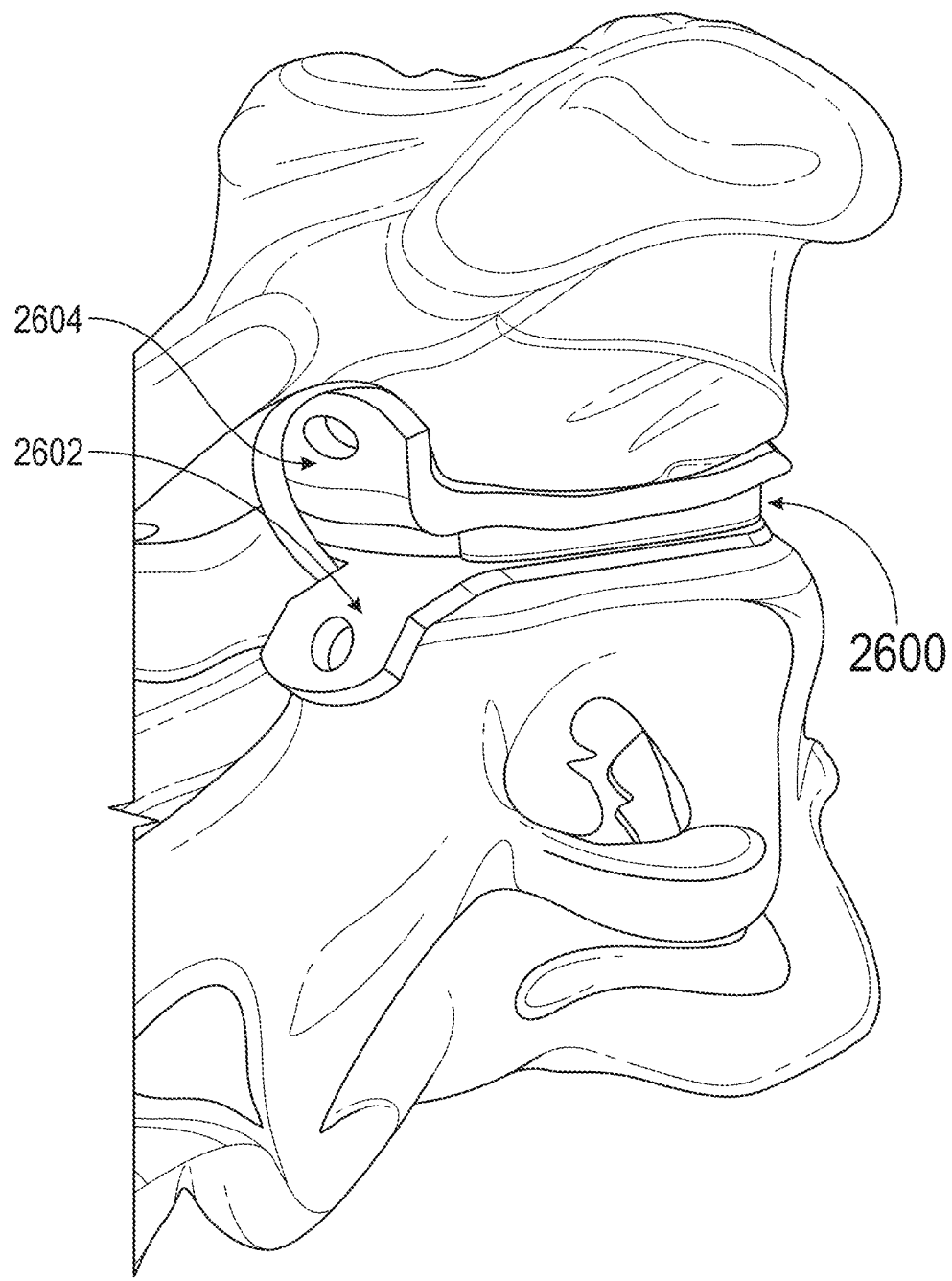

As shown in FIG. 26D, the prostheses 2600 can be implanted between C1 and C2 in the facet joint region and attach to a posterior facing side of the facet joint.

Although certain features of the cervical joint prostheses are described with respect to a ball element or trough element, any of the features described herein are interchangeable between the two elements. For example, the ball feature could be on the inferior side of a first element and the trough could be on the superior side of a second element.

Certain prostheses are described with respect to the C1-C2 joint, but could be placed between any of the other cervical or thoracic facet joints by modifying the relative dimensions to accommodate the anatomy of the other joints, for example increasing a thickness of the convex surface of the ball element or decreasing a width of the prostheses.

Sub-Axial Cervical Facet Joint Prostheses

Also described herein are sub-axial cervical facet joint prostheses. Chronic neck pain is a common musculoskeletal complaint in the US and can affect 66% of the population during their lifetime.

Figure 11:
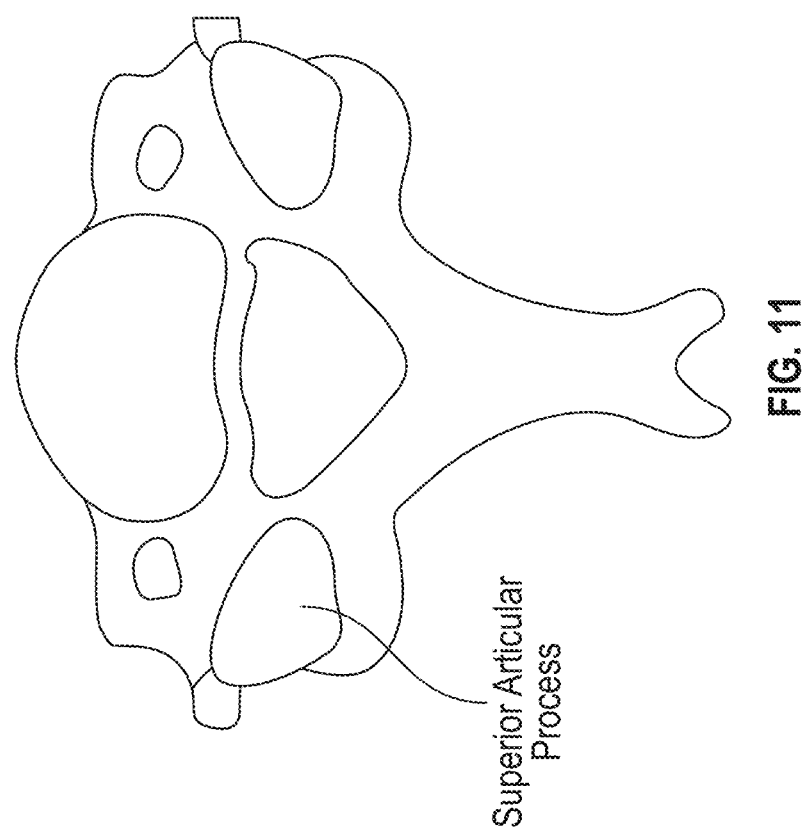
FIGS. 10-11 illustrate a sub-axial cervical facet joint.
Figure 10:
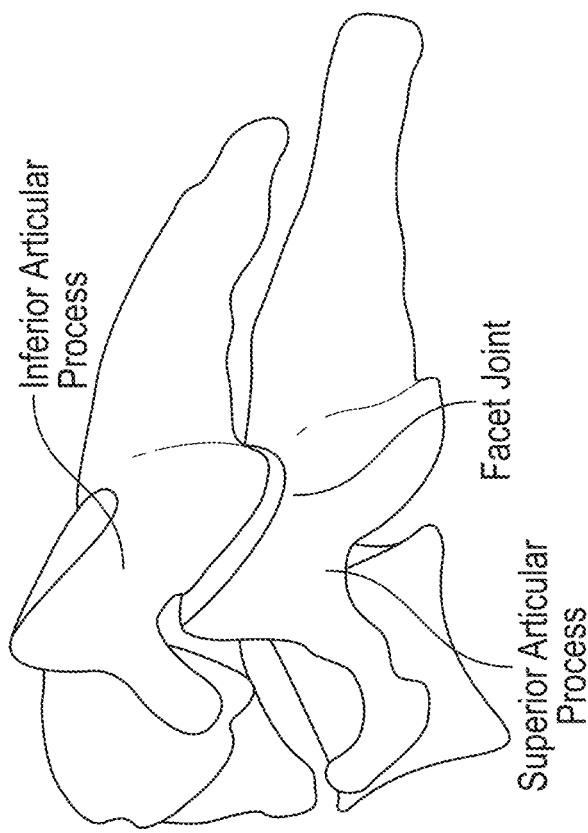

The cervical motion segment is formed by the three articulations between adjacent vertebrae: one relatively anterior disc and two relatively posterior facet joints, as shown schematically in FIGS. 10 and 11. The adoption of motion-preserving total disc replacement has focused attention on facet joint arthritis. Total disc replacements are intended to alleviate intervertebral disc pathologies that are often accompanied by facet joint arthritis, generally a contraindication for implantation. A mobile facet joint prosthesis could advantageously foster comprehensive treatment of the motion segment, without requiring a total disc replacement in some cases.

The cervical facet joints are paired diarthrodial, synovial joints located between the superior and inferior articular pillars in the posterior cervical column, and have an oval appearance.

Each facet joint is lined with hyaline cartilage and contains a meniscus. A fibrous joint capsule exists that is richly innervated with both mechanoreceptors and nociceptors. The joint volume is typically less than about 1 mL. The facet joints are roughly planar, but not truly flat, being reciprocally convex and concave. FIGS. 4A-4D illustrate schematically a comparison of sub-axial facet joint morphology with other cervical joints.

Articular cartilage covers the opposed surfaces of each of the facets, resting on a thickened layer of subchondral bone, and synovial membrane bridges the margins of the cartilaginous portions of the joint, in a low-friction environment. A baggy fibrous joint capsule covers the joint like a hood. Capsular ligaments hold adjacent vertebrae to one another and stabilize the joint.

Figure 12:
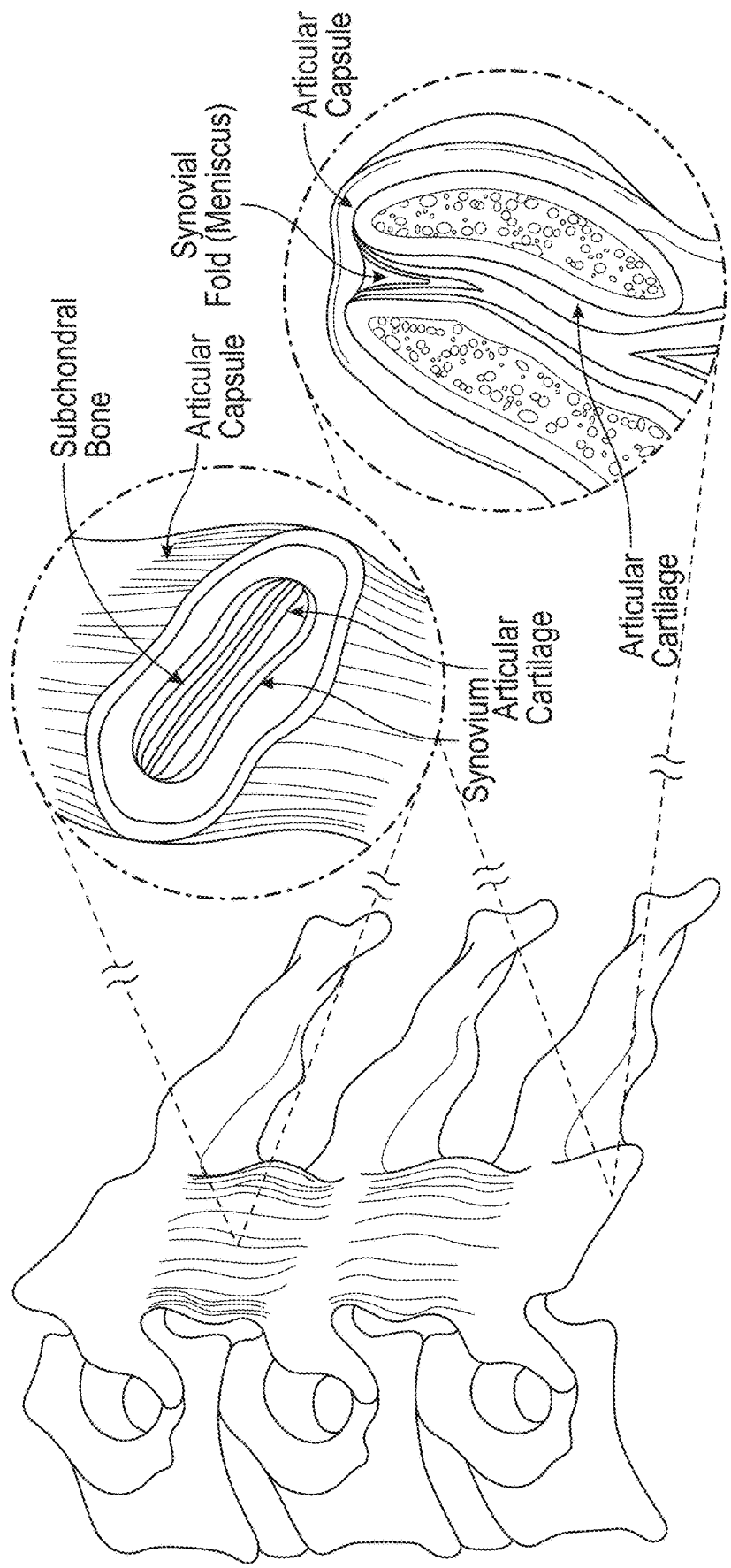
FIG. 12 illustrates facet joints of the lower cervical spine.

A fibroadipose meniscoid projects into the superior and inferior aspects of the joint and includes a fold of synovium that encloses fat, collagen and blood vessels. The meniscoid increases the contact surface area during motion and slides during flexion of the joint to cover articular surfaces exposed by this movement. The facet joints of the lower cervical spine have progressively less rotation than the upper cervical spine. FIG. 12 illustrates additional features of facet joint anatomy.

Thinning of the cartilage, formation of synovial cysts, fibrocartilage proliferation of the capsules, and osteophyte formation can be seen in facet arthritis. The joint capsule starts to have fibrosis, neovascularization, and inflammation in early stages. Later, fibrocartilage proliferation contributes to the hypertrophied capsule. Osteophytes form at the later stage, usually at the border of the capsular insertion.

Facet joint osteoarthritis represents the functional failure of the synovial facet joints. Although often viewed as a disease of articular cartilage loss, the process of failure actually involves the whole joint, including the subchondral bone, cartilage, ligaments, capsule, synovium, and periarticular paraspinal muscles. Joint alignment and load distribution are thought to be major factors in the development and progression of cervical facet joint osteoarthritis. The capsular ligaments are strong and serve as the main stabilizing tissue in the spinal column. The capsular ligaments have a high peak force and elongation potential, meaning they can withstand large forces before rupturing. Capsular injury can lead to capsular ligament laxity and excess motion of the facet joint, which can result in cervical instability. The classic radiographic hallmarks of cervical facet joint osteoarthritis involve both degenerative and proliferative features, including narrowing of the facet joint space, subarticular bone erosions, subchondral cysts, osteophyte formation, and hypertrophy of the articular process. Although CT is generally more accurate than MM for assessing bony pathology, there is good correlation between CT and MRI in disease assessment. SPECT CT and fat-suppressed MM have improved the ability to evaluate changes in the facet joints and surrounding structures. Epidemiological studies evaluating the association between radiographic facet joint osteoarthritis and pain have produced conflicting results, with several studies showing no relationship between the presence or severity of facet joint osteoarthritis on CT/MRI and the presence of neck pain.

Kellgren's grading system of facet joint degenerative changes can be applied to cervical spine using AP, lateral, and oblique radiographs. The grading system can be as follows. Grade 0. Absence of degeneration of facet joints. Grade 1. Doubtful osteophytes on margins of the articular facets. Grade 2. Definite osteophytes and subchondral sclerosis in facet joints. Grade 3. Moderate osteophytes, subchondral sclerosis, and some irregularity of the articular facets. Grade 4. Many large osteophytes, severe sclerosis, and irregularity of the facet joints. No studies of cervical facet joint arthritis prevalence have used advanced imaging. There are several risk factors for cervical facet joint osteoarthritis. Age is strongly associated with prevalence of cervical facet joint osteoarthritis. Higher BMI is associated with greater prevalence of cervical facet joint osteoarthritis in women. Occupational factors such as stair-climbing, standing and jolting activities are not associated with cervical facet joint osteoarthritis. No studies have directly examined the role of heredity in cervical facet joint osteoarthritis.

Pain can arise from nociceptors within and surrounding the joints, including nociceptors in the bone itself. Facet joints and their capsules are well innervated by the medial branches of the dorsal primary rami of the spinal nerves, where both free nerve endings and mechanoreceptors have been identified. Clear pain referral patterns exist. Most symptoms arise from C2-3, C5-6 or C6-7 facet joints. Prolonged peripheral inflammation can lead to central sensitization, neuronal plasticity, and the development of chronic spinal pain. No examination maneuvers are pathognomonic for symptomatic facet joint osteoarthritis, and mechanical tests to stress the facet joints probably load the intervertebral discs as well, decreasing their predictive value. Owing to lack of specificity of facet joint osteoarthritis on imaging, anesthetic block using fluoroscopy has become standard practice for diagnosing whether a particular joint is producing pain. Targets for diagnostic block include the joint itself or the medial branches of the dorsal rami that supply the sensory innervation to the joint.

The cervical facet joints permit a gliding motion between their articular surfaces of 4 to 6 mm with the superior facet gliding forward and up, or backward and down with respect to the lower facet. With rotation or lateral bending, the facet on one side moves forward and up and the contralateral facet moves in the opposite direction, accounting for the "coupling" of rotation. The cervical joint embodiments described herein can reproduce the gliding motion of native facet joints.

A complex relationship exists in load-sharing between the facet joints and the disc, and depends largely on spinal posture. In most cases, the disc is the primary load-bearing structure in each motion segment. Normally, load carried by the facets can be up to 33% of total load borne by that spinal segment. More load is transmitted through the facet joints when the spine is extended and less when it is flexed or in a neutral position. Degenerative disc disease causes a marked increase in transmission of force across the facet joints, as less body weight is supported by the disc when is becomes functionally incompetent. Up to 70% of an axial load can be borne by the facet joints in cases of severe disc space narrowing. The first role of spinal musculature is to control movement of the spine and contribute stabilization. The second role of spinal musculature is to provide proprioceptive feedback. With aging, paraspinal muscle mass decreases, which compromises both of these functions. Adult degenerative scoliosis and degenerative spondylolisthesis are thought to be related to facet joint osteoarthritis and failure of the motion segment.

In some embodiments, disclosed herein is an artificial facet joint replacement prosthesis. In some embodiments, the prosthesis can be sized and configured for implantation within sub-axial joints, including but not limited to C2-3, C3-4, C4-5, C5-6, C6-7, C7-T1, and other thoracic, or lumbar joints. In some embodiments, joints can be sacroiliac joints.

Figure 13:
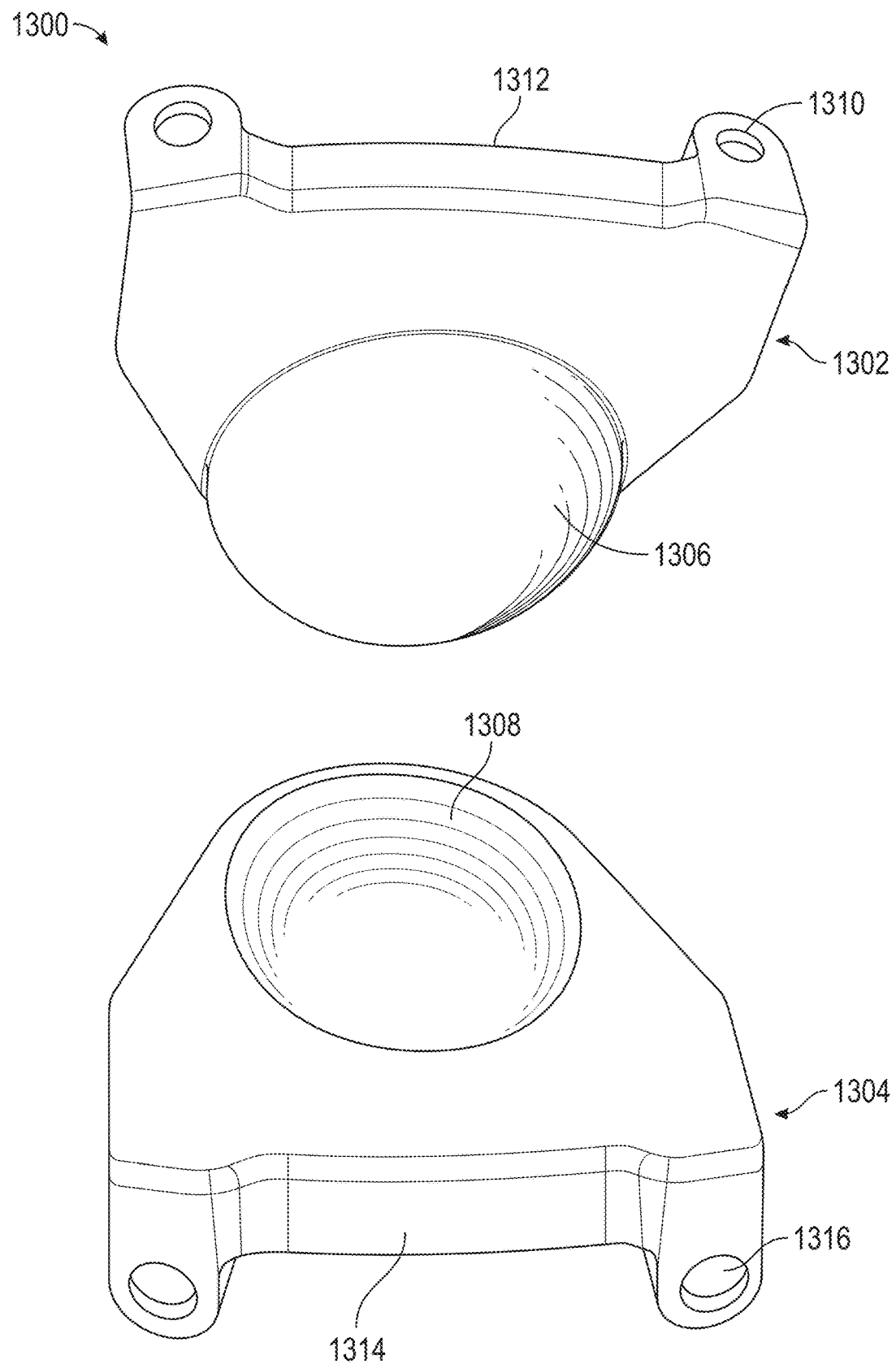
FIG. 13 illustrates a joint prosthesis that can be placed in a sub-axial cervical facet joint.

In some embodiments, the prosthesis can be configured to be placed within an intervertebral joint, including but not limited to a cervical facet joint without extending into the disc space. In some embodiments, as illustrated in FIG. 13, the prosthesis 1300 can include a ball element 1302 for placement in a first vertebrae (such as the C5 vertebrae for example), and a trough element 1304 for placement in a second vertebrae directly adjacent to the first vertebrae (such as the C6 vertebrae for example) The prosthesis 1300 can include any features of the C1-C2 prostheses described above.

The ball element 1302 can include a convex inferior surface 1306 and a generally flat superior surface, as well as a generally superiorly-extending flange 1312 including laterally-spaced apart apertures 1310 configured to house bone screws therethrough to attach the ball element to a vertebrae, such as the C5 vertebrae, for example on the posterior facing side of the facet joint. The convex inferior surface 1306 can be substantially spherical, oblong, or another shape in some cases, but in some embodiments has a maximum diameter that is greater than the depth of the trough such that it is flatter/less deep than a spherical socket geometry. In some embodiments, the maximum diameter can be about, at least about, or no more than about 5%, 10%, 15%, 20%, 25%, 30%, 35%, 40%, 45%, 50%, 60%, 70%, 80%, 90%, 100%, or more or less greater than that of the depth of the trough, including ranges including any two of the foregoing values.

The trough element 1304 can include a concave superior surface 1308 configured to articulate with the convex inferior surface 1306 of the ball element. The trough element 1304 can also include a generally flat inferior surface 1308, as well as a generally inferiorly-extending flange 1314 including laterally-spaced apart apertures 1316 configured to house bone screws therethrough to attach the trough element 1304 to a vertebrae, such as the C6 vertebrae, for example on the posterior side. In some embodiments, the ball element 1302 and the trough element 1304 can have substantially the same diameter or radius. In some embodiments, the prosthesis or any element thereof can comprise a biocompatible material, such as a metal such as titanium, for example.

Figure 14B:
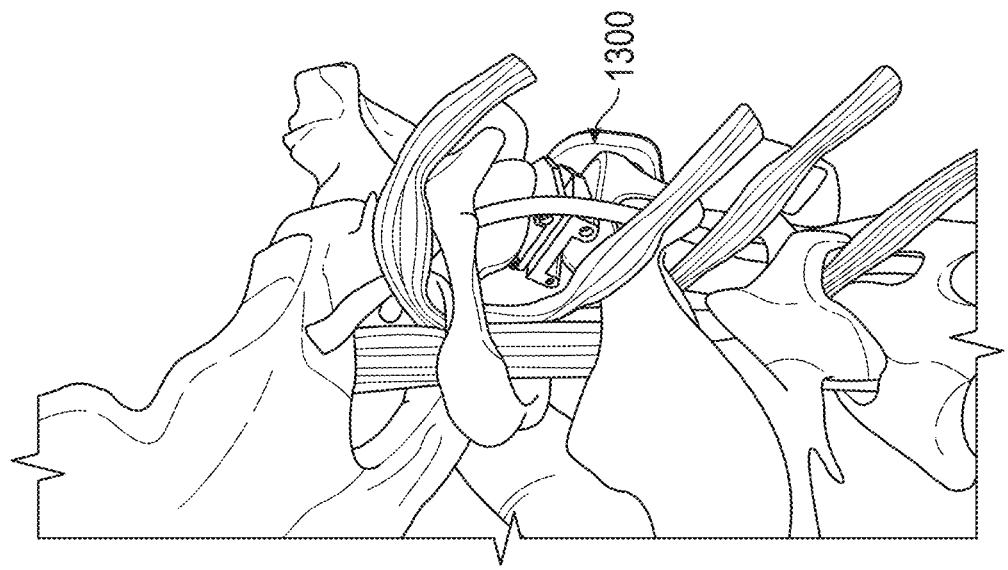
FIGS. 14A-14B illustrate the joint prosthesis shown in FIG. 13 placed in the atlanto-axial joint.
Figure 14A:
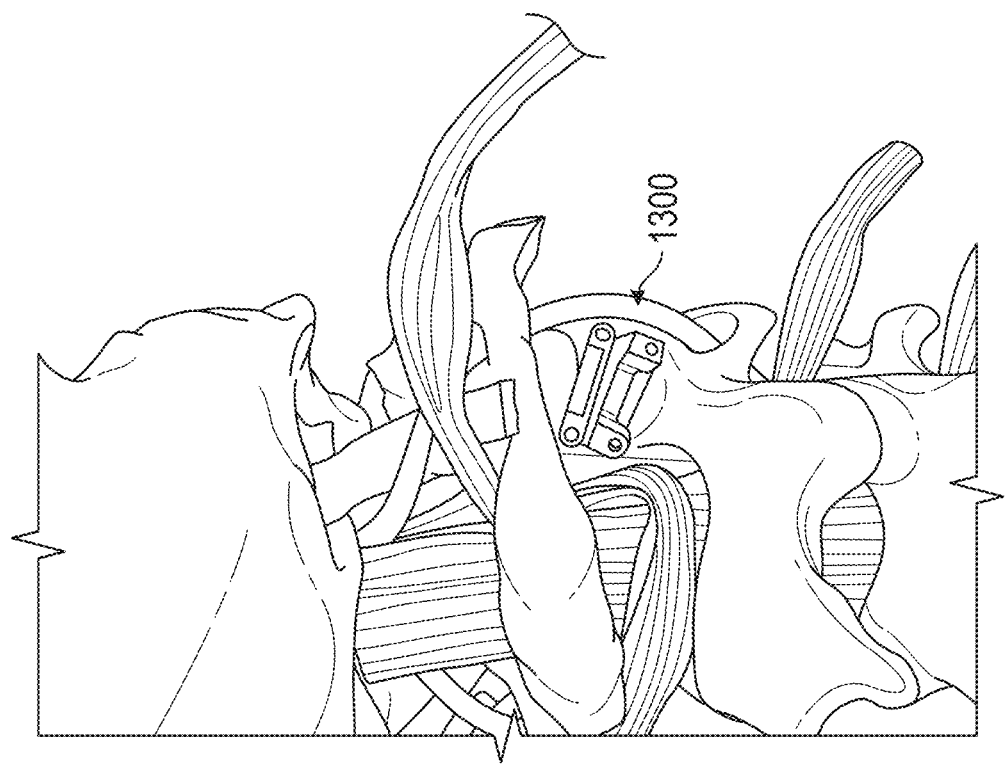

Although the prosthesis 1300 is described as being implanted in a sub-axial cervical facet joint, the prosthesis may also be placed in the atlanto-axial joint. FIGS. 14A and 14B illustrates schematically a ball-and-trough joint replacement prosthesis 1300 placed in the atlanto-axial joint.

Figure 15:
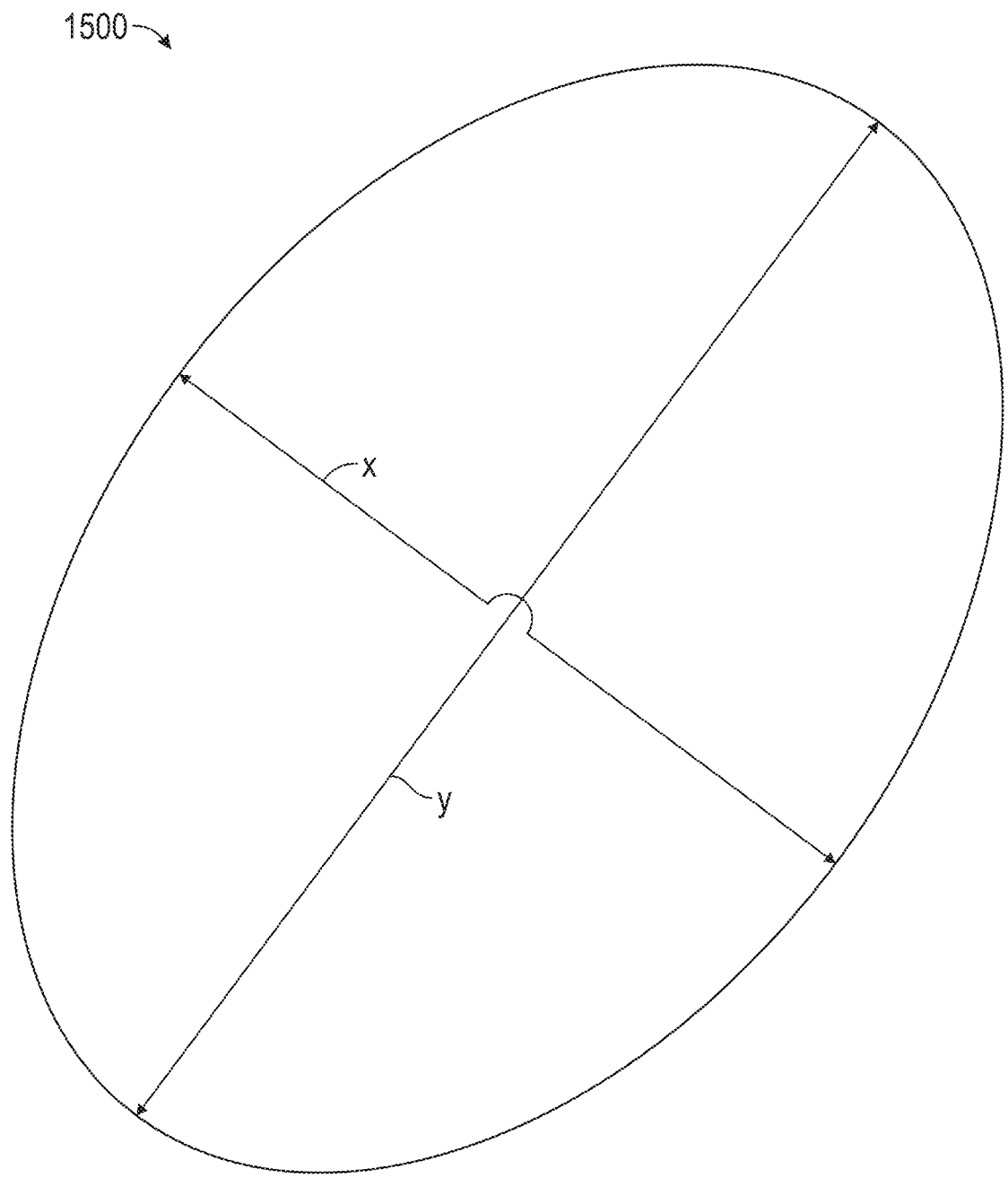
FIG. 15 illustrates a footprint of a joint prosthesis that can be placed in a sub-axial cervical facet joint.

FIG. 15 illustrates schematically a footprint of an intervertebral joint prosthesis 1500 that can be combined with any of the features of the sub-axial cervical joint prostheses described herein. In some embodiments, the prosthesis can be configured to be placed within an intervertebral joint, including but not limited to a cervical joint, such as the atlanto-axial joint. In some embodiments, the prosthesis can include a generally ovoid, or ellipsoid cross-sectional geometry. The prosthesis can include a major axis dimension y of, for example, between about 7 mm and about 13 mm, such as about 7, 8, 9, 10, 11, 12, 13 mm, or ranges including any two of the foregoing values. The prosthesis can also include a minor axis dimension x of, for example, between about 5 mm and about 12 mm, such as between about 5, 6, 7, 8, 9, 10, 11, 12 mm, or ranges including any two of the foregoing values. In some embodiments, the major axis dimension is about, at least about, or no more than about 1.25×, 1.20×, 1.19×, 1.18×, 1.17×, 1.16×, 1.15×, 1.14×, 1.13×, 1.12×, 1.11× 1.10×, 1.09×, 1.08×, 1.07×, 1.06×, 1.05×, 1.04×, 1.03×, 1.02×, 1.01×, or more or less of the minor axis dimension, including ranges including any two of the foregoing values.

Figure 16:
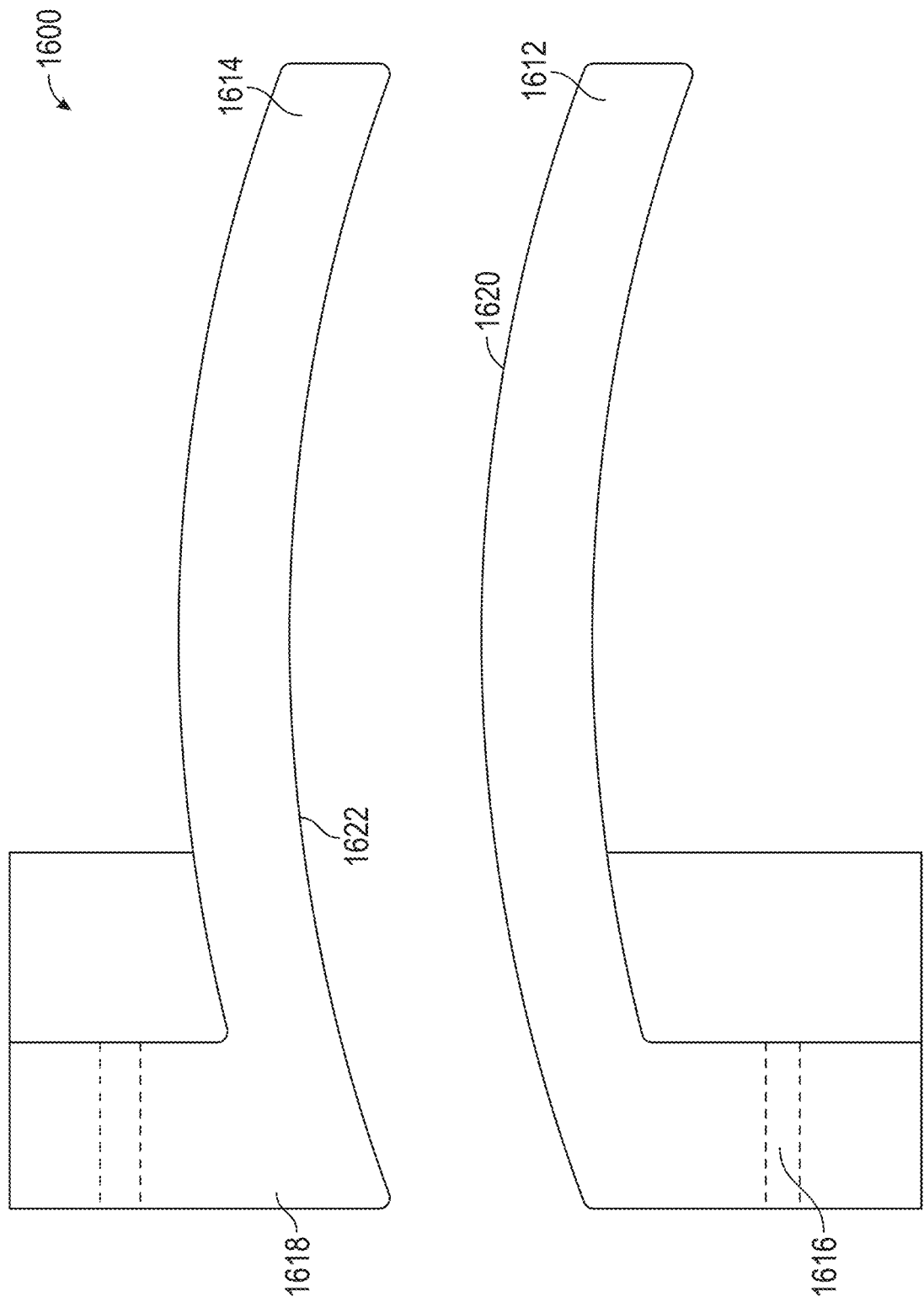
FIGS. 16-17 illustrate another joint prosthesis that can be placed in a sub-axial cervical facet joint.
Figure 17:
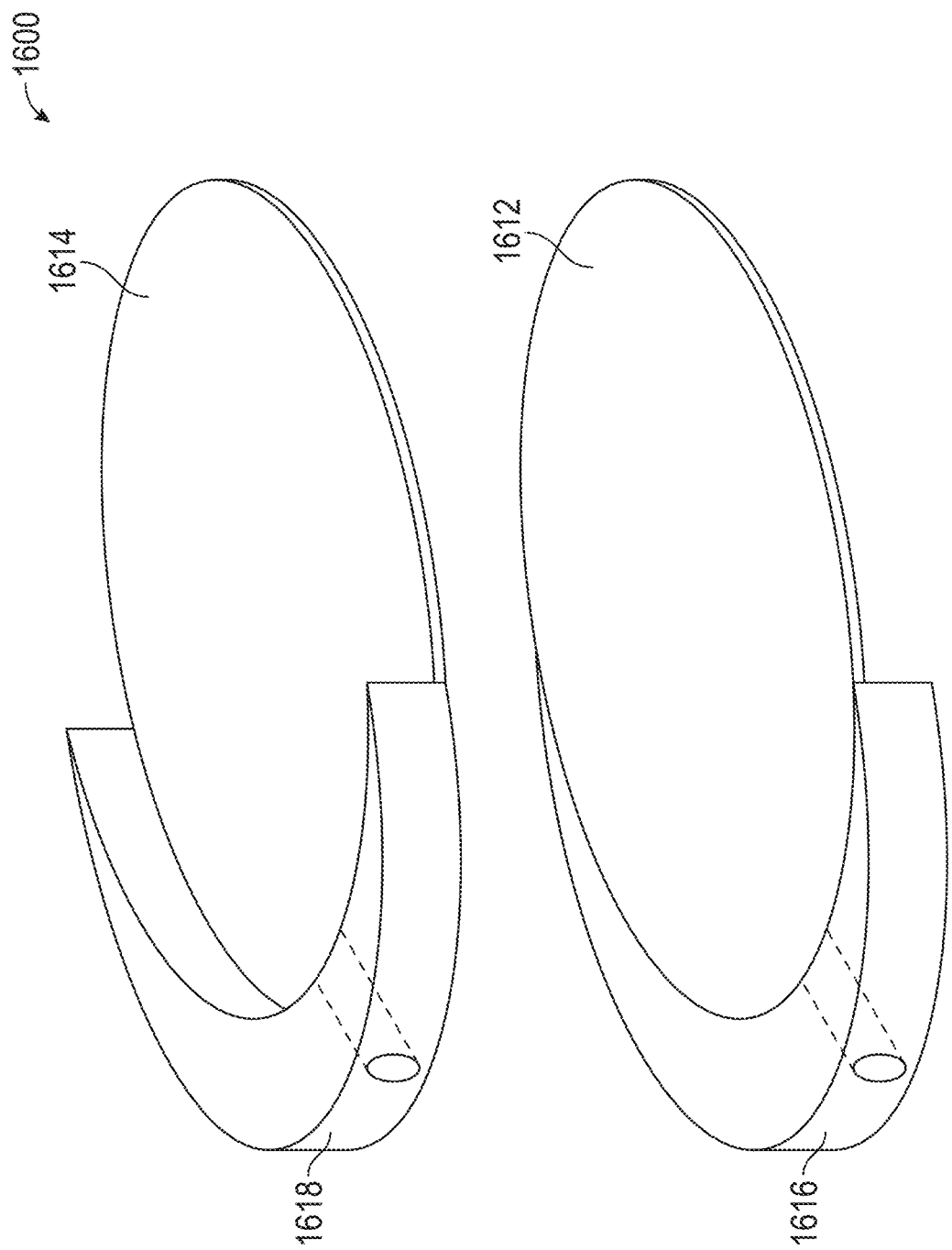

FIG. 16 illustrates schematically a side view of an embodiment of a joint replacement prosthesis 1600 (e.g., cervical vertebral facet joint replacement prosthesis, such as at C5-6 for example), including a first component 1612 configured to attach to a first vertebrae, and a second component 1614 configured to attach to a second vertebrae. The prosthesis can include a convex-concave design, with both the first component 1612 and the second component 1614 including convex and concave articulating surfaces 1620, 1622, respectively. In some embodiments, the convex and concave respective surfaces of the respective first and second components 1612, 1614 can have the same or substantially matching radii of curvature. The first component 1612 and the second component 1614 can include flanges 1616, 1618 configured for attachment to respective vertebrae, which can include any number of features described elsewhere herein. As in FIG. 17, the flanges 1616, 1618 can be generally curved, and in some cases configured to mimic the rounded surface/geometry of articular pillars of vertebrae, including adjacent cervical vertebrae. Each flange 1616, 1618 can include at least one aperture for receiving a fastener to secure the components 1612, 1614 to the respective vertebrae.

Figure 18:
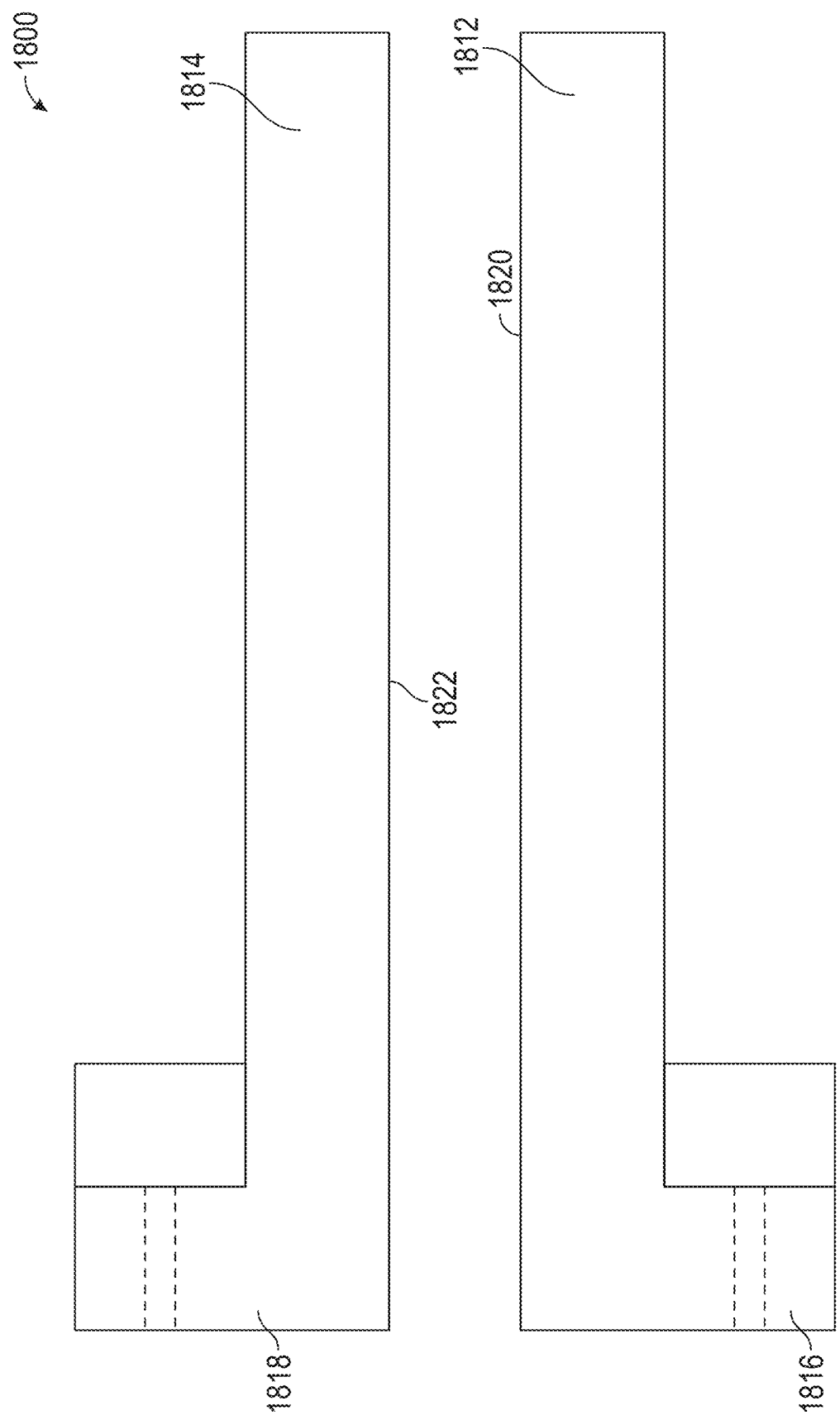
FIG. 18 illustrates another joint prosthesis that can be placed in a sub-axial cervical facet joint.

FIG. 18 illustrates schematically a side view of another embodiment of a joint replacement prosthesis 1800, including a first component 1812 configured to attach to a first vertebrae, and a second component 1814 configured to attach to a second vertebrae. The prosthesis can include features as described elsewhere herein, and in some cases the first, component 1812 includes a generally flat articulating surface 1820, while the second, component 1814 also includes a generally flat articulating surface 1822. The first component 1812 and the second component 1814 can include flanges 1816, 1818 configured for attachment to respective vertebrae, which can include any number of features described elsewhere herein.

In some embodiments, a vertebral joint replacement prosthesis, (e.g., cervical vertebral joint replacement prosthesis, such as at C1-2, C2-3, C3-4, C4-5, C5-6, C6-7, C7-T1, for example) can include any number of the following features:

A keel or coating with, for example, hydroxyapatite (e.g., nano-sized or micro-sized) and/or other osteoinductive materials to integrate with bone.

The curved fixation flange can be configured to minimize the impact on either vertebral artery or canal.

The prosthesis can be 3D printed for difficult anatomic cases.

The impact of the prosthesis can be minimized on supportive ligaments, e.g., the alar, transverse, apical, anterior longitudinal, and capsular ligaments.

The spinal nerves, spinal canal contents, and vertebral artery can be preserved during placement.

Figure 19B:
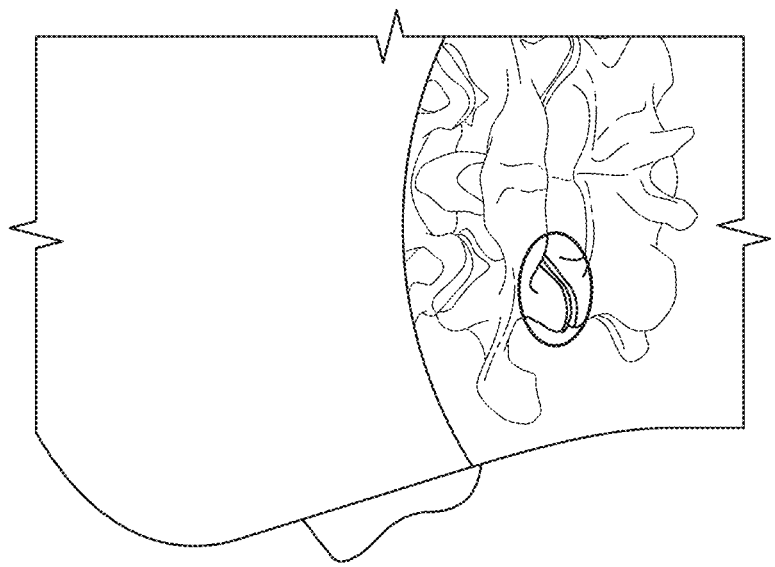
FIGS. 19A and 19B illustrate an expandable delivery device to access the mid-point of a sub-axial cervical facet joint.
Figure 19A:
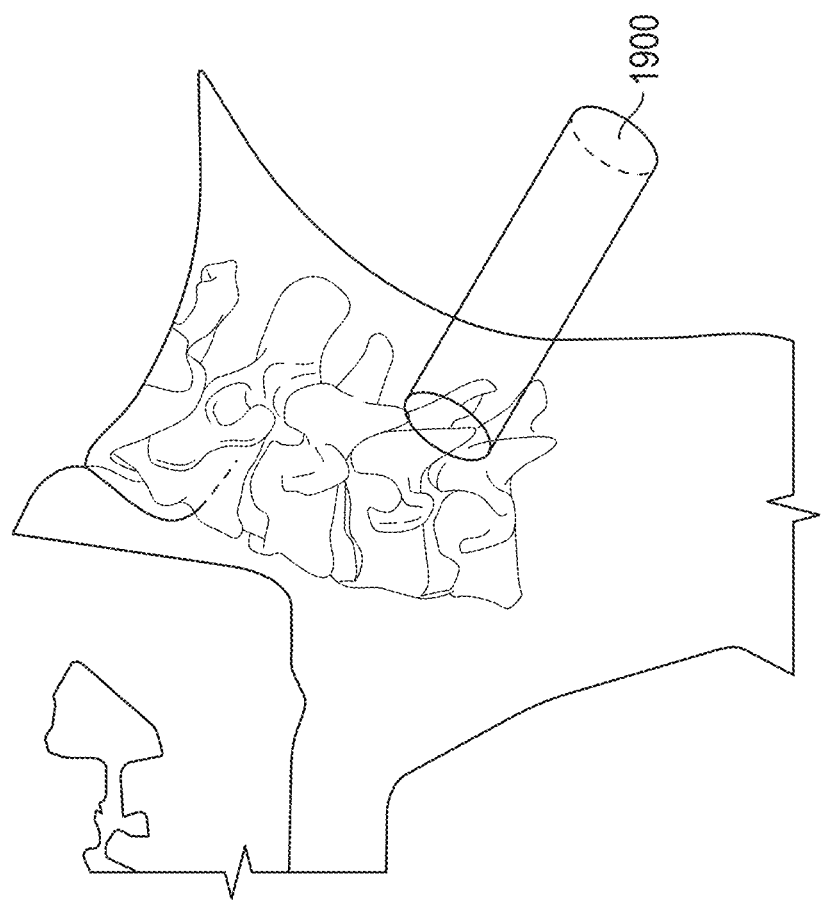

In some embodiments, a sub-axial cervical facet joint replacement prosthesis, such as placement of spinous process midway between articular pillars on fluoroscopy provides a true AP direction. Caudal tilt of a C-arm can then identify the facet joint, and defines an approach angle for placement of an expandable tube 1900 to the sub-axial facet joint, and allows placement of an expandable delivery device, such as an expandable tube to the sub-axial facet joint, as shown in FIGS. 19A and 19B. Alternatively, a guide wire can be placed fluoroscopically, and serve as initial step in tube placement using a Seldinger technique.

Figure 25A:
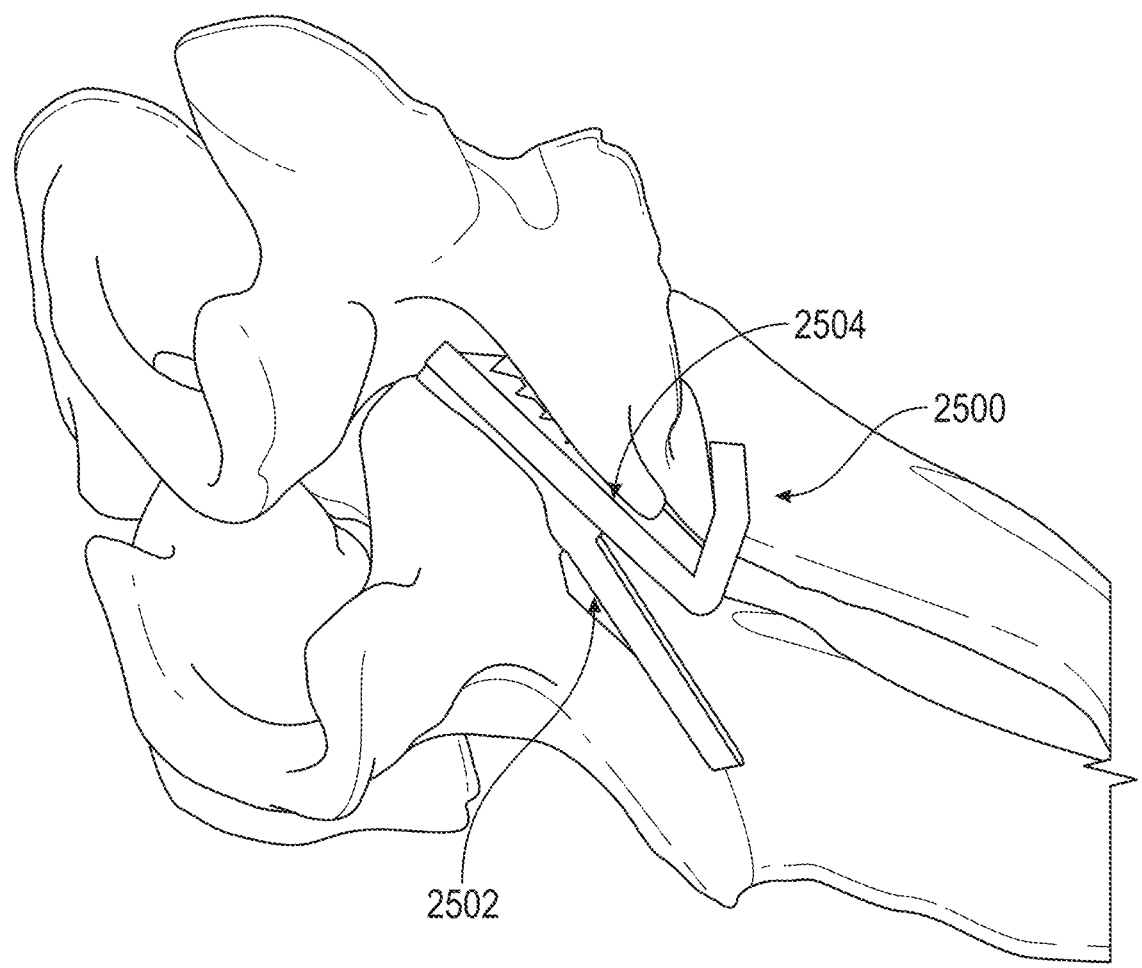

FIGS. 25A-25E illustrate another prosthesis 2500 that can be implanted anywhere from the occipito-atlantal to the sacroiliac joint. As shown in FIG. 25A, the prosthesis 2500 can include a first or trough element 2504 for placement in a first vertebrae (such as the C5 vertebrae for example), and a second or ball element 2502 for placement in a second vertebrae directly adjacent to the first vertebrae (such as the C6 vertebrae for example). The trough element 2504 can be placed on an inferior articular surface of the articular pillar of a first vertebrae, without extending into the disc space, and secured to a posterior side of the articular pillar. The ball element 2502 can be placed on a superior articular surface of the articular pillar of an adjacent, second vertebrae, without extending into the disc space, and secured to an anterior side of the articular pillar. Although the prosthesis is described with respect to features shown in FIGS. 25A-25E, the prosthesis can be combined with features of any of the other prostheses described herein.

As shown in FIG. 25B, the ball element 2502 can include a body portion 2520 with a convex surface 2506 on a first or superior side of the body portion 2520 and/or a generally flat surface 2501 on a second or inferior side of the body portion 2520. Lateral sides of the body portion 2620 can be oriented parallel to each other such that the ball element 2502 has a generally rectangular footprint. As illustrated, the convex surface 2506 is non-spherical. The convex surface 2506 can be substantially spherical, oval, oblong, or another shape in some cases. The convex surface 2506 can extend from or be surrounded by an otherwise generally flat surface 2507.

The posterior side 2503 of the body portion 2520 can include one or more flanges 2512 to secure the ball element 2502 to a posterior side of the vertebrae. The flange 2512 can extend generally away or in an opposite direction from the convex surface 2506, for example the inferior direction. The flange 2512 can be positioned at a non-zero angle relative to the generally flat surfaces 2501, 2507. The flange 2512 may be positioned at an acute angle relative to the generally flat surface 2507 surrounding the convex surface 2506, for example less than or equal to about 45 degrees, less than or equal to about 30 degrees, or less than or equal to about 15 degrees. Each of the one or more flanges 2512 can include at least one aperture 2510 configured to house bone screws therethrough to attach the ball element 2502 to a vertebrae (see FIGS. 25D and 25E), for example on a posterior side of the facet joint. For example, as illustrated, the ball element 2502 can include a single flange 2512 with a single aperture 2510. Each aperture 2510 can have a diameter at least about 1.0 mm and/or less than or equal to about 3.0 mm, for example between about 1.5 mm and 2.5 mm, or about, at least about, or no more than about 1.0, 1.5, 2.0, 2.5, or 3.0 mm or more or less, including ranges encompassing any two of the foregoing values.

The trough element 2504 can include body portion 2522 with a concave surface 2508 on a first or inferior side of the body portion 2522 (see FIG. 25C). The concave surface 2508 is configured to articulate with the convex surface 2506 of the ball element 2502. The body portion 2522 can be sufficiently thick to receive the concave surface 2508 and include a flat surface 2509 opposite the concave surface 2508 on a second or superior side (see FIG. 25B), but in other embodiments, the surface 2509 may be convex.

The posterior side 2513 of the body portion 2522 can include one or more flanges 2514 to secure the trough element 2504 to a posterior side of the vertebrae. The flange 2514 can generally extend in the same direction as the convex surface 2509 or in the superior direction. The flange 2514 can be positioned at a non-zero angle relative to the body portion 2522. The flange 2514 may be positioned at an acute angle relative to the generally flat surface 2509, for example between about 45 degrees and about 90 degrees, or between about 50 degrees and about 70 degrees. The flange 2514 can include at least one aperture 2516 configured to house bone screws therethrough to attach the trough element 2504 to a vertebrae. For example, as illustrated, the trough element 2504 can include a single flange 2514 with a single aperture 2516. Each aperture 2516 can have a diameter at least about 1.0 mm and/or less than or equal to about 3.0 mm, for example between about 1.5 mm and 2.5 mm, or about, at least about, or no more than about 1.0, 1.5, 2.0, 2.5, or 3.0 mm or more or less, including ranges encompassing any two of the foregoing values.

The convex surface 2506 and the concave surface 2508, also referred to herein as bearing surfaces, can be displaced from the flanges 2512, 2514 and positioned closer to the opposite end of each respective component 2502, 2504. For example, the bearing surfaces 2506, 2508 can be positioned closer to the anterior sides 2505, 2511 than the posterior sides 2503, 2513 of each respective component 2502, 2504.

The prosthesis 2500 may exhibit multiple degrees of freedom of movement, including axial rotation, lateral translation, anteroposterior translation, flexion-extension, and/or vertical movement. The bearing surfaces 2506, 2508 permit the ball and trough elements 2502, 2504 to move relative to each other in one or more directions, for example, the bearing surfaces 2506, 2508 may allow the ball and trough elements 2502, 2504 to bend or tilt relative to each in the anterior-posterior direction such that anterior or posterior ends of the ball and trough elements 2502, 2504 move closer together or further apart in the longitudinal direction when implanted. The bearing surfaces 2506, 2508 may allow the ball and trough elements 2502, 2504 to bend or tilt relative to each other in the medial-lateral direction such that the lateral sides of the ball and trough elements 2502, 2504 move closer together or further apart in the longitudinal direction when implanted. The bearing surfaces 2506, 2508 may allow the ball and trough elements 2502, 2504 to rotate relative to each other about a longitudinal axis of the bearing surfaces 2506, 2508, for example within a single horizontal plane when implanted.

The bearing surfaces 2506, 2508 may include any of the features or dimensions described above with respect to other prostheses. The bearing surfaces 2506, 2508 may not exactly match. For example, the length and/or the width of the concave surface 2508 can be greater than the respective dimensions of the convex surface 2506, for example at least 1.5× greater, at least 2× greater or at least 3× greater. This allows the ball element 2502 and the trough element 2504 to translate relative to each other in the anterior-posterior direction and/or the medial-lateral direction when implanted. In some configurations, the ball element 2502 may translate relative to the trough element 2504 in any direction when implanted. As illustrated, each bearing surface 2506, 2508 may have a length in the anterior-posterior direction that is greater than a width in the medial-lateral direction to permit a greater range of translation in the anterior-posterior direction compared to the medial-lateral direction, for example at least 10% greater or at least 20% greater.

FIG. 25B illustrates a perspective view of components shown in FIG. 25A. FIG. 25C illustrates a plan view of components shown in FIG. 25A. The ball element 2502 can have a length dimension 25BX in an anterior-posterior direction and a width dimension 25DX in the medial-lateral direction. The length dimension 25BX can be greater than the width dimension 25DX, for example at least 1.5× or at least 2.0×. In some embodiments, the length dimension 25BX can be, for example, between at least about 10 mm and/or less than or equal to about 25 mm, for example between 15 mm and 25 mm, or about, at least about, or no more than about 15, 16, 17, 18, 19, 20, 21, 22, 23, 24, 25 mm or more or less, including ranges encompassing any two of the foregoing values. In some embodiments, the maximum width dimension 25DX can be, for example, at least about 5 mm and/or less than or equal about 20 mm, for example between 5 mm and 10 mm, or about, at least about, or no more than about 5, 6, 7, 8, 9, 10, 11, 12, 13, 14, 15 mm or more or less, including ranges encompassing any two of the foregoing values. The ball element 2502 can have a constant width 25DX from an anterior side 2505 to a posterior side 2503, although in other embodiments, a width of the flange 2512 may be reduced compared to a remainder of the body portion 2520.

The trough element 2504 can include a length dimension 25GX in the anterior-posterior direction and a width dimension 25HX in the medial lateral direction (annotated on FIG. 25D). The length dimension 25GX of the trough element 2504 can be less than or equal to the length dimension 25BX of the ball element 2502. In some embodiments, the length dimension 25GX can be, for example, at least about 10 mm and/or less than or equal to about 25 mm, for example between about 10 mm and about 15 mm, or about, at least about, or no more than about 10, 11, 12, 13, 14, 15, 16, 17, 18, 19, 20, 21, 22, 23, 24, 25 mm or more or less, including ranges encompassing any two of the foregoing values. The maximum width dimension 25HX of the trough element 2504 can be about the same as maximum width dimension 25DX of the ball element 2502. In some embodiments, the width dimension 25HX can be, for example, at least about 5 mm and/or less than or equal about 20 mm, for example between 5 mm and 10 mm, or about, at least about, or no more than about 5, 6, 7, 8, 9, 10, 11, 12, 13, 14, 15 mm or more or less, including ranges encompassing any two of the foregoing values. The trough element 2504 can have a constant width 25HX from an anterior side 2511 to a posterior side 2513, although in other embodiments, a width of the flange 2514 may be reduced compared to a remainder of the body portion 2522.

The body portion 2520 of the ball element 2502 can have a thickness dimension 25NX between the generally flat surface 2507 on the first side and the generally flat surface 2501 on the second side. In some embodiments, the thickness dimension 25NX can be, for example, at least about 0.5 mm and/or less than or equal to about 2 mm, or between 0.5 mm and 1.5 mm, or about, at least about, or no more than about 0.5, 0.6, 0.7, 0.8, 0.9, 1.0, 1.1, 1.2, 1.3, 1.4, 1.5, 1.6, 1.7, 1.8, 1.9, 2.0 mm or more or less, including ranges encompassing any two of the foregoing values. The body portion 2520 have the same thickness from the anterior side 2505 to the posterior side 2503.

The body portion 2522 of the trough element 2504 can have a maximum thickness dimension 250X between flat surfaces on opposite sides of the trough element 2504 and surrounding the concave surface 2508. The thickness dimension 250X can be less than or equal to the thickness dimension 25NX of the body portion 2520. In some embodiments, the thickness dimension 25NX can be, for example, at least about 0.5 mm and/or less than or equal to about 2 mm, or between 0.5 mm and 1.5 mm, or about, at least about, or no more than about 0.5, 0.6, 0.7, 0.8, 0.9, 1.0, 1.1, 1.2, 1.3, 1.4, 1.5, 1.6, 1.7, 1.8, 1.9, 2.0 mm or more or less, including ranges encompassing any two of the foregoing values. The body portion 2522 be thicker at the anterior side 2511 compared to the posterior side 2513, but in other configurations, may have a constant thickness.

One or both of the ball element 2502 and trough element 2504 can have one or more anchoring elements 2552, 2550 on the respective body portions 2520, 2522 to anchor the components to superior or inferior surfaces of the vertebrae. Additionally or alternatively, the ball element 2502 and the trough element 2504 may be secured by an expandable anchor having any of the features of the anchoring elements 2750, 2852, 2850 described below. For example, expandable anchors may be advanced through the apertures in the flanges 2512, 2514 to secure the prosthesis.

In some embodiments, the prosthesis or any element thereof can comprise a biocompatible material, such as a metal such as titanium, for example. Each of the ball element 2502 and the trough element 2504 can be a monolithic element. Although, in some embodiments, the anchoring elements 2552, 2550 may be separately attached to the respective body portions 2520, 2522.

The ball element 2502 can have one or more anchoring elements 2552 opposite the convex surface 2506, for example extending along the body portion 2520 on the second or inferior side of the ball element 2502. The anchoring elements 2552 can extend from the anterior side 2505 to the flange 2512. The anchoring elements 2552 can include surface features to promote or inhibit bony ingrowth. Each anchoring element 2552 can be a keel with one or more saw teeth, for example a linear array of saw teeth. The linear array of saw teeth may extend in any direction, for example the anterior-posterior direction, the medial-lateral direction, parallel to the major axis of the convex surface 2506, or parallel to the minor axis of the convex surface 2506. The ball element 2502 can include two anchoring elements 2552 spaced apart from each other. The anchoring elements 2552 can extend in the anterior-posterior direction along lateral sides of the ball element 2502. Each anchoring element 2552 can be positioned laterally outward from the convex surface 2506. The anchoring elements 2552 can be spaced apart from the convex surface 2506 in the lateral direction. Each anchoring element can have a width dimension in the medial-lateral direction of less than or equal to about 3 mm, less than or equal to about 2 mm, or less than or equal to about 1 mm. In other configurations, the anchoring elements 2552 may extend in the medial-lateral direction or be angled relative to each other, for example toe-in.

The trough element 2504 can have one or more anchor elements 2550 opposite the concave surface 2508, for example along the body portion 2522 on the second or superior side of the trough element 2504. The anchor elements 2550 can extend from the anterior side 2511 to the flange 2514. The anchoring elements 2550 can include surface features to promote or inhibit bony ingrowth. Each anchoring element 2550 can be a keel with one or more saw teeth, for example a linear array of saw teeth. The linear array of saw teeth may extend in any direction, for example the anterior-posterior direction, the medial-lateral direction, parallel to the major axis of the concave surface 2508, or parallel to the minor axis of the concave surface 2508. As illustrated, the trough element 2504 can include two anchoring elements 2550 spaced apart from each other. The anchoring elements 2550 can extend in the anterior-posterior direction along lateral sides of the trough element 2504. Each anchoring element 2550 can be positioned laterally outward from the concave surface 2508. Each anchoring element can have a width dimension in the medial-lateral direction of less than or equal to about 3 mm, less than or equal to about 2 mm, or less than or equal to about 1 mm. In other configurations, the anchoring elements 2550 may extend in the medial-lateral direction or be angled relative to each other, for example toe-in.

The convex surface 2506 can have a length dimension 25CX in the anterior-posterior direction, a width dimension 25AX in the medial-lateral direction, and a thickness dimension 25IX in the superior-inferior direction. The length dimension 25CX can be greater than or equal to the width dimension 25AX and the thickness dimension 25IX. The width dimension 25AX can be greater than or equal to the thickness dimension 25IX. The length dimension 25CX can be at least about 10%, at least about 20%, at least about 30%, at least about 40%, or at least about 50% longer than the width dimension 25AX or the thickness dimension 25IX. In some embodiments, the width dimension 25AX can be, for example, at least about 2 mm and/or less than or equal to about 12 mm, for example between about 3 mm and about 6 mm, or about, at least about, or no more than about 2, 3, 4, 5, 6, 7, 8, 9, 10, 11, or 12 mm or more or less, including ranges encompassing any two of the foregoing values. In some embodiments, the length dimension 25CX can be between about 2 mm and about 12 mm, for example between about 4 mm and about 8 mm, or about, at least about, or no more than about 2, 3, 4, 5, 6, 7, 8, 9, 10, 11, or 12 mm or more or less, including ranges encompassing any two of the foregoing values. In some embodiments, the thickness dimension 25IX can be, for example, between about 1 mm and about 5 mm, or about, at least about, or no more than about 1, 1.5, 2, 2.1, 2.2, 2.3, 2.4, 2.5, 2.6, 2.7, 2.8, 2.9, 3, 3.5, 4 mm or more or less, including ranges encompassing any two of the foregoing values. The flange 2512 extends further in the inferior direction than the convex surface 2506 extends in the inferior direction.

The concave surface 2508 of the trough element 2504 can have a length dimension 25FX in the anterior-posterior direction, a width dimension (not marked) in the medial-lateral direction, and a thickness dimension 25MX in the superior-inferior direction. The length dimension 25FX can be greater than or equal to the width dimension or the thickness dimension 25MX. The width dimension can be greater than or equal to the thickness dimension 25IX. The length dimension 25FX can be at least about 10%, at least about 20%, at least about 30%, at least about 40%, or at least about 50% longer than the width dimension or the thickness dimension 25MX. In some embodiments, the width dimension can be, for example, at least about 2 mm and/or less than or equal to about 12 mm, for example between 8 mm and 12 mm, or about, at least about, or no more than about 2, 3, 4, 5, 6, 7, 8, 9, 10, 11, or 12 mm or more or less, including ranges encompassing any two of the foregoing values. In some embodiments, the length dimension 25FX can be between about 2 mm and about 12 mm, for example between about 8 mm and about 12 mm, or about, at least about, or no more than about 2, 3, 4, 5, 6, 7, 8, 9, 10, 11, or 12 mm or more or less, including ranges encompassing any two of the foregoing values. In some embodiments, the thickness dimension 25MX can be, for example, between about 0.5 mm and about 5 mm, or about, at least about, or no more than about 0.5, 0.75, 1, 1.5, 2, 2.1, 2.2, 2.3, 2.4, 2.5, 2.6, 2.7, 2.8, 2.9, 3, 3.5, 4 mm or more or less, including ranges encompassing any two of the foregoing values. The thickness dimension 25MX can be less than the thickness dimension 25IX and/or the thickness dimension 25OX of the body portion 2522.

FIG. 25E illustrates a posterior side of the trough element 2504 and an anterior side of the ball element 2502.

Although certain features are described with respect to the ball element 2502 or trough element 2504, any of the features described herein are interchangeable between the two elements 2502, 2504. For example, the ball feature could be on the inferior side of a first element and the trough could be on the superior side of a second element.

Certain prostheses are described with respect to sub-axial cervical joints, but could be placed between any of the other cervical or thoracic facet joints.

Occipito-Atlantal

FIGS. 20A-20E illustrate various views of another embodiment of a ball-and-trough prosthesis 2000 according to some embodiments configured to form an artificial occipito-atlantal prosthesis, including a superior occipital component including a male ball element 2002, and an inferior C1 component including a female trough element 2004.

Figure 20A:
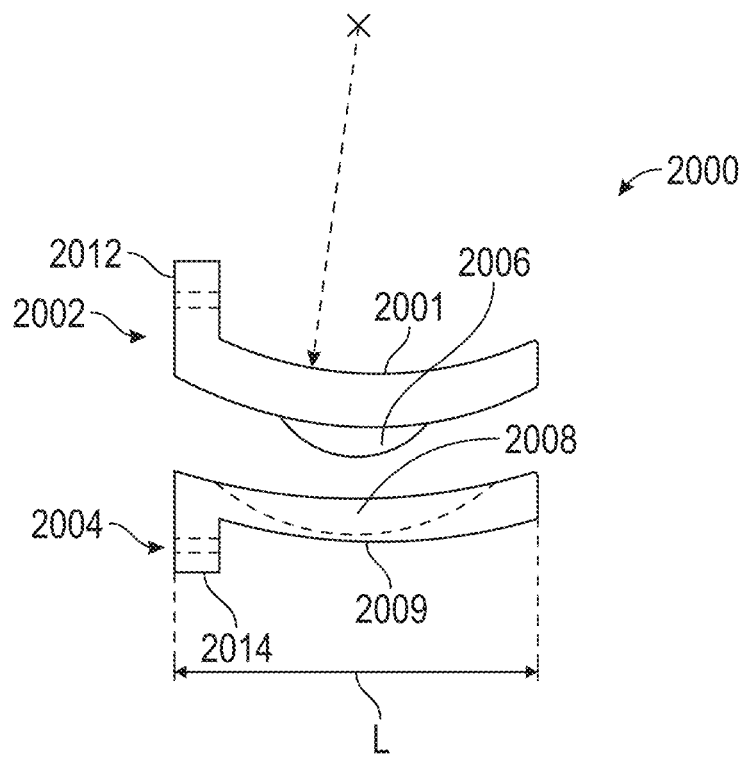
FIGS. 20A-20E illustrate a joint prostheses that can be placed in the occipito-atlantal joint.
Figure 20B:
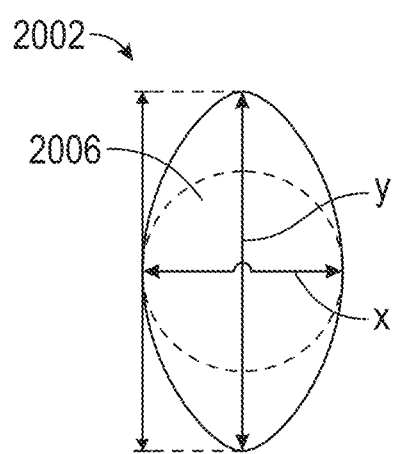
Figure 20D:
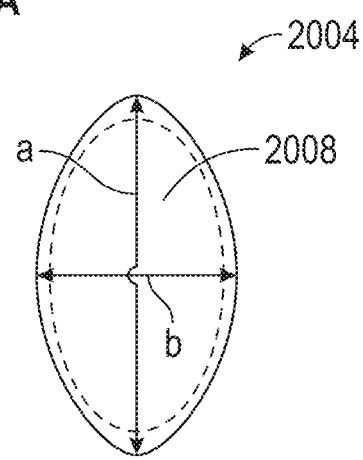
Figure 20C:
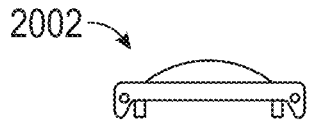
Figure 20E:
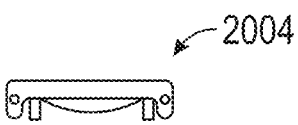
Figure 20F:
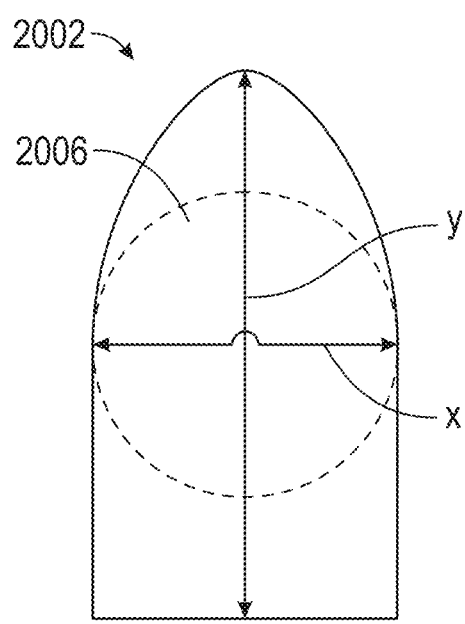
FIGS. 20F-20G illustrate another joint prostheses that can be placed in the occipito-atlantal joint.
Figure 20G:
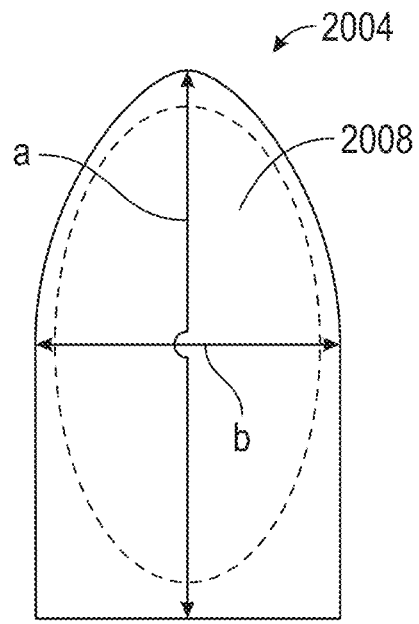

The prosthesis 2000 can include any of the ball and trough features of the earlier described prostheses, but the elements can be shaped to accommodate the anatomy of the occipito-atlantal joint. For example, the bone contacting surfaces 2001, 2009 can be shaped to match the contours of the occipito-atlantal facet joint. The flanges 2012, 2014 can be shaped to match the posterior facing side of the occipito-atlantal facet joint. As one non-limiting example, the ball element 2002 and/or the trough element 2004 can have a length L of no more than about 2 cm. The occipital component 2002 can have an arc length of about 5 cm and an arc radius of about 60 degrees in one non-limiting embodiment. The occipital component 2002 can have a major axis dimension y of no more than about 2 cm, and a minor axis dimension x of no more than about 1 cm in some embodiments. The C1 component can have a major axis dimension a of no more than about 1.8 cm and a minor axis dimension b of no more than about 1 cm in some embodiments. Either of both of the occipital component 2002 and the C1 component 2004 can have an ovoid or ellipsoid geometry as illustrated, or truncated with a flat square or rectangular end as illustrated in FIGS. 20F and 20G.

Figure 20H:
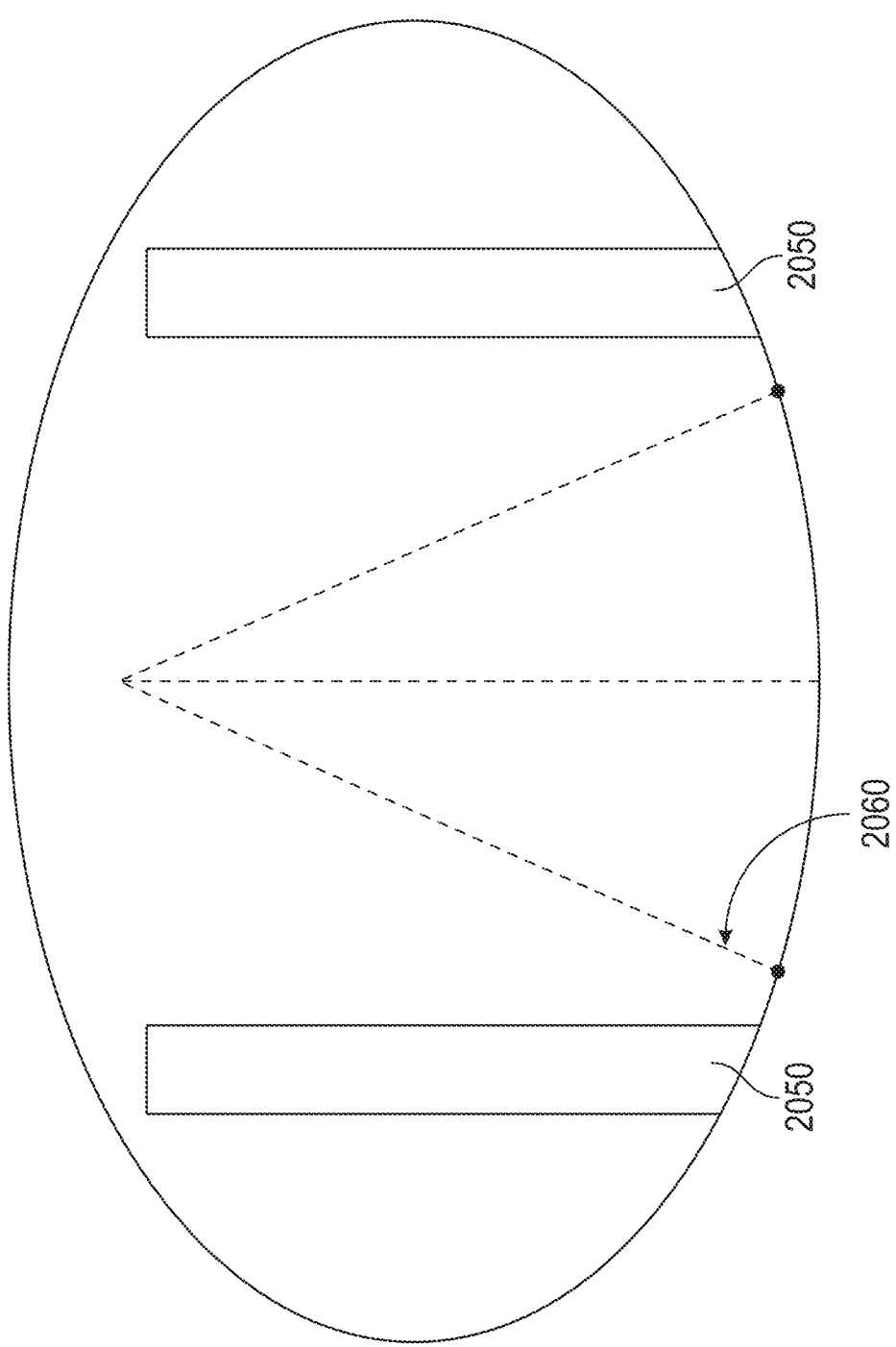
FIG. 20H illustrates anchoring elements for a joint prostheses that can be placed in the occipito-atlantal joint.

As illustrated in FIG. 20H, anchoring elements 2050 such as keels can be placed along the major axis (length) or minor axis (width) of each component of the system. In some embodiments, if the anchoring elements 2050, e.g., keels extend along the minor axis (width) of each component, one or more screws can be placed inward of the keels along one or more of the illustrated dotted paths 2060 and allowed to toe-in for greater pull-out strength.

FIGS. 20I-20M illustrates another embodiment of an artificial occipito-atlantal prosthesis that can include any number of features of the systems of FIGS. 20A-20E but does not comprise a ball element or trough feature.

Figure 20N:
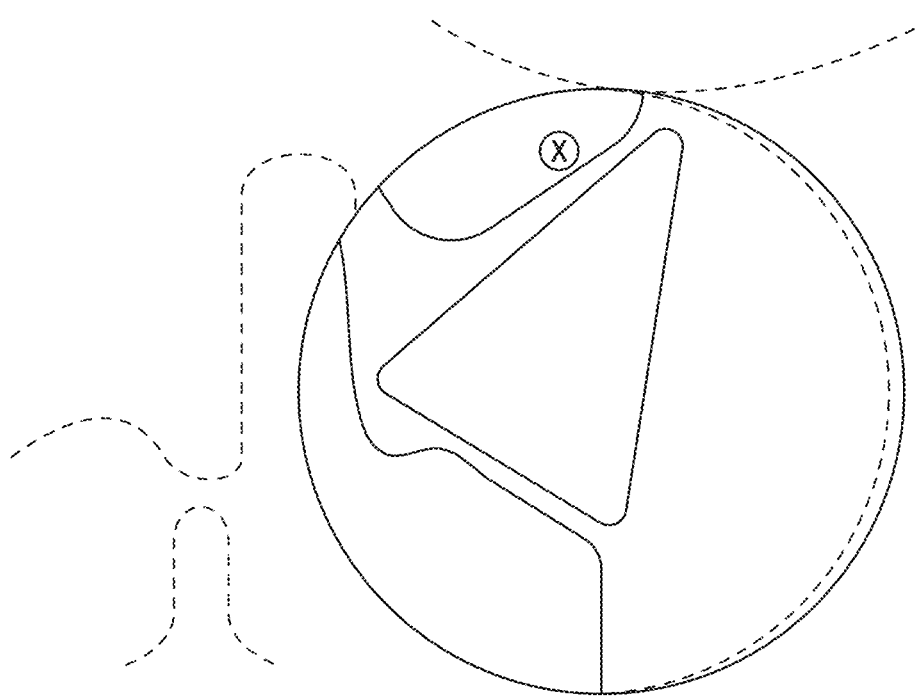
FIG. 20N illustrates a target location for a joint prosthesis that can be placed in the occipito-atlantal joint.

A minimally invasive approach to install an artificial occipito-atlantal (OA) prosthesis will now be described, according to some embodiments. In the prone position, the head is rotated slightly contralateral to target, and slightly flexed. With fluoroscopy, the bifid spinous process of C2 is placed to bisect the dens. The C-arm is rotated, for example, about 25-30 degrees ipsilateral oblique. This angle places the approach in line with the long axis of the joint (in some cases, about 28 degrees oblique) and minimizes injury to the greater occipital nerve. The OA joint will appear medial to the mastoid process and immediately beneath the occipital brim. The target can be, for example, 1-2 mm superior to the visualized OA joint line just inside it most lateral margin as illustrated schematically in FIG. 20N.

The target is slightly above the visualized joint line, because the visualized joint line actually represents the anterior aspect of the OA joint, which is more inferior than the posterior aspect of the joint. The K-wire preferably does not deviate medially or inferiorly in some embodiments, and a relatively safe direction of deviation is toward the occiput superiorly. When osseous contact is perceived, the C-arm is rotated to approximately 25 degrees contralateral oblique view. This view best reveals the K-wire orientation with respect to the most posterior aspect of the OA joint. Alternating between this contralateral and ipsilateral oblique views can allow K-wire readjustment within the joint optimally in some embodiments.

Figure 27E:
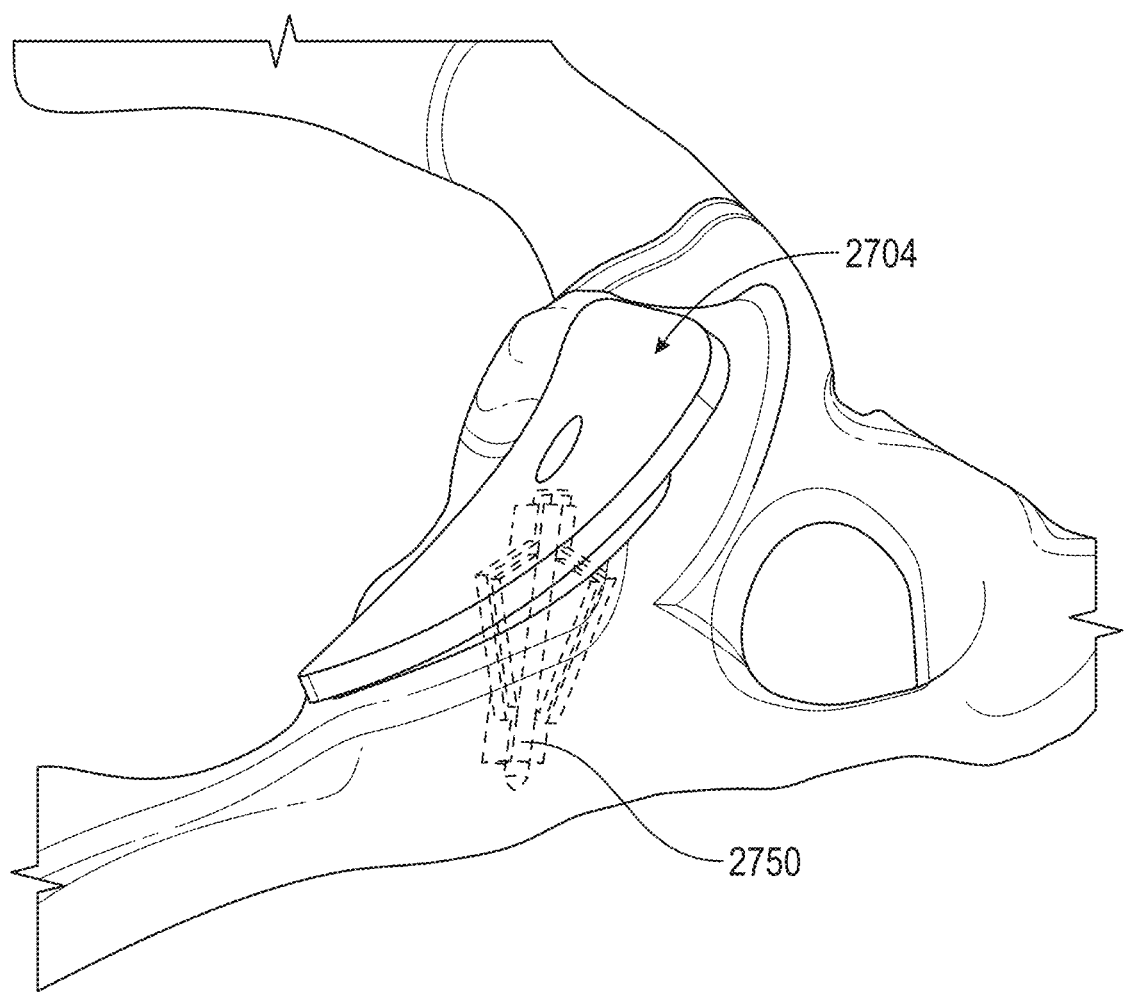
Figure 27F:
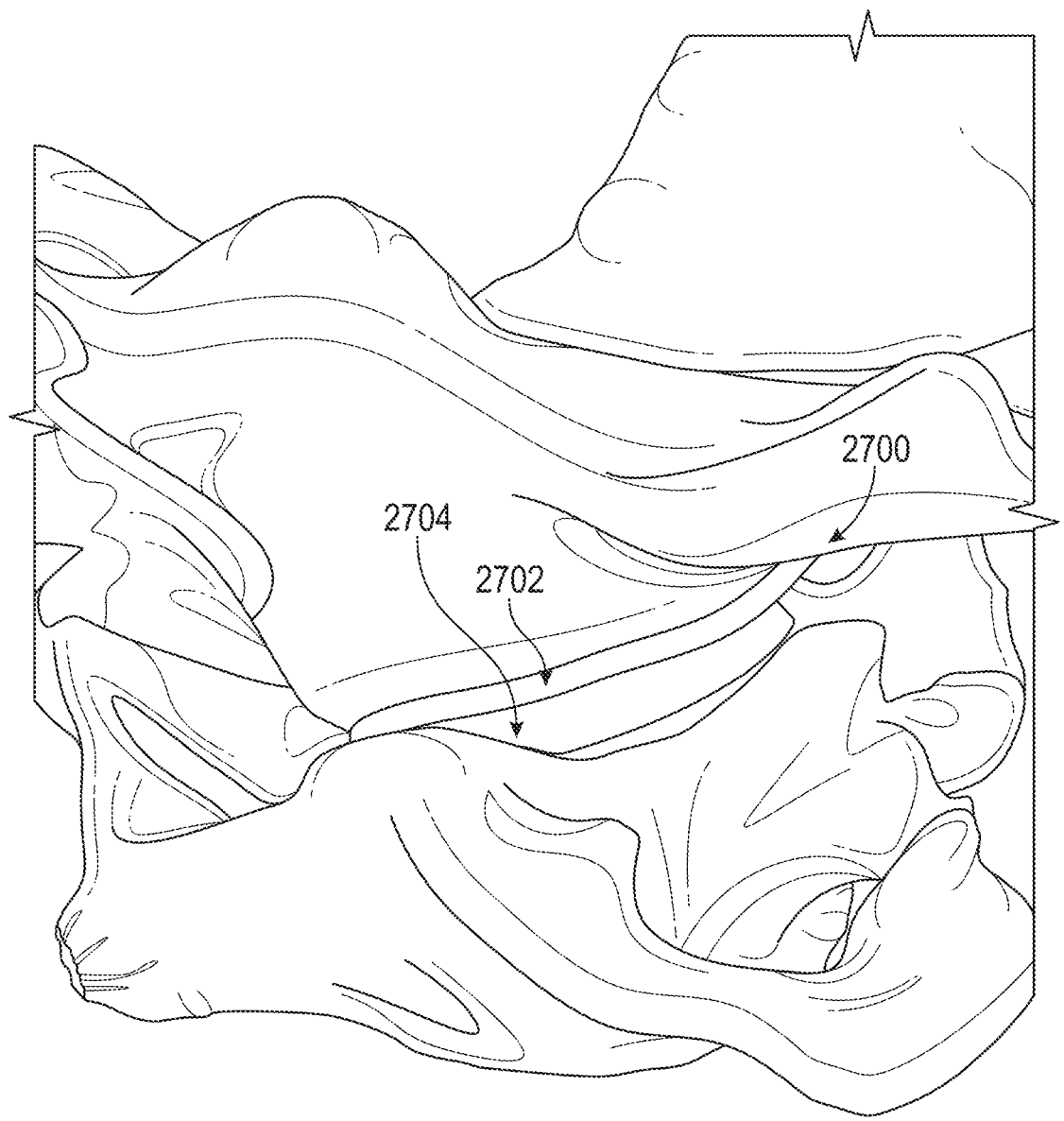

FIGS. 27A-27F illustrate another joint prosthesis 2700 that can be placed in the occipito-atlantal joint. The joint prosthesis 2700 can include a first component 2702 and a second component 2704. The first component 2702 can be attached to the occipital bone and the second component 2704 can be attached to the atlas bone (see FIG. 27F). The prosthesis 2700 can be positioned entirely within the facet joint between the occipital and atlas without extending over the rim of the facet joint or to a posterior side of the facet joint. As shown in FIG. 27E, the second component 2704 is positioned entirely on the superior articular facet. The second component 2704 can be secured using an anchoring element 2750. The anchoring element 2750 extends through the superior and inferior surfaces of the second component 2704. The anchoring element 2750 extends at an angle relative to a superior-inferior axis of the atlas bone.

As shown in FIGS. 27A-27D, the first component 2702 can have a concave articular surface 2706 and a convex bone facing surface 2708. Unlike other embodiments described in, the concave articular surface 2706 does not have a ball or trough element. The concave articular surface 2706 can have a generally smooth surface contoured to articulate relative to the second component 2704, for example the two components 2702, 2704 may slide relative to each other in different directions, for example in the anterior-posterior direction or the medial-lateral direction. The concave articular surface 2706 and the convex bone facing surface 2708 may rotated relative to each other, but may not tilt relative to each other. The bone facing surface 2708 may include surface modifications to promote bone integration.

The first component 2702 has a first end 2710 and a second end 2712. As shown in FIGS. 27A-27B, the first end 2710 may have a different profile or curvature compared the second end 2712, for example the first component 2702 may be wider at the first end 2710 than the second end 2712. A maximum width of the first component 2702 may be at the first end 2710 and/or a minimum width of the first component 2702 may be at the second end 2712. The maximum width may be no more than 10 mm, no more than 9 mm, or no more than 8 mm. A length of the first component 2702, measured from the first end 2710 to the second end 2712, may be no more than about 25, 24, 23, 22, 21, 20, 19, or 18 mm, or more or less, including ranges encompassing any of two of the foregoing values. A length of the first component 2702 may be at least 1.5×, at least 2.0×, or at least 2.5× the maximum width of the first component 2702.

As shown in FIG. 27D, the first component 2702 can have a generally constant thickness. A thickness between the articular surface 2706 and the bone-facing surface 2708 may be no more than about 2 mm, no more than about 1.5 mm, or no more than about 1.0 mm. In other configurations, the thickness may vary along the length of the first component 2702.

The first component 2702 may be asymmetrical about the superior-inferior axis. As shown in FIG. 27D, when viewing the lateral side of the first component 2702, the portion near the first end 2710 may have a smaller radius of curvature compared to the portion near the second end 2712. The first component 2702 may also exhibit different curvatures about an anterior-posterior axis, extending through the first end 2710 and the second end 2712, and/or a medial-lateral axis. As shown in FIG. 27C, the first end 2710 may be oriented in a direction that is oblique to the superior-inferior axis. When viewed from the first end 2710 or the second end 2712, the first end 2710 may be offset from the second end 2712.

The first component 2702 may be secured to bone using a fastener, for example a bone screw or an expandable screw as described elsewhere herein. The first component 2702 may have an aperture 2722 closer to the first end 2710 than the second end 2712, for example within 2 mm or within 1 mm of the first end 2710. The aperture 2722 can be configured to house the fastener therethrough.

The second component 2704 can have a concave articular surface 2714 and a convex bone facing surface 2716. Unlike other embodiments described in, the concave articular surface 2714 does not have a ball or trough element. The concave articular surface 2714 can have a generally smooth surface contoured to articulate with the first component 2702. The bone facing surface 2716 may include surface modifications to promote bone integration.

The second component 2704 has a first end 2718 and a second end 2720. As shown in FIGS. 27A-27B, the first end 2718 may have a different profile or curvature compared the second end 2720, for example the second component 2704 may be wider at the first end 2718 than the second end 2720. A maximum width of the second component 2704 may be at the first end 2718 and/or a minimum width of the second component 2704 may be at the second end 2720. The maximum width may be no more than 10 mm, no more than 9 mm, or no more than 8 mm. A length of the second component 2704, measured from the first end 2718 to the second end 2720, may be no more than about 25, 24, 23, 22, 21, 20, 19, or 18 mm, more or less, including ranges encompassing any of two of the foregoing values. A length of the second component 2704 may be at least 1.5×, at least 2.0×, or at least 2.5× the maximum width of the first component 2702.

As shown in FIG. 27D, the second component 2704 can have a varying thickness along a length of the second component 2704. A thickness at any region between the articular surface 2714 and the bone-facing surface 2716 can be no more than about 3 mm, no more than about 2.5 mm, no more than about 2 mm, no more than about 1.5 mm, or no more than about 1.0 mm. A maximum thickness may be in regions spaced apart from the first end 2718 and/or the second end 2720. A maximum thickness may be at least 1.5× or at least 2× than a thickness at the first end 2718 and/or at the second end 2720.

The second component 2704 may be asymmetrical about the superior-inferior axis. As shown in FIG. 27D, when viewing the lateral side of the second component 2704, the portion near the first end 2718 may have a smaller radius of curvature compared to the portion near the second end 2720. The second component 2704 may also exhibit different curvatures about an anterior-posterior, extending through the first end 2718 and the second end 2720, and/or about a medial-lateral axis. As shown in FIG. 27C, the first end 2718 may be oriented in a direction that is oblique to the superior-inferior axis. When viewed from the first end 2718 or the second end 2720, the first end 2718 may be offset from the second end 2720.

The second component 2704 may be secured to bone using a fastener, for example a bone screw or an expandable screw as described elsewhere herein. The second component 2704 may have an aperture closer to the first end 2718 than the second end 2720, but the aperture 2724 may be spaced further apart from the end compared to the first component 2702. The aperture 2724 may be at least 2 mm, at least 3 mm, at least 4 mm, or at least 5 mm from the first end 2718. The aperture 2724 can be configured to house the fastener therethrough (see FIG. 27E). The aperture 2724 may not extend directly through the articular surface 2714 to the bone facing surface 2716 along a longitudinal axis. As shown in FIGS. 27A-27B, an axis extending through the entrance and exit of the aperture 2724 may be oblique to a superior-inferior axis.

Each of the first component 2702 and/or the second component 2704 may be secured by anchoring elements described herein, for example the anchoring elements 2852, 2850 described below with respect to prosthesis 2800. With reference to FIG. 27E, an example of a deployed anchoring element 2750 is shown. The anchoring element 2750 may extend through the articulating surface and the bone facing surface of the second component 2704.

A length of the anchoring element 2750 can be less than or equal to about 20 mm, 16 mm, 12.5 mm, 10 mm, 7.5 mm, 5 mm, more or less, including ranges encompassing any of two of the foregoing values. The anchoring element 2750 may be expandable within the bone. For example, the anchoring element 2750 may transition from a non-deployed configuration to a deployed configuration. In the deployed configuration, the anchoring element 2750 may expand at least 1.2×, at least 1.5×, or at least 2.0× the width of the anchoring element 2750 in the undeployed configuration. When unexpanded, the anchoring element 2750 can have a width of no more than about 4 mm, 3 mm, 2 mm, more or less, including ranges encompassing any of two of the foregoing values. When expanded, the anchoring element 2750 can have a width of at least 4 mm and/or less than or equal to about 6 mm, more or less, including ranges encompassing any of two of the foregoing values.

Although certain features are described with respect to the first component 2702 or second component 2704, any of the features described herein are interchangeable between the two elements 2702, 2704.

Thoracic

Figure 21:
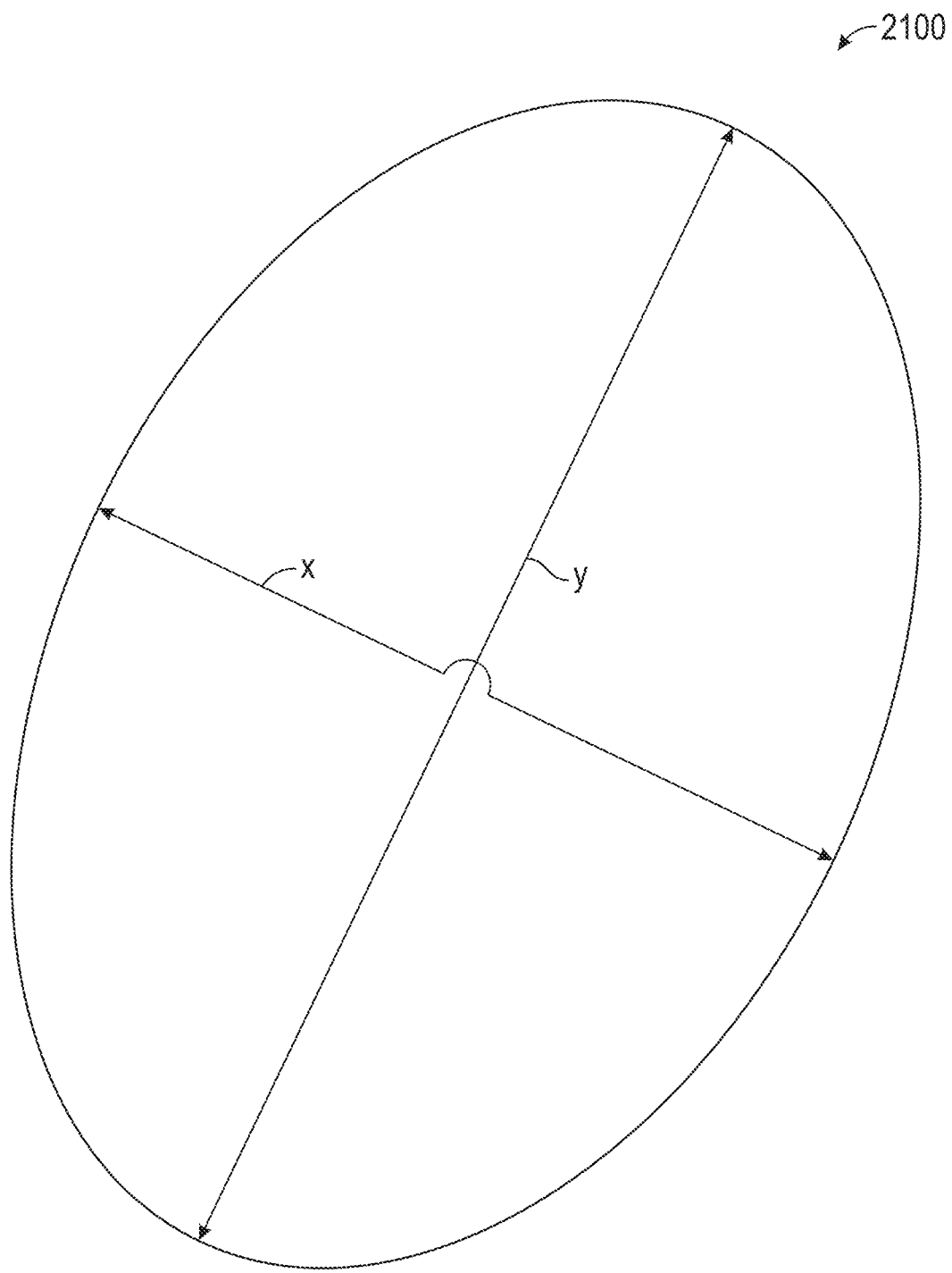
FIG. 21 illustrates a profile of a joint prosthesis that can be placed in a thoracic facet joint.

In some embodiments, systems and methods as disclosed herein, for example any of the above-described prostheses, can be used or modified, e.g., resized, for use as a thoracic facet joint prosthesis. Between T2 and T11, an ovoid footprint device 2100 of, for example, about 11 (y dimension)× 10 mm (x dimension) should approximate joint size, which is very close in size to cervical facet joint footprint at C5-6 (about 9×10 mm). One non-limiting example device footprint is shown in FIG. 21. A thoracic facet joint prosthesis can include any number of features as disclosed elsewhere herein, including ball-and-trough components, for example. Designs for subaxial cervical facet joint prosthesis can, in some embodiments, approximate thoracic facet joint prosthesis. Any number of the T1, T2, T3, T4, T5, T6, T7, T8, T9, T10, T11, and/or T12 prostheses can be treated with systems and methods as disclosed herein.

Lumbar

In some embodiments, systems and methods as disclosed herein can be used or modified for use as a lumbar facet joint prosthesis. One embodiment of an L4-L5 facet joint prosthesis 2200 (FIGS. 22A-22C, 22E) and footprint of the L4-L5 facet joint (FIG. 22D, 22F) is schematically illustrated and described in connection with FIGS. 22A-22F, and also illustrating a non-limiting example of dimensions. A lumbar facet joint prosthesis 2200 can include any number of features as disclosed elsewhere herein, including ball-and-trough components, for example. A prosthesis 2200 can include a superior articular process (SAP) component 2204 having a concave articular surface 2208 and an inferior articular process (IAP) component 2202 having a convex articular surface 2206. The convex articular surface 2206 can have a minor axis dimension x that is less than or equal to a width W of the IAP component 2202, for example, no more than about 10, 9, 8, 7, 6, or 5 mm, more or less, including ranges encompassing any of two of the foregoing values. The convex articular surface 2206 can have a major axis dimension y that is less than or equal to a width L of the IAP component 2202, for example no more than about 10, 9, 8, 7, 6, or 5 mm, more or less, including ranges encompassing any of two of the foregoing values. The concave articular surface 2208 of the SAP component 2204 can have a major axis dimension that is greater than the major axis dimension y of the convex articular surface 2206.

The bone facing surfaces of the SAP component 2204 and the IAP component 2202 can include anchoring elements 2052, 2050 as described elsewhere herein. Each component 2202, 2204 can include parallel anchoring elements 2052, 2050, respectively, separated by no more than about 8, 7, 6, 5, or 4 mm, more or less, including ranges encompassing any of two of the foregoing values.

Figure 22F:
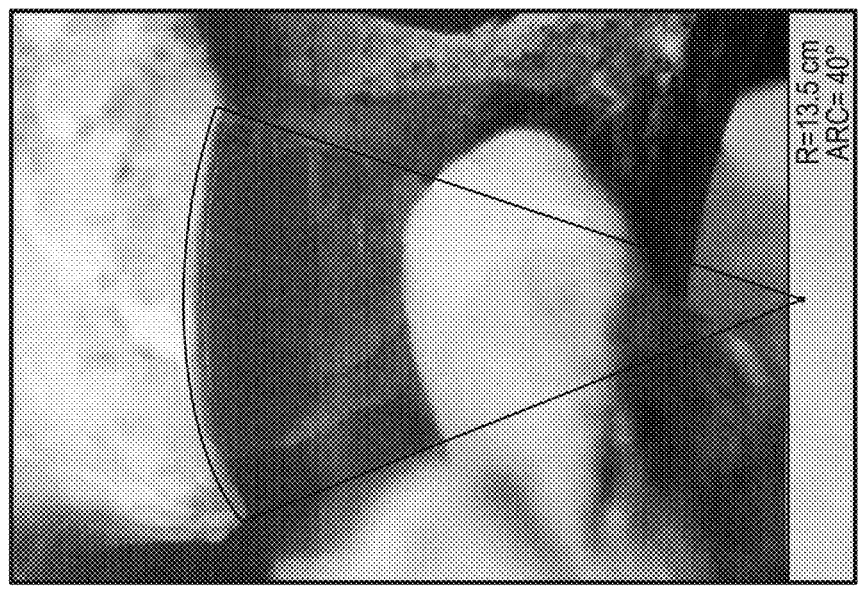
FIG. 22F illustrates a curved top view of an L5 SAP joint.

FIG. 22F illustrates a curved top view of an L5 SAP joint, including a radius of curvature of between about 12 cm and about 15 cm, such as about 13.5 cm in some cases, and having an arc of between about 30 degrees and about 50 degrees, such as about 40 degrees. The bone facing surfaces of the SAP component 2202 and the IAP component 2204 can be contoured to match the radius of the curvature of the anatomy.

Figure 22E:
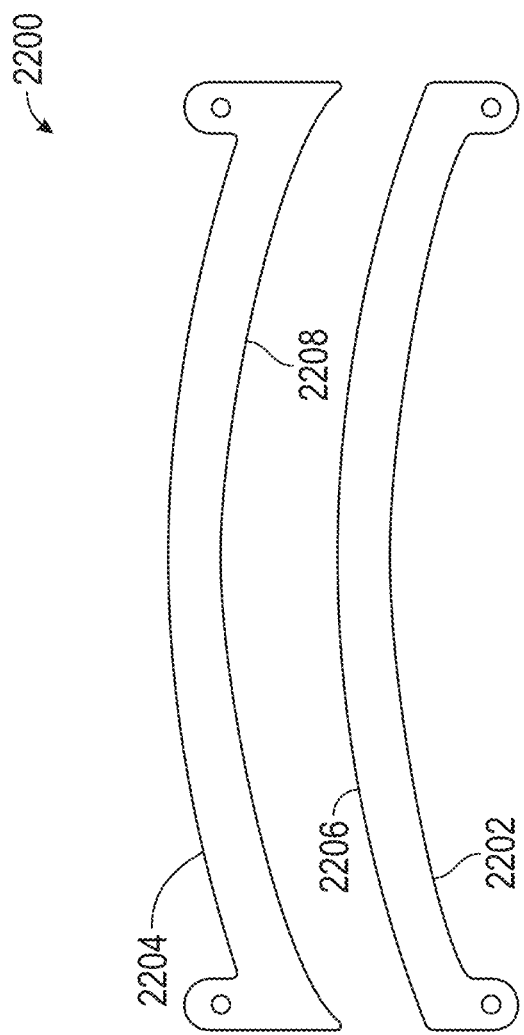

With the curved width of the prosthesis 2200, the prosthesis 2200 may need to be anchored along its width side W as shown schematically in FIGS. 22C and 22E. In some embodiments, the length L of the SAP and/or the IAP components 2202, 2204 can be between about 12 mm and about 16 mm, such as about 14.3 mm in some cases. In some embodiments, the width W of the SAP component 2202 and/or IAP component 2204 can be between about 10 mm and about 16 mm, such as about 13 mm. In some embodiments, the thickness T of the SAP component 2202 and/or the IAP component 2204 can be no more than about 7 mm, such as no more than about 5 mm, no more than about 3 mm, or no more than about 1 mm.

Figure 22G:
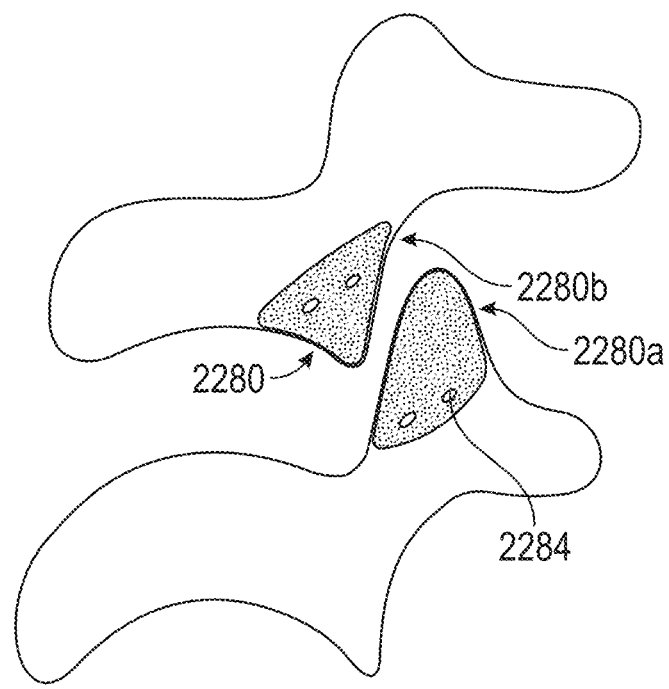
FIGS. 22G-22H illustrate another joint prosthesis that can be placed in a lumbar facet joint.
Figure 22H:
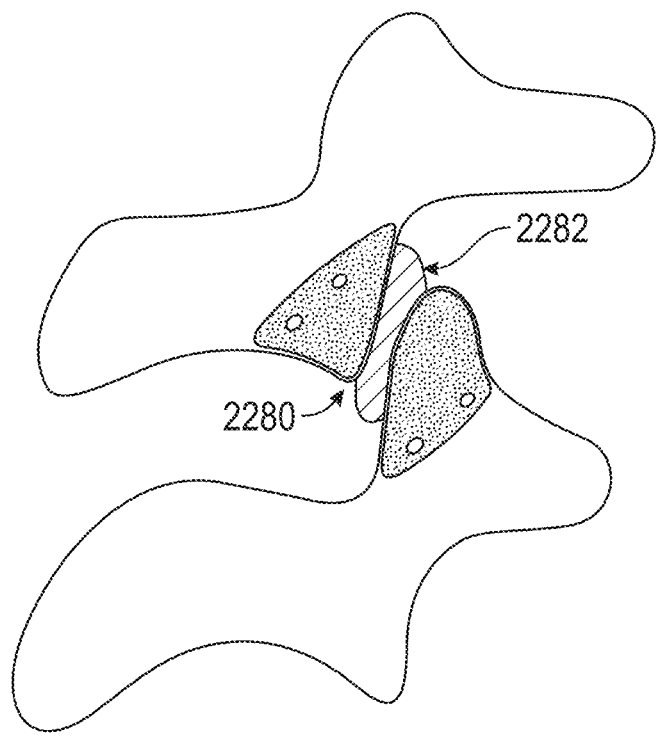

FIGS. 22G-22H illustrate another embodiment of an artificial lumbar joint prosthesis 2280, that can include a sheath or covering 2280a, 2280b made of metal or another biocompatible material configured to at least partially cover the IAP and the SAP. In some embodiments, both the IAP and SAP sheaths 2280a, 2280b comprise metal. In some embodiments, one of the IAP and/or SAP sheaths 2280a, 2280b can comprise metal, while the other can comprise a plastic, polymer, or other non-metal material. The IAP and SAP sheaths 2280a, 2280b can be secured using one or more bone screws 2284. A spacer 2282 can be present in between the IAP and SAP components (see FIG. 22H).

Figure 22I:
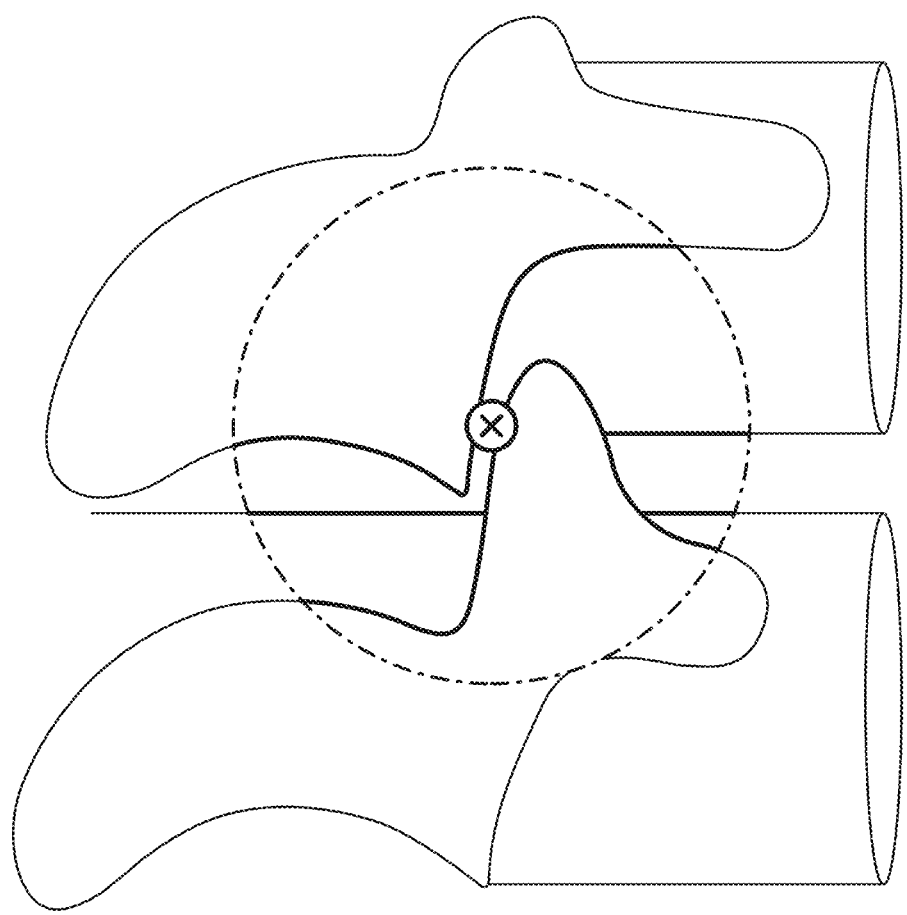
FIG. 22I illustrates an access approach to installing a lumbar facet joint prosthesis.

A minimally invasive approach to installing a lumbar facet joint prosthesis can include any number of the following, and one view illustrated in FIG. 22I. In the prone position, lumbar vertebral end plates are made in parallel in AP view with spinous process midway between articular pillars. C-arm can be positioned oblique ipsilaterally to visualize the targeted facet joint. K-wire can be introduced into the targeted facet joint and position confirmed on lateral fluoroscopic imaging. The Seldinger approach can then be utilized to obtain a working channel. An O-arm can be considered for challenging anatomy.

Figure 29E:
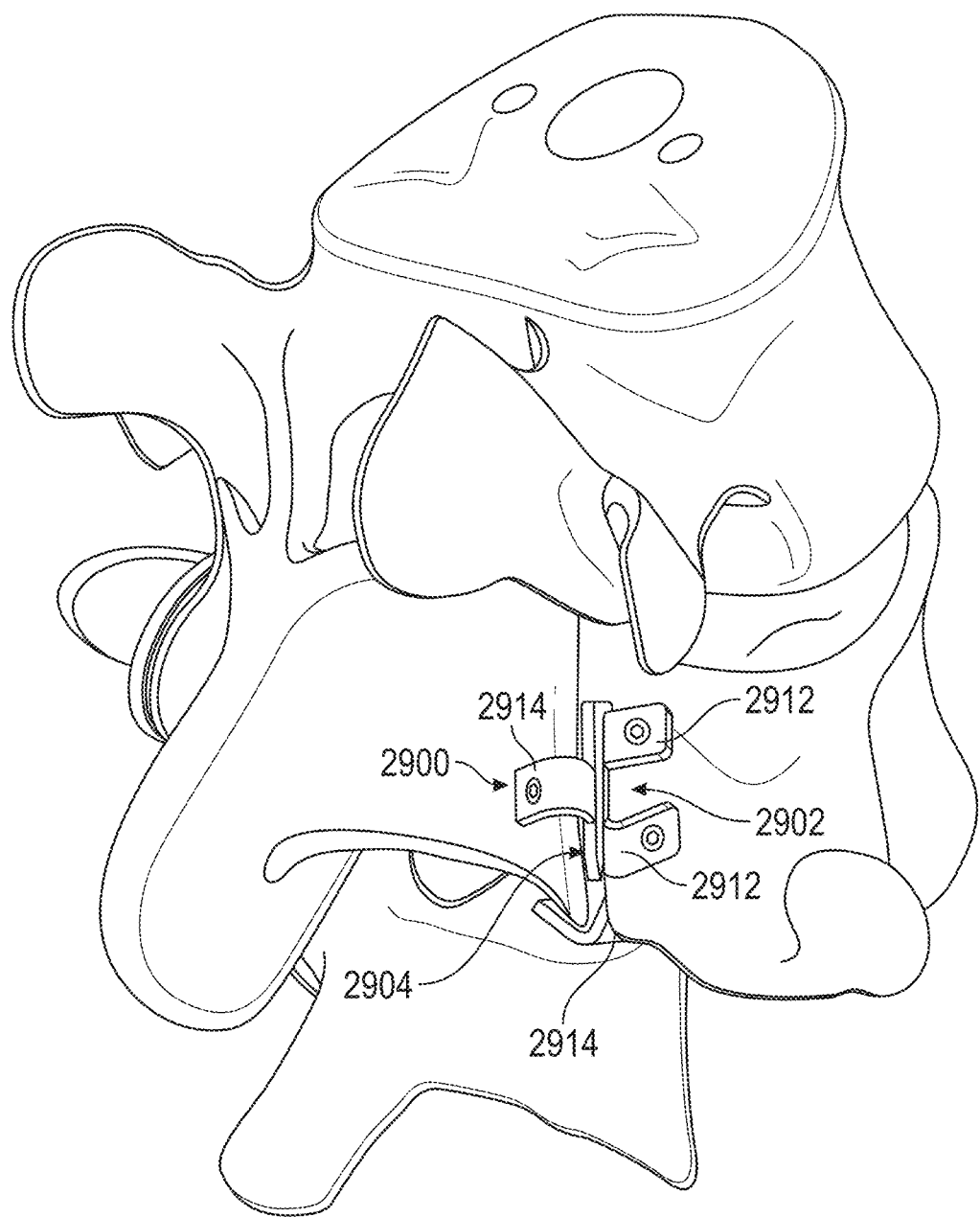

FIGS. 29A-29E illustrate a lumbar facet joint prosthesis 2900. The lumbar prosthesis 2900 can include a first component 2902 that can be secured to a one vertebrae and a second component 2904 secured to an adjacent vertebrae. As shown in FIG. 29E, the prosthesis 2900 may be positioned between the superior and inferior articular facets of adjacent vertebrae without extending to the disc space. The first component 2902 can have one or more flanges 2912 to secure the first component 2902 around the rim of the superior articular process. The second component 2902 can have one or more flanges 2914 to secure the second component 2902 around the rim of the inferior articular process.

The first component 2902 can include a body portion 2920 having an articulating surface and a bone facing surface. The body portion 2920 can have a generally rounded, but non-circular periphery (see FIG. 29B). A length (or major axis dimension) of the body portion 2920 can be no more than about 20, 19, 18, 17, 16, 15, 14, 13 mm, more or less, including ranges encompassing any of two of the foregoing values. A width (or minor-axis dimension) of the body portion can be no more than about 15, 14, 13, 12, 10, 9, 8 mm, more or less, including ranges encompassing any of two of the foregoing values. A thickness of the body portion can be no more than about 2.0, 1.5, 1.0 mm, more or less, including ranges encompassing any of two of the foregoing values.

The first component 2902 can include a convex surface 2906 extending from the articulating surface. The convex surface 2906 can be positioned inward of a periphery of the articulating surface. The convex surface 2906 may be centered on the body portion 2920 or at least extend over a center of the body portion. The convex surface 2906 extends across only a portion of the articulating surface. The convex surface 2906 can include any of the shapes or dimensions of the other ball elements described herein. A diameter of the convex surface 2906 can be more than about 10, 9, 8, 7, 6, 5 mm, more or less, including ranges encompassing any of two of the foregoing values.

The first component 2902 can include one or more flanges 2912 extending from the body portion. Each flange 2912 may be bent at an angle is configured to be contoured about a rim of the articular process (see FIG. 29E). For example, each flange 2912 may be bent at an angle of less than or equal to about 90 degrees, less than or equal to about 60 degrees, less than or equal to about 50 degrees, less than or equal to about 45 degrees, or less than or equal to about 40 degrees. As illustrated, the first component 2902 has two flanges 2912, but fewer or greater flanges are contemplated. The flanges 2912 can be on the same side of the body portion

2920, for example within 180 degrees of each other about a periphery of the body portion 2920, or within 135 degrees, or within 90 degrees. A width of each flange 2912 may be no more than about 5 mm, no more than about 4 mm, or no more than about 3 mm. A height of each flange 2912 from the body portion 2920 to a free end of the flange 2912 may be no more than about 7, 5, 4, 3 mm, more or less, including ranges encompassing any of two of the foregoing values. A thickness of each flange 2912 may be no more than 2.0 mm, no more than 1.5 mm, or no more than about 1.0 mm. Each flange 2912 can include an aperture configured to house a bone screw.

The second component 2904 can include similar length and width dimensions as the first component 2902. A thickness of the body portion 2922 of the second component 2904 may be greater than a thickness of the body portion 2920 of the first component 2902. A thickness of the body portion 2922 of the second component 2902 can be no more than about 2.0, 1.5, 1.0 mm, more or less, including ranges encompassing any of two of the foregoing values.

The second component 2904 can include a concave surface 2908 recessed in the articulating surface. The body portion 2922 of the second component 2904 may be sufficiently thick to accommodate the concave surface 2908 such that the bone facing surface of the second component 2904 may be generally flat. The concave surface 2908 can be positioned inward of a periphery of the articulating surface. The concave surface 2908 may be centered on the body portion 2922 or at least extend across a center of the body portion 2922. The concave surface 2908 extends across only a portion of the articulating surface. The concave surface 2908 can include any of the shapes or dimensions of the other trough elements described herein. A surface area of the concave surface 2908 may be larger than the convex surface 2906 on the first component 2902. A major axis dimension of the concave surface 2908 can be no more than about 14, 13, 12, 10, 9, 8 mm, more or less, including ranges encompassing any of two of the foregoing values. A minor axis dimension of the concave surface 2908 can be no more than about 10, 9, 8, 7, 6 mm, more or less, including ranges encompassing any of two of the foregoing values. Each of the major and minor axis dimensions of the concave surface 2908 may be greater than a diameter of the convex surface 2906.

The second component 2904 can include one or more flanges 2914 extending from the body portion 2922. Each flange 2914 may be bent at an angle is configured to be contoured about a rim of the articular process. For example, each flange 2914 may be bent at an angle of less than or equal to about 90 degrees, less than or equal to about 60 degrees, less than or equal to about 50 degrees, less than or equal to about 45 degrees, or less than or equal to about 40 degrees. As illustrated, the second component 2904 has two flanges 2014, but fewer or greater flanges are contemplated. The flanges can be on the same side of the body portion, for example within 180 degrees of each other about a periphery of the body portion, or within 135 degrees, or within 90 degrees. The flanges 2914 on the second component 2904 may be spaced further apart than the flanges 2012 on the first component 2902. A width of each flange 2914 may be no more than about 5 mm, no more than about 4 mm, or no more than about 3 mm. A height of each flange 2914 from the body portion to a tip of the flange 2914 may be no more than about 7, 5, 4, 3 mm, more or less, including ranges encompassing any of two of the foregoing values. A thickness of each flange 2914 may be no more than 2.0 mm, no more than 1.5 mm, or no more than about 1.0 mm. Each flange 2914 can include an aperture configured to house a bone screw. As shown in FIG. 29E, when implanted, the flanges 2912 of the first component 2902 and the flanges 2914 of the second component 2904 may be staggered relative to each other.

As shown in FIGS. 29B and 29D, one or both of the components 2902, 2904 can have one or more anchoring elements 2952, 2950 to anchor the components 2902, 2904 to the facet joint. The anchoring elements 2952, 2950 may extend along less than an entire length or width of the respective components 2902, 2904. As illustrated, the anchoring elements 2952, 2950 may extend along the major axes of the components 2902, 2904 and parallel to each other. But in other configurations, the anchoring elements 2952, 2950 may extend along a different direction of the components 2902, 2904, for example along the minor axes, and/or at a different angle relative to each other, for example in a toe-in configuration. The anchoring elements 2952, 2950 may include any of the features of the other anchoring elements described herein. In some embodiments, the prosthesis or any element thereof can comprise a biocompatible material, such as a metal such as titanium, for example. Each of the first component 2902 and the second component 2904 can be a monolithic element. Although, in some embodiments, the anchoring elements 2952, 2950 may be separately attached to the respective body portions 2920, 2922.

Additionally or alternatively, the first component 2902 and the second component 2904 may be secured by an expandable anchor having any of the features of the anchoring elements 2750, 2852, 2850 described herein. For example, expandable anchors may be advanced through the apertures in the flanges 2912, 2914 to secure the prosthesis in the bone.

Although certain features are described with respect to the first component 2902 or second component 2904, any of the features described herein are interchangeable between the two elements 2902, 2904.

Sacroiliac

In some embodiments, systems and methods as disclosed herein can be used or modified for use as a sacroiliac (SI) joint prosthesis. The SI joint has unique characteristics not found in other diarthrodial joints. The SI joint has fibrocartilage in addition to hyaline cartilage. There is discontinuity of the posterior capsule. The articular surfaces can have many ridges and depressions that minimize movement and enhance stability. The primary stability, however, can occur due to many adjacent ligaments.

Figure 23A:
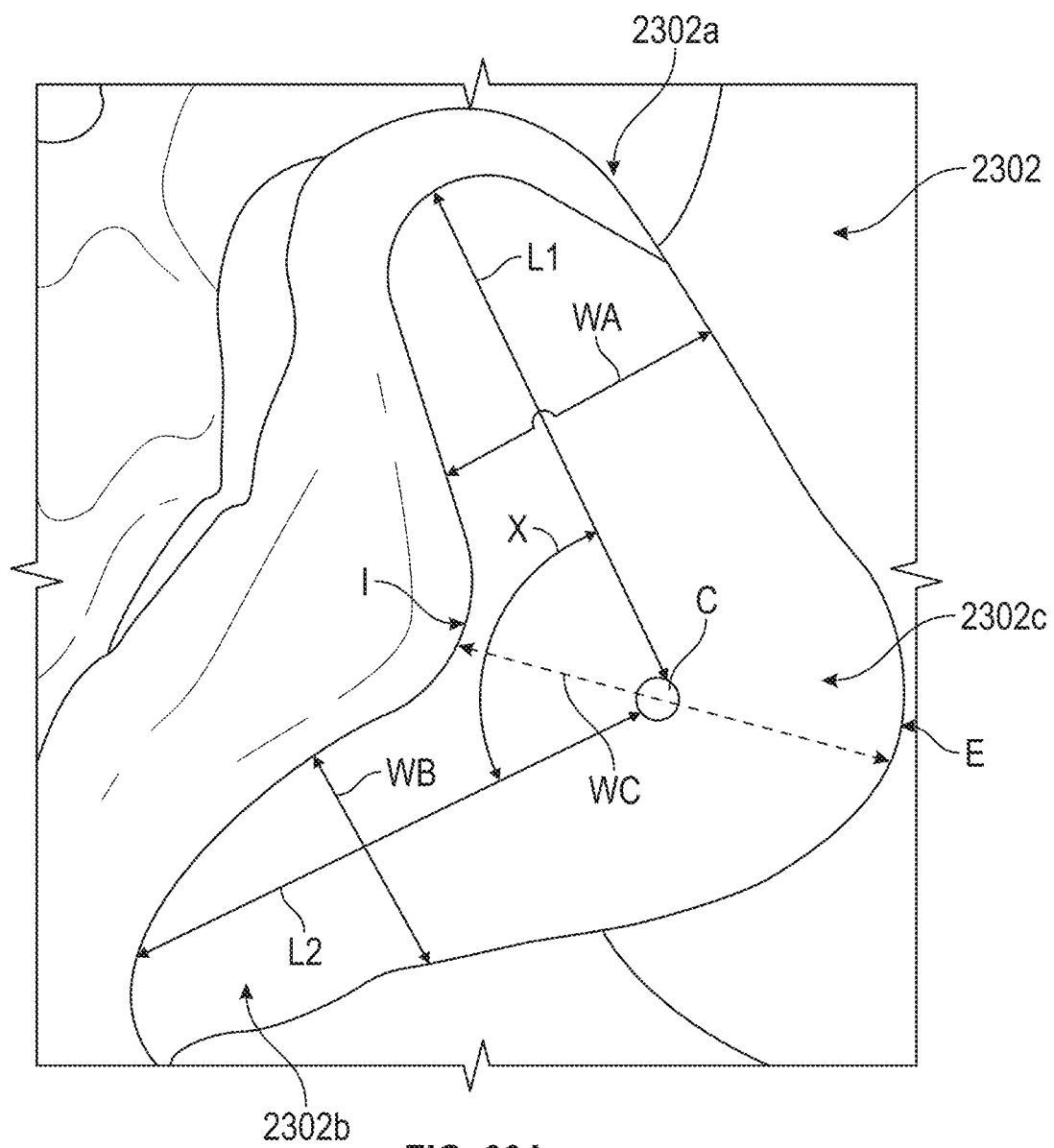
FIGS. 23A-23B illustrate a footprint of sacral component of a sacroiliac joint prosthesis.
Figure 23B:
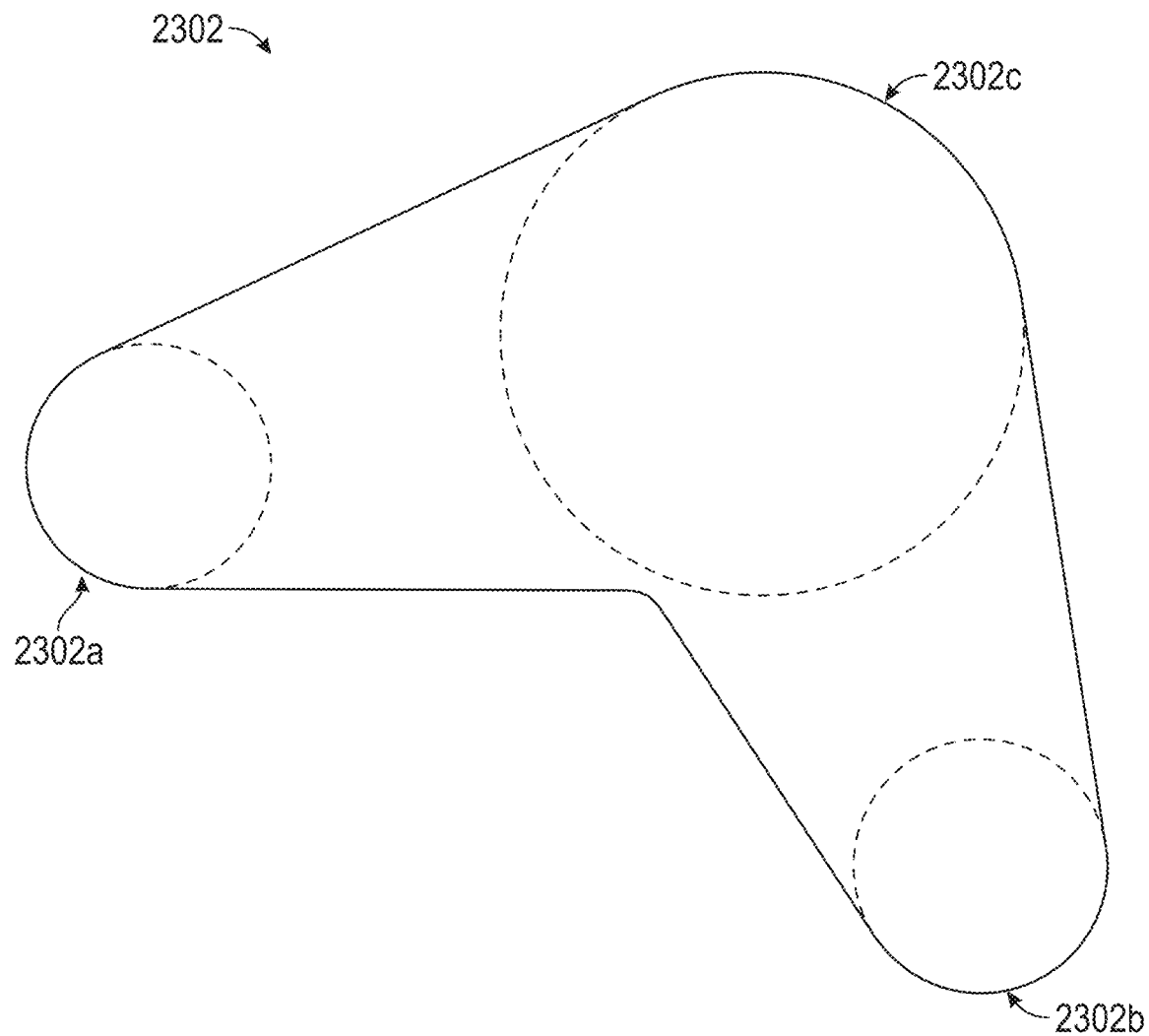

FIG. 23A illustrates non-limiting dimensions of a footprint of a sacral component 2302 on the sacral joint. FIG. 23B schematically illustrates one embodiment of a sacral component footprint without the anatomy. The sacral component 2302 can include a first end portion 2302a and a second end portion 2302b joined by an intermediate portion 2302c. The first end portion 2303a can be angled relative to the second end portion 2302b through the intermediate portion 2302c to form a V-shaped footprint. For example, the first end portion 2302a may be angled relative to the second end portion 2302b by angle X, which may be less than or equal to about 135 degrees, 115 degrees, 110 degrees, 100 degrees, 90 degrees, more or less, including ranges encompassing any of two of the foregoing values.

The intermediate portion 2302c can include a width WC measured from the interior periphery I to the exterior periphery E. The width WC can be no more than about 45 mm, 40 mm, 35 mm, 30 mm, more or less, including ranges encompassing any of two of the foregoing values. The radius of curvature of the exterior edge E of the intermediate portion 2302c can be less than or equal to about 20, 19, 18, 17, 16, 15, 14 mm, more or less, including ranges encompassing any of two of the foregoing values. As illustrated in FIG. 23B, a best-fit circle of the intermediate portion 2302c can have a larger radius of curvature than a best-fit circle of the first end portion 2302a and/or the second end portion 2302b.

The first end portion 2302a and the second end portion 2302b can have a width WA, WB, respectively, measured between the interior periphery I and the exterior periphery E, that is less than the width WC of the intermediate portion 2302c. The width WA of the first end portion 2302a and/or width WB of the second end portion 2302 can be less than or equal to about 20, 19, 18, 17, 16, 15, 14, 13, 12, 11 mm, more or less, including ranges encompassing any of two of the foregoing values. The width WA of the first end portion 2302a may be the same as the width WB of the second end portion 2302b.

The sacral component 2302 may be asymmetrical. For example, the first end portion 2302a may be longer than the second end portion 2302b. The first end portion 2302a may have a length L1 measured from a center C of the intermediate portion 2302c that is less than or equal to about 40, 38, 36, 34, 32, 30, 28, 26, 24, 22 mm, more or less, including ranges encompassing any of two of the foregoing values. The second end portion 2302b may have a length L2 measured from a center C of the intermediate portion 2302c that is less than or equal to about 36, 34, 32, 30, 28, 26 mm, more or less, including ranges encompassing any of two of the foregoing values.

Figure 23C:
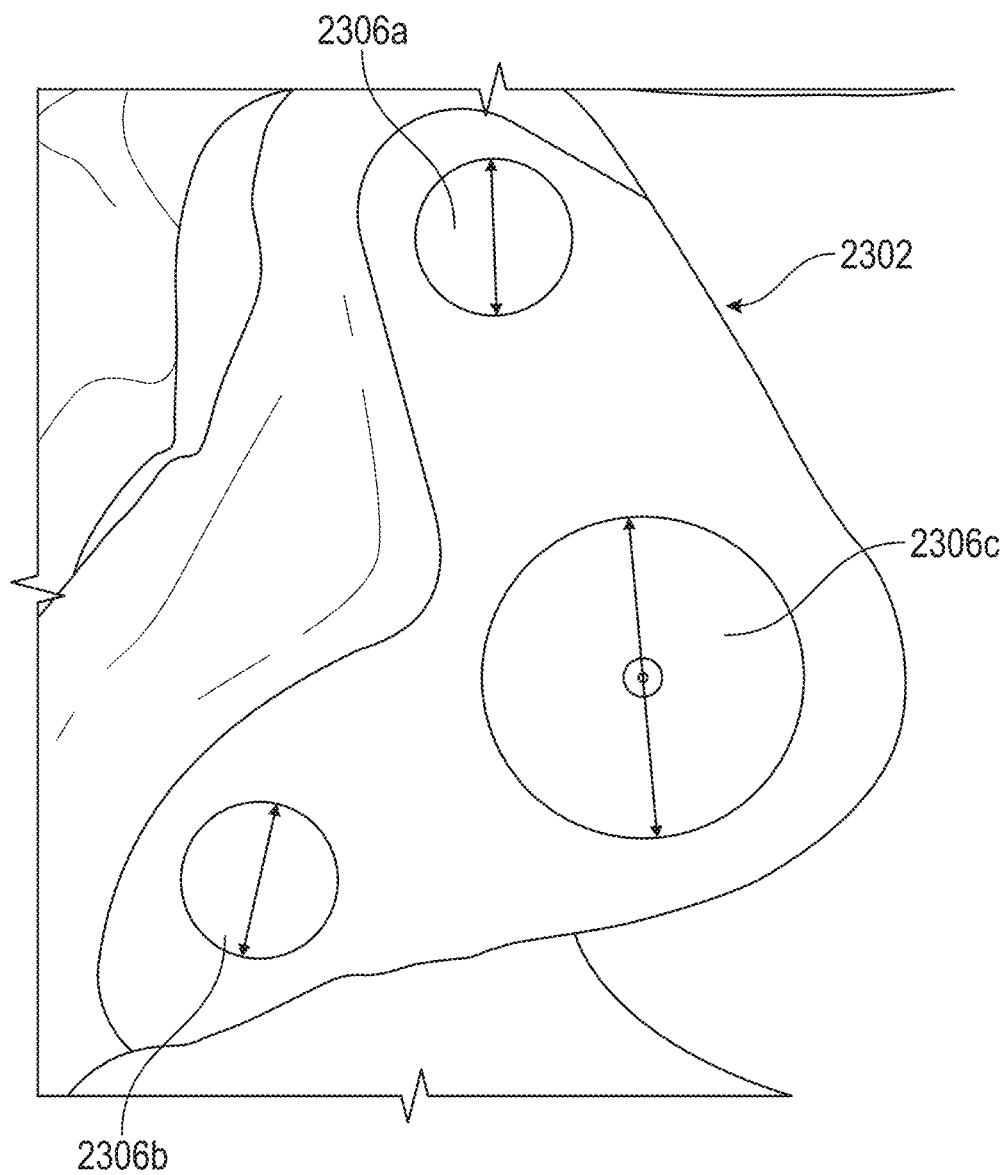
FIG. 23C schematically illustrates a sacral component that can be placed in the sacro-illiac joint.

FIG. 23C schematically illustrates that a sacral component prosthesis 2302 can include a plurality of ball-and-trough components, such as, for example, a central larger diameter ball-and-trough component 2306c, and a plurality of lateral smaller diameter ball-and-trough components 2306a, 2306b. The ball-and-trough components 2306a, 2306b, 2306c can be any combination of ball components or trough components, for example all ball components, all trough components, or a combination, that would interact with corresponding articular components on an iliac component. The ball-and-trough components can include features and dimensions as disclosed elsewhere herein. The central ball-and-trough component 2306c can have a diameter of no more than about 28, 26, 24, 22, 20, 18, 16, 14 mm, more or less, including ranges encompassing any of two of the foregoing values. The end portion ball-and-trough components 2306a, 2306b can have a diameter of no more than about 14, 12, 10, 8, 6 mm, more or less, including ranges encompassing any of two of the foregoing values. In other configurations, each of the ball-and-trough components may have a similar diameter.

A system can include a boomerang or V-shaped footprint (e.g., two linear wings with a central angled segment) in some embodiments as illustrated. The iliac component (not shown) can have a similar profile to the sacral component.

Figure 23D:
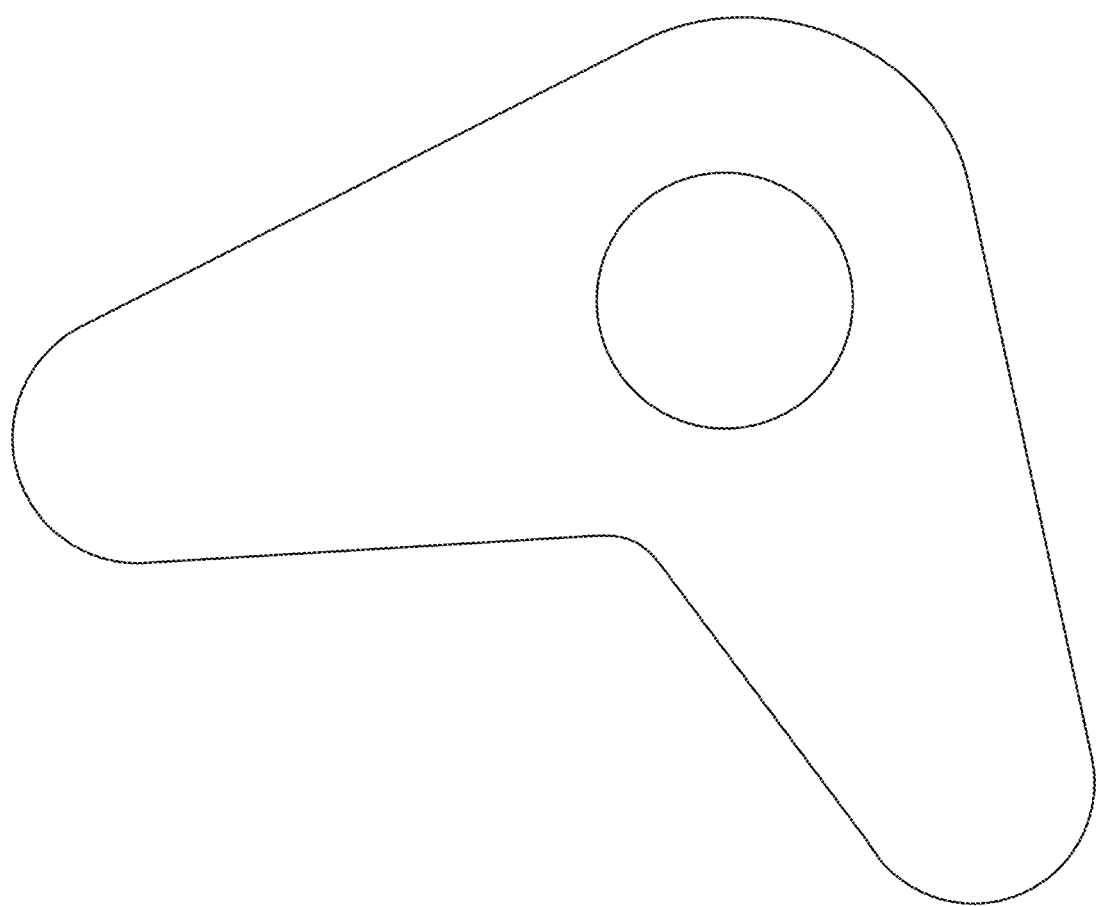
FIG. 23D schematically illustrates another sacral component that can be placed in the sacral-illiac joint.

FIG. 23D illustrates a system configured for implantation as an artificial sacral or SI joint component that includes a single central ball-and-trough component without lateral additional ball-and-trough components.

Use of an O-arm for intra-operative navigation can confirm accuracy of placement of the device win patients with difficult anatomy.

FIGS. 28A-28D illustrate different views of a sacro-illiac joint prosthesis 2800. The prosthesis 2800 can include a first component 2802 and a second component 2804. One component can be secured to the sacrum and the other component can be secured to the ilium. Each component 2802, 2804 can have any of the features described above with respect to the sacral component 2302, for example the dimensions and relative dimensions between the different portions of the prosthesis.

The overall length L of the first component 2802 and/or the second component 2804 may be no more than about 60, 59, 58, 57, 56, 55, 54, 53, 52, 51, 50 mm, more or less, including ranges encompassing any of two of the foregoing values. The overall width W of the first component 2802 and/or the second component 2804 can be less than the overall length L and may be no more than about 45, 44, 43, 42, 41, 40, 39, 38, 37, 36, 35 mm, more or less, including ranges encompassing any of two of the foregoing values.

The first component 2802 can have a body portion 2820 having an articulating surface and a bone-facing surface. The body portion 2820 can have a first end portion 2802a, a second end portion 2802b, and an intermediate portion 2802c. A thickness of the body portion 2820 can be no more than about 3 mm, no more than about 2 mm, or no more than about 1 mm. The first component 2802 can have one or more ball elements 2806a, 2806b, 2806c extending from the articulating surface of the body portion. For example, each of the first end portion 2802a, the second end portion 2802b, and the intermediate portion 2802c can have a respective ball element 2806a, 2806b, 2806c. A height of each ball element 2806a, 2806b, 2806c can be no more than about 2.0, 1.9, 1.8, 1.7, 1.6, 1.5 mm, more or less, including ranges encompassing any of two of the foregoing values.

The second component 2804 can have a body portion 2822 having an articulating surface and a bone-facing surface. The body portion 2822 can have a first end portion 2804a, a second end portion 2804b, and an intermediate portion 2804c. A thickness of the body portion 2822 can be no more than about 3 mm, no more than about 2 mm, or no more than about 1 mm. The second component 2804 can have one or more trough elements 2808a, 2808b, 2808c recessed in the articulating surface of the body portion and configured to articulate with the ball elements 2806a, 2806b, 2806c. For example, each of the first end portion 2804a, the second end portion 2804b, and the intermediate portion 2804c can have a respective trough element 2808a, 2808b, 2808c. A depth of each trough element 2808a, 2808b, 2808c can be greater than, equal to, or less than the height of the respective ball element 2806a, 2806b, 2806c depending on the desired range of motion. The depth can be no more than about 2.0, 1.9, 1.8, 1.7, 1.6, 1.5 mm, more or less, including ranges encompassing any of two of the foregoing values. A diameter of each trough element 2808a, 2808b, 2808c can be greater than or equal to the diameter of the respective ball element 2806a, 2806b, 2806c, for example at least about 1.25× or at least about 1.5×.

Each of the first component 2802 and the second component 2804 can include one or more anchoring elements 2852, 2850 on the bone facing surfaces. Unlike the anchoring element 2750, which extends through an aperture, the anchoring elements 2852, 2850 may be attached to the bone facing surfaces of the respective components 2802, 2804, for example along a length of the anchoring elements 2852, 2850.

For example, the first component 2802 can include one anchoring element 2852 on the first end portion 2802a and another anchoring element 2852 on the second end portion 2802b. The second component 2805 can include one anchoring element 2850 on the first end portion 2805a and another anchoring element 2850 on the second end portion 2805b. The anchoring elements 2852, 2850 can generally extend in a plane parallel to the plane of the respective body portions 2820, 2822. The anchoring elements 2852, 2850 can include any of the features of the anchoring elements described above with respect to other prostheses. As illustrated, the anchoring elements 2852, 2850 are positioned along the width dimension of the respective components 2802, 2804, e.g. from the first or second end portion 2802a, b and toward the intermediate portion 2802c, and parallel to each other, but in other configurations may be angled toward each other or oriented in other directions. The anchoring elements 2852, 2850 may extend from an interior or posterior edge I and toward an exterior or anterior edge E of the respective component 2802, 2804. A length of the anchoring element 2852, 2850 can be less than or equal to about 25 mm and/or at least about 15 mm, for example between 18 mm and 22 mm. A height of the anchoring element 2852, 2850, measured away from the respective body portion 2820, 2822 is no more than 5 mm, no more than 4 mm, no more than 3 mm.

Figure 28E:
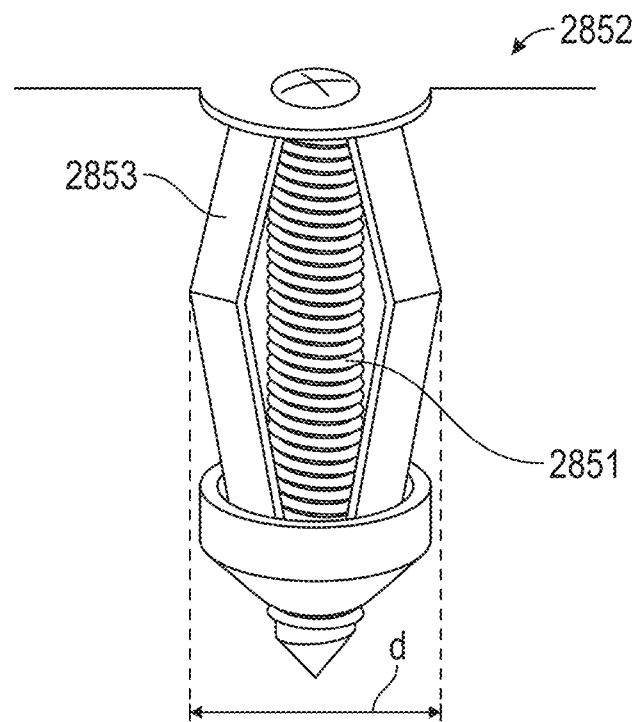
FIGS. 28E-28F illustrate detailed views of the expandable keel shown in FIG. 28A.
Figure 28F:
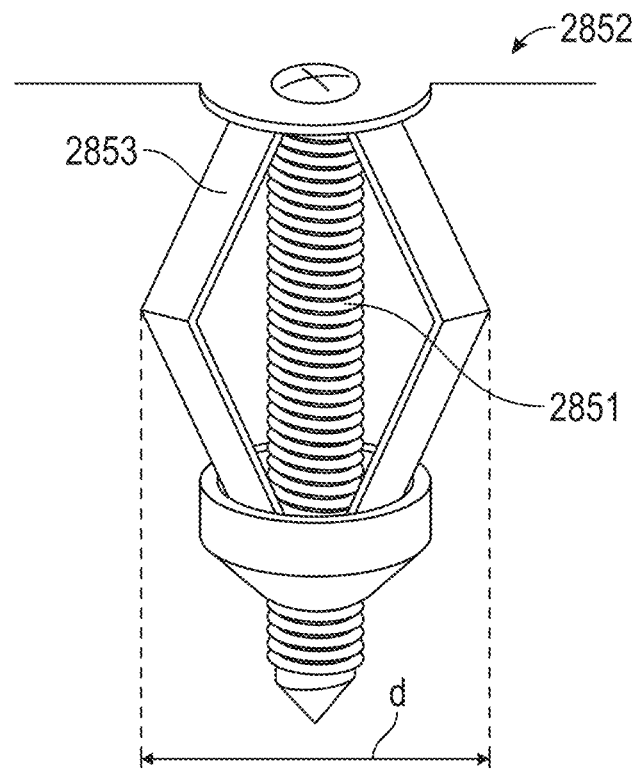

The anchoring elements 2852, 2850 may be expandable within the bone. For example, the anchoring elements 2852, 2850 may transition from a non-deployed configuration (see FIG. 28E) to a deployed configuration (see FIG. 28F). In the deployed configuration, the anchoring elements 2852, 2850 may have width d that is at least 1.5×, at least 2.0×, at least 2.5×, or at least 3× the width d of the anchoring elements 2852, 2850 in the undeployed configuration. When unexpanded, the anchoring elements 2852, 2850 can have a width of no more than about 5 mm, 4 mm, 3 mm, more or less, including ranges encompassing any of two of the foregoing values. When expanded, the anchoring elements 2852, 2850 can have a width of at least 10, 11, 12, 14, 15, 16 mm, more or less, including ranges encompassing any of two of the foregoing values.

As an example, the anchoring element 2852 may have an inner screw 2851 and an outer sleeve 2853. As the inner screw 2851 is turned, the distal tip of the sleeve 2853 moves towards the head of the inner screw 2851 such that the length of the sleeve 2853 shortens. As the length of the sleeve 2853 shortens, the width d of an the sleeve 2853 expands radially outward. The sleeve 2853 may include one or more struts that bow outward to anchor the prosthesis in bone. The distal tip of the sleeve 2853 may be tapered for greater screw purchase.

Although certain features are described with respect to the first component 2802 or second component 2804, any of the features described herein are interchangeable between the two elements 2802, 2804.

Systems and Kits

In some embodiments, the method does not fuse the joint in which the prosthesis is implanted. In some embodiments, one, two, or more non-intervertebral disc joint prostheses can be implanted concurrently with intervertebral disc prostheses. For example, one or more ball-and-trough type joint prostheses can be implanted into one or more facet joints at one or more spinal levels, and an additional ball-and trough type joint prostheses can be implanted into one or more intervertebral disc joints at the same or different spinal levels.

A system or kit may also be provided according to some embodiments, wherein the system or kit comprises a plurality of components described herein, for example one or more of the different prostheses described above or the same prostheses in different sizes within the ranges outlined above.

Terminology

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although certain features are described as being on a superior or inferior component of the prostheses, the features may be reversed such that features described as being on an inferior facing side of the superior component may be positioned on a superior facing side of the inferior component and vice versa.

For ease of reference, certain prostheses are described with respect to specific facet joints, but any of the prostheses described herein could be placed in any of the other facet joints.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps. However, some embodiments can consist or consist essentially of any number of stated elements or steps disclosed herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. The methods disclosed herein include certain actions taken by a practitioner; however, they can also include any third-party instruction of those actions, either expressly or by implication. For example, actions such as "percutaneously accessing the atlanto-axial joint includes instructing the percutaneous accessing of the atlanto-axial joint.

What is claimed is:

1. A facet joint prosthesis configured to be placed in a cervical facet joint, the facet joint prosthesis comprising:
   a first component configured to be attached to a first vertebrae, the first component comprising:
      a first body portion comprising a first generally flat surface and a convex articulating surface extending from the first generally flat surface, the first body portion further comprising a first bone facing surface opposite the first generally flat surface, the first body portion sized to be positioned on a first articular facet of the first vertebrae without extending into a disc space;
      a first flange extending from the first body portion and configured to be secured to a posterior facing side of the first vertebrae, the first flange comprising a first aperture; and
      a first expandable anchor configured to extend through the first aperture; and
   a second component configured to be attached to a second vertebrae adjacent the first vertebrae, the second component comprising:
      a second body portion comprising a second generally flat surface and a concave articulating surface recessed from the second generally flat surface, the second body portion further comprising a second bone facing surface opposite the second generally flat surface, the second body portion sized to be positioned on a second articular facet of the second vertebrae without extending into the disc space;
      a second flange extending from the second body portion and configured to be secured to a posterior facing side of the second vertebrae, the second flange comprising a second aperture; and
      a second expandable anchor configured to extend through the second aperture;
   wherein the convex articulating surface and the concave articulating surface are sized and shaped to allow the first component to translate relative to the second component in an anterior-posterior direction and a medial-lateral direction when implanted;
   wherein the convex articulating surface and the concave articulating surface are sized and shaped to allow the first component to tilt relative to the second component in the anterior-posterior direction and the medial-lateral direction when implanted;

wherein the convex articulating surface and the concave articulating surface are sized and shaped to allow the first component to rotate relative to the second component; and wherein each of the concave articulating surface and the convex articulating surface is non-spherical with a major dimension and a minor dimension, wherein the major dimension of the concave articulating surface is greater than the major dimension of the convex articulating surface, and wherein the minor dimension of the concave articulating surface is greater than the minor dimension of the convex articulating surface.

2. The facet joint prosthesis of claim 1, wherein the second flange is shaped differently from the first flange.

3. The facet joint prosthesis of claim 1, wherein the first component comprises a first set of anchoring elements on the first bone facing surface, and wherein the second component comprises a second set of anchoring elements on the second bone facing surface.

4. The facet joint prosthesis of claim 3, wherein each of the first set of anchoring elements and the second set of anchoring elements comprises a pair of keels extending in the anterior-posterior direction, each keel comprising a linear array of saw teeth.

5. The facet joint prosthesis of claim 1, wherein a depth of the concave articulating surface is less than a thickness of the convex articulating surface.

6. The facet joint prosthesis of claim 1, wherein the first component comprises a first pair of paddles extending laterally from the first body portion, and wherein the second component comprises a second pair of paddles extending laterally from the second body portion.

7. The facet joint prosthesis of claim 6, wherein the first pair of paddles of the first component are shaped differently from each other, and wherein the second pair of paddles of the second component are shaped differently from each other.

8. The facet joint prosthesis of claim 1, wherein each of the first expandable anchor and the second expandable anchor comprises an inner screw and an outer sleeve, the outer sleeve is configured to expand outward as the inner screw is driven into the first vertebrae or the second vertebrae.

9. A facet joint prosthesis configured to be placed in a cervical facet joint, the facet joint prosthesis comprising:
   a first component configured to be attached to a first vertebrae, the first component comprising:
      a first body portion comprising a first generally flat surface around a perimeter of the first body portion, a convex articulating surface projecting from the first generally flat surface, and a first bone facing surface opposite the first generally flat surface, the first body portion sized to be positioned on a first articular facet of the first vertebrae without extending into a disc space;
      a single first flange extending from the first body portion and configured to be secured to a posterior facing side of the first vertebrae, the first flange comprising a first aperture; and
      a first pair of keels on the first bone facing surface extending in the anterior-posterior direction, the first flange positioned between the first pair of keels; and
   a second component configured to be attached to a second vertebrae adjacent the first vertebrae, the second component comprising:
      a second body portion comprising a second generally flat surface around a perimeter of the second body portion, a concave articulating surface recessed in the second generally flat surface, and a second bone facing surface opposite the second generally flat surface, the second body portion configured to be positioned on a second articular facet of the second vertebrae without extending into the disc space;
      a single second flange extending from the second body portion and configured to be secured to a posterior facing side of the second vertebrae, the second flange comprising a second aperture; and
      a second pair of keels on the second bone facing surface extending in the anterior-posterior direction, the second flange positioned between the second pair of keels; and
   wherein the convex articulating surface and the concave articulating surface are sized and shaped to allow the first component to translate relative to the second component in an anterior-posterior direction and a medial-lateral direction when implanted;
   wherein the convex articulating surface and the concave articulating surface are sized and shaped to allow the first component to tilt relative to the second component in the anterior-posterior direction and the medial-lateral direction when implanted; and
   wherein the convex articulating surface and the concave articulating surface are sized and shaped to allow the first component to rotated relative to the second component.

10. The facet joint prosthesis of claim 9, wherein a depth of the concave articulating surface is less than a thickness of the convex articulating surface.

11. The facet joint prosthesis of claim 9, wherein each of the concave articulating surface and the convex articulating surface is non-spherical with a major dimension and a minor dimension.

12. The facet joint prosthesis of claim 11, wherein the major dimension of the concave articulating surface is greater than the major dimension of the convex articulating surface, and wherein the minor dimension of the concave articulating surface is greater than the minor dimension of the convex articulating surface.

13. A facet joint prosthesis configured to be placed in a cervical facet joint, the facet joint prosthesis comprising:
   a first component configured to be attached to a first vertebrae, the first component comprising:
      a first body portion comprising a convex articulating surface and a first bone facing surface, the first body portion sized to be positioned on a first articular facet of the first vertebrae without extending into a disc space;
      a first flange extending from the first body portion and configured to be secured to a posterior facing side of the first vertebrae, the first flange comprising a first aperture; and
      a first expandable anchor configured to extend through the first aperture; and
   a second component configured to be attached to a second vertebrae adjacent the first vertebrae, the second component comprising:
      a second body portion comprising a concave articulating surface and a second bone facing surface, the second body portion configured to be positioned on a second articular facet of the second vertebrae without extending into the disc space;

a second flange extending from the second body portion and configured to be secured to a posterior facing side of the second vertebrae, the second flange comprising a second aperture; and a second expandable anchor configured to extend through the second aperture, wherein each of the first expandable anchor and the second expandable anchor comprises an inner screw and an outer sleeve, the outer sleeve having a proximal end portion, a distal end portion, and a plurality of struts extending between the proximal end portion and the distal end portion, the distal end portion of the outer sleeve is configured to move toward the proximal end portion as the inner screw is driven into the first vertebrae or the second vertebrae causing the plurality of struts to bow outward relative to the first end portion and the second end portion and the outer sleeve to shorten.

14. The facet joint prosthesis of claim 13, wherein the first component comprises a first set of anchoring elements on the first bone facing surface, and wherein the second component comprises a second set of anchoring elements on the second bone facing surface.

15. The facet joint prosthesis of claim 14, wherein each of the first set of anchoring elements and the second set of anchoring elements comprises a pair of keels extending in an anterior-posterior direction, each keel comprising a linear array of saw teeth.

16. The facet joint prosthesis of claim 13, wherein a depth of the concave articulating surface is less than a thickness of the convex articulating surface.

17. The facet joint prosthesis of claim 13, wherein each of the concave articulating surface and the convex articulating surface is non-spherical with a major dimension and a minor dimension.

18. The facet joint prosthesis of claim 17, wherein the major dimension of the concave articulating surface is greater than the major dimension of the convex articulating surface, and wherein the minor dimension of the concave articulating surface is greater than the minor dimension of the convex articulating surface.

19. A facet joint prosthesis configured to be placed in a cervical facet joint, the facet joint prosthesis comprising:

a first component configured to be attached to a first vertebrae, the first component comprising:

a first body portion comprising a convex articulating surface and a first bone facing surface, the first body portion comprising straight lateral edges on opposite sides of the convex articulating surface and extending in an anterior-posterior direction, the first body portion sized to be positioned on a first articular facet of the first vertebrae without extending into a disc space;

a single first flange extending posteriorly from the first body portion and configured to be secured to a posterior facing side of the first vertebrae, the first flange comprising a first aperture; and a first expandable anchor configured to extend through the first aperture; and a second component configured to be attached to a second vertebrae adjacent the first vertebrae, the second component comprising:

a second body portion comprising a concave articulating surface and a second bone facing surface, the second body portion comprising straight lateral edges on opposite sides of the concave articulating surface and extending in the anterior-posterior direction, the second body portion sized to be positioned on a second articular facet of the second vertebrae without extending into the disc space;

a single second flange extending posteriorly from the second body portion and configured to be secured to a posterior facing side of the second vertebrae, the second flange comprising a second aperture, the second flange extending at a non-zero angle relative to a longitudinal axis in a superior-inferior direction and shaped different from the first flange; and a second expandable anchor configured to extend through the second aperture;

wherein the convex articulating surface and the concave articulating surface are sized and shaped to allow the first component to translate relative to the second component in an anterior-posterior direction and a medial-lateral direction when implanted;

wherein the convex articulating surface and the concave articulating surface are sized and shaped to allow the first component to tilt relative to the second component in the anterior-posterior direction and the medial-lateral direction when implanted; and wherein the convex articulating surface and the concave articulating surface are sized and shaped to allow the first component to rotate relative to the second component.

20. The facet joint prosthesis of claim 19, wherein a depth of the concave articulating surface is less than a thickness of the convex articulating surface.

21. The facet joint prosthesis of claim 19, wherein each of the concave articulating surface and the convex articulating surface is non-spherical with a major dimension and a minor dimension.

22. The facet joint prosthesis of claim 21, wherein the major dimension of the concave articulating surface is greater than the major dimension of the convex articulating surface, and wherein the minor dimension of the concave articulating surface is greater than the minor dimension of the convex articulating surface.

23. The facet joint prosthesis of claim 19, wherein each of the first expandable anchor and the second expandable anchor comprises an inner screw and an outer sleeve, the outer sleeve is configured to expand outward as the inner screw is driven into the first vertebrae or the second vertebrae.

* * * * *

UNITED STATES PATENT AND TRADEMARK OFFICE
CERTIFICATE OF CORRECTION

PATENT NO. : 11,672,671 B2
APPLICATION NO. : 17/650952
DATED : June 13, 2023
INVENTOR(S) : J. Patrick Johnson et al.

It is certified that error appears in the above-identified patent and that said Letters Patent is hereby corrected as shown below:

In the Drawings

On Sheet 5 of 73, Line 3 (Approx.), FIG. 3C, delete "Memerane" and insert --Membrane--.

In the Specification

In Column 1, Line 37, delete "sacro-illiac" and insert --sacro-iliac--.

In Column 7, Line 4, delete "sacro-illiac" and insert --sacro-iliac--.

In Column 7, Line 5, delete "sacro-illiac" and insert --sacro-iliac--.

In Column 7, Line 11, delete "illium" and insert --ilium--.

In Column 7, Line 13, delete "sacro-illiac" and insert --sacro-iliac--.

In Column 7, Line 15, delete "sacro-illiac" and insert --sacro-iliac--.

In Column 7, Line 16, delete "sacro-illiac" and insert --sacro-iliac--.

In Column 7, Line 25, delete "illium" and insert --ilium--.

In Column 7, Line 27, delete "sacro-illiac" and insert --sacro-iliac--.

In Column 8, Line 46, delete "sacro-illiac" and insert --sacro-iliac--.

In Column 8, Line 48, delete "sacral-illiac" and insert --sacral-iliac--.

In Column 9, Lines 8-9 (Approx.), delete "(fibrocartilagenous)," and insert --(fibrocartilaginous),--.

Signed and Sealed this
Seventeenth Day of October, 2023

Katherine Kelly Vidal
*Director of the United States Patent and Trademark Office*

In Column 9, Line 26, delete "occiptal" and insert --occipital--.

In Column 11, Lines 6-7, delete "transverserium" and insert --transversarium--.

In Column 41, Line 63, delete "sacro-illiac" and insert --sacro-iliac--.

In Column 43, Line 37, delete "an the" and insert --the--.

In Column 46, Line 22, delete ""percutaneously" and insert --percutaneously--.

In the Claims

In Column 48, Claim 9, Line 32, delete "rotated" and insert --rotate--.